(12) United States Patent
Vogels et al.

(10) Patent No.: US 7,238,528 B2
(45) Date of Patent: *Jul. 3, 2007

(54) MEANS AND METHODS FOR FIBROBLAST-LIKE OR MACROPHAGE-LIKE CELL TRANSDUCTION

(75) Inventors: Ronald Vogels, Linschoten (NL); Govert Johan Schouten, Leiderdorp (NL); Abraham Bout, Moerkapelle (NL); Menzo Jans Emco Havenga, Alphen a/d Rijn (NL)

(73) Assignee: Crucell Holland B.V., Leiden (NL)

( * ) Notice: Subject to any disclaimer, the term of this patent is extended or adjusted under 35 U.S.C. 154(b) by 346 days.

This patent is subject to a terminal disclaimer.

(21) Appl. No.: 10/783,510

(22) Filed: Feb. 20, 2004

(65) Prior Publication Data

US 2004/0142473 A1 Jul. 22, 2004

Related U.S. Application Data

(63) Continuation of application No. 09/517,898, filed on Mar. 3, 2000, now Pat. No. 6,869,936.

(60) Provisional application No. 60/122,732, filed on Mar. 4, 1999, provisional application No. 60/123,061, filed on Mar. 5, 1999.

(51) Int. Cl.
    *C12N 15/00* (2006.01)
(52) U.S. Cl. .................. 435/455; 435/325; 435/320.1; 424/93.1; 424/93.2; 424/93.21
(58) Field of Classification Search .................. None
    See application file for complete search history.

(56) References Cited

U.S. PATENT DOCUMENTS

| 5,585,254 | A | 12/1996 | Maxwell et al. |
| 5,631,236 | A | 5/1997 | Woo et al. |
| 5,770,442 | A | 6/1998 | Wickham et al. |
| 5,861,290 | A | 1/1999 | Goldsmith et al. |
| 6,329,190 | B1 | 12/2001 | Wickham et al. |
| 6,455,314 | B1 | 9/2002 | Wickham et al. |
| 6,869,936 | B1 * | 3/2005 | Vogels et al. ............. 514/44 |

FOREIGN PATENT DOCUMENTS

| EP | 99201545.3 | 5/1999 |
| EP | 0 978 566 A2 | 2/2000 |
| WO | WO 96/26281 | 8/1996 |
| WO | WO 97/00326 | 1/1997 |
| WO | WO 98/32842 | 7/1998 |
| WO | WO 98/50053 | 11/1998 |
| WO | WO 00/52186 | 9/2000 |

OTHER PUBLICATIONS

D'andrea et al, Biochem J. 1998;329:681-7.*

Basler et al., "Sequence of the immunoregulatory early region 3 and flanking sequences of adenovirus type 35," Gene, 1996, pp. 249-254, vol. 170.

Flomenberg et al., "Molecular Epidemiology Adenovirus Type 35 Infections in Immunocompromised Hosts," The Journal of Infectious Diseases, Jun. 1987, pp. 1127-1134, vol. 155, No. 6.

Flomenberg et al., "Sequence and genetic Organization of Adenovirus Type 35 Early Region 3," Journal of Virology, Nov. 1988, pp. 4431-4437, vol. 62, No. 11.

Gahery-Segard et al., "Immune response to recombinant Capsid Proteins of Adenovirus in Humans: Antifiber and Anti-Penton Base Antibodies Have a Synergistic Effect on Neutralizing Activity," Journal of Virology, Mar. 1998, pp. 2388-2397, vol. 72, No. 3.

Kang et al., "Molecular Cloning and Physical Mapping of the DNA of Human Adenovirus Type 35," Acta Microbiologica Hungarica, 1999, pp. 67-75, vol. 36, No. 1.

Krasnykh et al., "Generation of Recombinant Adenovirus Vectors with modified Fibers for Altering Viral Tropism," Journal of Virology, Oct. 1996, pp. 6839-3846, vol. 70, No. 10.

Notice of Opposition to a European Patent, Patent No. 1054064, by Cell Genesys Inc., dated Jul. 5, 2005.

Rosenfeld et al., Adenovirus-Mediated Transfer of a recombinant alpha-1-Antitrypsin Gene to the Lung Epithelium in Vivo, Science, Apr. 19, 1991, pp. 431-434, vol. 252.

Roy et al., "Circumvention of Immunity to the Adenovirus major Coat Protein Hexon," Journal of Virology, Aug. 1998, pp. 6875-6879, vol. 72, No. 8.

Stevenson et al., "Human Adenovirus Serotypes 3 and 5 Bind to Two Different Cellular receptors via the Fiber Head Domain," Journal of Virology, May 1995, pp. 2850-2857, vol. 69, No. 5.

Stratford-Perricaudet et al., "Evaluation of the Transfer and Expression in Mice of an Enzyme-Encoding Gene Using a Human Adenovirus Vector," Human Gene Therapy, 1990, pp. 241-256, vol. 1.

Boucher et al., J. Clin. Invest., Feb. 1999, pp. 441-445, vol. 103.
Bowie et al., Science, Mar. 1990, pp. 1306-1310, vol. 247.
Crystal et al., Transfer of Gene to Human: Early Lessons and Obstacles to Success, 1995, Science, vol. 270, pp. 404-410.
Deonarain, Expert Opin. Ther. Pat., 1998, pp. 53-69, vol. 8.
Eck et al., Gene-Based Therapy, 1996 Goodman & Gilman's, pp. 77-101.

(Continued)

Primary Examiner—Q. Janice Li
(74) Attorney, Agent, or Firm—TraskBritt

(57) ABSTRACT

The invention provides a nucleic acid delivery vehicle with or having been provided with at least a tissue tropism for fibroblast-like or macrophage-like cells, preferably synoviocytes. In one aspect, the nucleic acid delivery vehicle is a virus capsid or a functional part, derivative and/or analogue thereof. Preferably, the virus capsid is an adenovirus capsid. Preferably, the adenovirus is a subgroup B adenovirus, such as adenovirus 16. Preferably, the tissue tropism is provided by at least a tissue tropism determining part of an adenovirus fiber protein or a functional derivative and/or analogue thereof. The invention further presents methods for the treatment of diseases, such as joint related diseases.

7 Claims, 24 Drawing Sheets
(1 of 24 Drawing Sheet(s) Filed in Color)

OTHER PUBLICATIONS

Gall et al., Journal of Virology, 1996, pp. 2116-2123, vol. 70.
Guzman et al., PNAS, 1994, pp. 10732-10736, vol. 91.
Kaye et al., A single amino acid substitution results in a retinoblastoma protein defective in phosphorylation and oncoprotein binding, Sep. 1990, Proc. Natl. Acad. Sci., pp. 6922-6926, vol. 87.
Lazarovits et al., J. Immunol., 1993, pp. 6482-6489, vol. 151.
Lusky et al., Journal of Virology, 1998, pp. 2022-2032, vol. 72.
Makrides et al., Protein Exp. Pur., 1999, pp. 183-202, vol. 17.
Mei et al., Virol., 1998, pp. 254-266, vol. 240.
Miller et al., FASEB J., 1995, pp. 190-199, vol. 9.
Robbins et al., Pharmacol. Ther., 1998, pp. 35-47, vol. 80.
Rudinger et al., Characteristics of the amino acids as components of a peptide hormone sequence, 1976, Peptide Hormones, pp. 1-7.
Russell et al., Nat. Genet., Apr. 1998, pp. 325-330, vol. 18.
Shang et al., J. Immunol., 1998, pp. 467-474, vol. 160.
Stevenson et al., J. Virol., 1997, pp. 4782-4790, vol. 6.
Su, et al., A Genetically Modified Adenoviral Vector Exhibits Enhanced Gene Transfer of Human Smooth Muscle Cells, Journal of Vascular Research 2001, pp. 471-478, vol. 38.
Verma et al., Nature, 1997, pp. 239-242, vol. 389.
Wickham et al., Increased In Vitro and In Vivo Gene Transfer by Adenovirus Vectors Containing Chimeric Fiber Protein, Nov. 1997, Journal of Virology, pp. 8221-8229, vol. 71, No. 11.
Zink et al., Gene Ther. Mol. Biol., Jan. 2001, pp. 1-24, vol. 6.
Hanyuda et al., Activated leucocytes express and secrete macrophage inflammatory protein-1alpha upon interation with synovial fibroblasts of rheumatoid arthritis via a beta2-integrin/ICAM-1 mechanism, Rheumatology, 2003, pp. 1390-1397, vol. 42.
Kitamura et al., Unique Localization of Protein Gene Product 9.5 in Type B Synoviocytes in the Joints of the Horse, The Journal of Histochemistry & Cytochemistry, 1999, pp. 343-351, vol. 47, No. 3.
Firestein, Gary S., Immunologic Mechanisms in the Pathogenesis of Rheumatoid Arthritis, Journal of Clinical Rheumatology, Jun. 2005, pp. S39-S44, vol. 11, No. 3.
Fowler et al., Synovial Metaplasia, A Specialized Form of Repair, Arch Pathol Lab Med, Jun. 2002, pp. 727-730, vol. 126.
Zheng et al., Interleukin-1 receptor antagonist intervenes in signaling between different types of synoviocytes in rats with adjuvant arthritis, Acta Pharmacologica Sinica, Jan. 2006, pp. 111-118, vol. 27, No. 1.
Barland et al., Electron Microscopy of the Human Synovial Membrane, The Journal of Cell Biology, 1962, pp. 207-220, vol. 14.

\* cited by examiner

FIG. 4

ATGAAGCGCGCAAGACCGTCTGAAGATACCTTCAACCCCGTGTATCCATATGAAGATGAAAGCAGCT
CACAACACCCCTTTATAAACCCTGGTTTCATTCCTCAAATGTTTGCACAAAGCCCAGATGGAGT
TCTAACTCTTAAATGTGTTAATCCACTCACTACCGCCAGCGGACCCCTCCAACTTAAAGTTGGAAGC
AGTCTTACAGTAGATACTATCGATGGGTCTTTGGAGAAAATATAACTGCCGAAGCGCCACTCACTA
AAACTAACCACTCCATAGGTTTATTAATAGGATCTGGCTTGCAAACAAAGGATGATAAACTTGTTT
ATCGCTGGGAGATGGGTTGGTAACAAGGATGATAAACTAGTGTTATCGCTGGGAGATGGGTTAATA
ACAAAAATGATGTACTATGTGCCAAACTAGGACATGGCCTTGTGTTTGACTCTTCCAATGCTATCA
CCATAGAAAACAACACCTTGTGGACAGGCGCAAAACCAAGCGCCAACTGTGTAATTAAAGAGGAGA
AGATTCCCCAGACTGTAAGCTCACTTTAGTTCTAGTGAAGAATGGAGGACTGATAAATCAAGTACAATCGATGTAA
ACATTAATGGAGCCTCAGAATATACTGGCCAAATTATTACTTACCTATCATCCCTAAAAGTAACCTGAACTT
ACCTCGCATTGATAATACTGGCCAAATTATTACTTACCTATCATCCCTAAAAGTAACCTGAACTT
TAAAGACAACCAAAACATGGCTACTGGAACCATAACCAGTGCCAAAGGCTTCATGCCCAGCACCACC
GCCTATCCATTTATAACATACGCCACTGAGACCCTAAATGAAGATTACATTTATGGAGAGTGTTACT
ACAAATCTACCAATGGAACTCTCTTCCACTAAAAGTTACTGTCACACTAAACAGACGTATGTTAGC
TTCTGGAATGCCTATGCTATGAATTTTCATGGTCTCTAAATGCAGAGGAAGCCCCGAAACTACC
GAAGTCACTCATTACCTCCCCCCTCTTTTTTTCTTATATCAGAGAAGATGACTGAATGCATTAG (SEQ ID NO:32)

FIG. 7A

Alignment Report of alignment.DNA, using Clustal method with Weighted residue weight table
Wednesday, March 31, 1999 16:13

FIG. 7B

```
600  CATAACATTAATGGGAGCCCTCAGAATATACTAACACCTTGTTTAAAAAACA  Fiber 16 Genbank
600  CATAACATTAATGGGAGCCCTCAGAATATACTAACACCTTGTTTAAAAAACA  Ad5/16 Fiber DNA 650  ATCAAGTTACAAATCGATGTAAAACCTCGCATTTGATAATACTGGCCAAATT  Fiber 16 Genbank
650  ATCAAGTTACAAATCGATGTAAAACCTCGCATTTGATAATACTGGCCAAATT  Ad5/16 Fiber DNA 700  ATTACTTACCCTATCATCCCCTTAAAAGTAAACCTGAACTTTAAACAACCA  Fiber 16 Genbank
700  ATTACTTACCCTATCATCCCCTTAAAAGTAAACCTGAACTTTAAACAACCA  Ad5/16 Fiber DNA 750  AAACATGGCCTACTGGAACCCATAAACCAGTGCCAAAAGGCTTCCAGCA   Fiber 16 Genbank
750  AAACATGGCCTACTGGAACCCATAAACCAGTGCCAAAAGGCTTCCCAGCA  Ad5/16 Fiber DNA 800  CCACCCGCCCTATCCATTTATAACATACGCCACTGAGACCCTAAATGAAGAT  Fiber 16 Genbank
800  CCACCCGCCCTATCCATTTATAACATACGCCACTGAGACCCTAAATGAAGAT  Ad5/16 Fiber DNA 850  TACATTTATGGAGAGTGTTACTACAAATCTACACTCTCTTTCC  Fiber 16 Genbank
850  TACATTTATGGAGAGTGTTACTACAAATCTACACTCTCTTTCC  Ad5/16 Fiber DNA 900  ACTAAAAGTTACTGTCACACACTAAAACAGACGTATGTTAGCCTTCTGGAATGG  Fiber 16 Genbank
900  ACTAAAAGTTACTGTCACACACTAAAACAGACGTATGTTAGCCTTCTGGAATGG  Ad5/16 Fiber DNA 950  CCTATGCTATGAATTTTTTCATGGTCTCTAAAATGCAGAGGAAGCCCCGGAA  Fiber 16 Genbank
950  CCTATGCTATGAATTTTTTCATGGTCTCTAAAATGCAGAGGAAGCCCCGGAA  Ad5/16 Fiber DNA 1000 ACTACCGAAGTCACTCTCTCATTACCCCTTTCTTTTCTTATATCAG  Fiber 16 Genbank
1000 ACTACCGAAGTCACTCTCTCATTACCCCTTTCTTTTCTTATATCAG  Ad5/16 Fiber DNA 1050 AGAAGATGACTGA                                        Fiber 16 Genbank
1050 AGAAGATGACTGAATGCATTAGTTTGTGTTATGTTTCAACGTGTTTATTT   Ad5/16 Fiber DNA 1062                                                     Fiber 16 Genbank
1100 TCAATTG                                             Ad5/16 Fiber DNA
```

Decoration 'Decoration #1': Box residues that differ from Fiber 16 Genbank.

FIG. 7C

Alignment Report of alignment.prot, using Clustal method with PAM250 residue weight table.
Wednesday, March 31, 1999 16:19

```
  1  M A K R A R L S S - S F N P V Y P Y E D E S S S Q H P F I N    genbank Fiber 16      (SEQ ID NO:35)
  1  M - K R A R L S P E D T F N P V Y P Y E D E S S S Q H P F I N    chimeric Ad5/Fib16  (SEQ ID NO:34)

30  P G F I S S N G F A Q S P D G V L T L K C V N P L T T A S G    genbank Fiber 16
 30  P G F I S S N G F A Q S P D G V L T L K C V N P L T T A S G    chimeric Ad5/Fib16

60  P L Q L K V G S S L T V D T I D G S L E E N I T A A A P L T    genbank Fiber 16
 60  P L Q L K V G S S L T V D T I D G S L E E N I T A A A P L T    chimeric Ad5/Fib16

90  K T N H S I G L L I G S G L Q T K D D K L C L S L G D G L V    genbank Fiber 16
 90  K T N H S I G L L I G S G L Q T K D D K L C L S L E D G L V    chimeric Ad5/Fib16

120  T K D D K L C L S L G D G L I T K N D V L C A K L G H G L V    genbank Fiber 16
120  T K D D K L C L S L G D G L I T K N D V L C A K L G H G L V    chimeric Ad5/Fib16

150  F D S S N A I T I E N N T L W T G A K P S A N C V I K E G E    genbank Fiber 16
150  F D S S N A I T I E N N T L W T G A K P S A N C V I K E G E    chimeric Ad5/Fib16

180  D S P D C K L T L V L V K N G G L I N G Y I T L M G A S E Y    genbank Fiber 16
180  D S P D C K L T L V L V K N G G L I N G Y I T L M G A S E Y    chimeric Ad5/Fib16

210  T N T L F K N N Q V T I D V N L A F D N T G Q I H T Y L S S    genbank Fiber 16
210  T N T L F K N N Q V T I D V N L A F D N T G Q I H T Y L S S    chimeric Ad5/Fib16

240  L K S N L N F K D N Q N M A T G T H I T S A K G F M P S T T A    genbank Fiber 16
240  L K S N L N F K D N Q N M A T G T H I T S A K G F M P S T T A    chimeric Ad5/Fib16

270  Y P F I T Y A T E T L N E D Y I H Y G E C Y Y K S T N G T L F    genbank Fiber 16
270  Y P F I T Y A T E T L N E D Y I H Y G E C Y Y K S T N G T L F    chimeric Ad5/Fib16

300  P L K V T V T L N R R M L A S G M A Y A M N F S W S L N A E    genbank Fiber 16
300  P L K V T V T L N R R M L A S G M A Y A M N F S W S L N A E    chimeric Ad5/Fib16

330  E A P E T T E V T L I T S P F F F S Y I R E D D    genbank Fiber 16
330  E A P E T T E V T L I T S P F F F S Y I R E D D    chimeric Ad5/Fib16
```

Decoration 'Decoration #1': Box residues that differ from genbank Fiber 16.

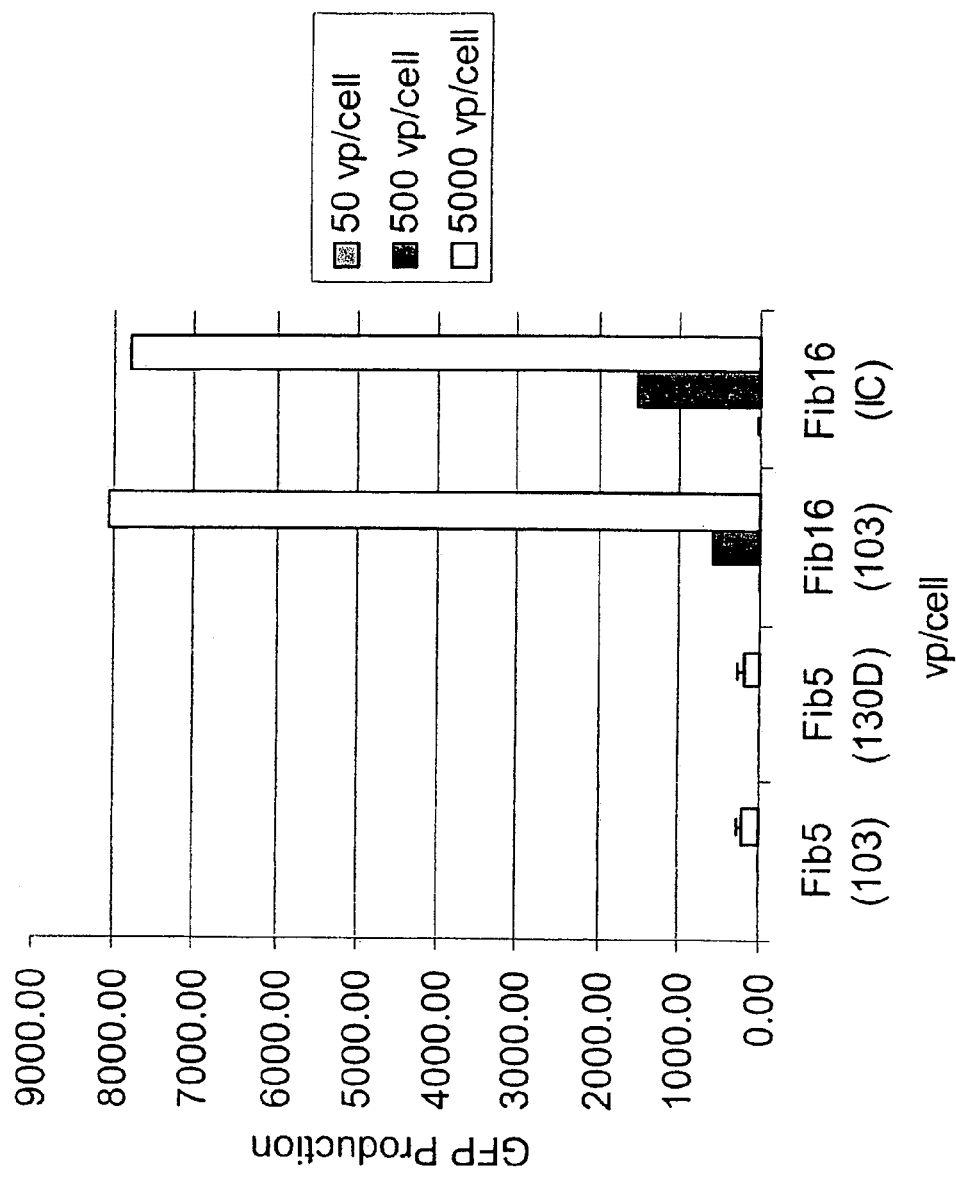

SEQUENCE LISTING

```
<160> NUMBER OF SEQ ID NOS: 38

<210> SEQ ID NO 1
<211> LENGTH: 23
<212> TYPE: DNA
<213> ORGANISM: Artificial Sequence
<220> FEATURE:
<223> OTHER INFORMATION: Chemically synthesized Primer HSA-2

<400> SEQUENCE: 1
aattgtctta attaaccgct taa                                             23

<210> SEQ ID NO 2
<211> LENGTH: 19
<212> TYPE: DNA
<213> ORGANISM: Artificial Sequence
<220> FEATURE:
```

-continued

```
<223> OTHER INFORMATION: Chemically synthesized Primer HSA-2

<400> SEQUENCE: 2
aattgtctta attaaccgc                                              19

<210> SEQ ID NO 3
<211> LENGTH: 19
<212> TYPE: DNA
<213> ORGANISM: Artificial Sequence
<220> FEATURE:
<223> OTHER INFORMATION: Chemically synthesized Primer HSA-2

<400> SEQUENCE: 3
aattgcggtt aattaagac                                              19

<210> SEQ ID NO 4
<211> LENGTH: 27
<212> TYPE: DNA
<213> ORGANISM: Artificial Sequence
<220> FEATURE:
<223> OTHER INFORMATION: Chemically synthesized Primer HSA-2

<400> SEQUENCE: 4
gggggatccg aacttgttta ttgcagc                                     27

<210> SEQ ID NO 5
<211> LENGTH: 25
<212> TYPE: DNA
<213> ORGANISM: Artificial Sequence
<220> FEATURE:
<223> OTHER INFORMATION: Chemically synthesized Primer HSA-2

<400> SEQUENCE: 5
gggagatcta gacatgataa gatac                                       25

<210> SEQ ID NO 6
<211> LENGTH: 27
<212> TYPE: DNA
<213> ORGANISM: Artificial Sequence
<220> FEATURE:
<223> OTHER INFORMATION: Chemically synthesized Primer HSA-2

<400> SEQUENCE: 6
gggagatctg tactgaaatg tgtgggc                                     27

<210> SEQ ID NO 7
<211> LENGTH: 24
<212> TYPE: DNA
<213> ORGANISM: Artificial Sequence
<220> FEATURE:
<223> OTHER INFORMATION: Chemically synthesized Primer HSA-2

<400> SEQUENCE: 7
ggaggctgca gtctccaacg gcgt                                        24

<210> SEQ ID NO 8
<211> LENGTH: 47
<212> TYPE: DNA
<213> ORGANISM: Artificial Sequence
<220> FEATURE:
<223> OTHER INFORMATION: Chemically synthesized Primer HSA-2

<400> SEQUENCE: 8
ctgtacgtac cagtgcactg gcctaggcat ggaaaaatac ataactg                47
```

<210> SEQ ID NO 9
<211> LENGTH: 64
<212> TYPE: DNA
<213> ORGANISM: Artificial Sequence
<220> FEATURE:
<223> OTHER INFORMATION: Chemically synthesized Primer HSA-2

<400> SEQUENCE: 9
gcggatcctt cgaaccatgg taagcttggt accgctagcg ttaaccgggc gactcagtca    60
atcg                                                                64

<210> SEQ ID NO 10
<211> LENGTH: 28
<212> TYPE: DNA
<213> ORGANISM: Artificial Sequence
<220> FEATURE:
<223> OTHER INFORMATION: Chemically synthesized Primer HSA-2

<400> SEQUENCE: 10
gcgccaccat gggcagagcg atggtggc                                      28

<210> SEQ ID NO 11
<211> LENGTH: 47
<212> TYPE: DNA
<213> ORGANISM: Artificial Sequence
<220> FEATURE:
<223> OTHER INFORMATION: Chemically synthesized Primer HSA-2

<400> SEQUENCE: 11
ctgtacgtac cagtgcactg gcctaggcat ggaaaaatac ataactg                 47

<210> SEQ ID NO 12
<211> LENGTH: 64
<212> TYPE: DNA
<213> ORGANISM: Artificial Sequence
<220> FEATURE:
<223> OTHER INFORMATION: Chemically synthesized Primer HSA-2

<400> SEQUENCE: 12
gcggatcctt cgaaccatgg taagcttggt accgctagcg ttaaccgggc gactcagtca    60
atcg                                                                64

<210> SEQ ID NO 13
<211> LENGTH: 50
<212> TYPE: DNA
<213> ORGANISM: Artificial Sequence
<220> FEATURE:
<223> OTHER INFORMATION: Chemically synthesized Primer HSA-2

<400> SEQUENCE: 13
gttagatcta agcttgtcga catcgatcta ctaacagtag agatgtagaa              50

<210> SEQ ID NO 14
<211> LENGTH: 47
<212> TYPE: DNA
<213> ORGANISM: Artificial Sequence
<220> FEATURE:
<223> OTHER INFORMATION: Chemically synthesized Primer HSA-2

<400> SEQUENCE: 14
ctgtacgtac cagtgcactg gcctaggcat ggaaaaatac ataactg                 47

<210> SEQ ID NO 15
<211> LENGTH: 64
<212> TYPE: DNA

<213> ORGANISM: Artificial Sequence
<220> FEATURE:
<223> OTHER INFORMATION: Chemically synthesized Primer LTR-2

<400> SEQUENCE: 15
gcggatcctt cgaaccatgg taagcttggt accgctagcg ttaaccgggc gactcagtca    60
atcg    64

<210> SEQ ID NO 16
<211> LENGTH: 10
<212> TYPE: DNA
<213> ORGANISM: Artificial Sequence
<220> FEATURE:
<223> OTHER INFORMATION: Chemically synthesized Primer

<400> SEQUENCE: 16
ttaagtcgac    10

<210> SEQ ID NO 17
<211> LENGTH: 32
<212> TYPE: DNA
<213> ORGANISM: Artificial Sequence
<220> FEATURE:
<223> OTHER INFORMATION: Chemically synthesized Primer

<400> SEQUENCE: 17
ggggtggcca gggtacctct aggcttttgc aa    32

<210> SEQ ID NO 18
<211> LENGTH: 29
<212> TYPE: DNA
<213> ORGANISM: Artificial Sequence
<220> FEATURE:
<223> OTHER INFORMATION: Chemically synthesized Primer

<400> SEQUENCE: 18 gggggatcc ataaacaagt tcagaatcc    29

<210> SEQ ID NO 19
<211> LENGTH: 35
<212> TYPE: DNA
<213> ORGANISM: Artificial Sequence
<220> FEATURE:
<223> OTHER INFORMATION: Chemically synthesized oligonucleotide for
      amplification of DNA encoding fiber protein
      derived from adenovirus serotype

<400> SEQUENCE: 19
cccgtgtatc catatgatgc agacaacgac cgacc    35

<210> SEQ ID NO 20
<211> LENGTH: 27
<212> TYPE: DNA
<213> ORGANISM: Artificial Sequence
<220> FEATURE:
<223> OTHER INFORMATION: Chemically synthesized oligonucleotide for
      amplification of DNA encoding fiber protein
      derived from adenovirus serotype

<400> SEQUENCE: 20
cccgtctacc catatggcta cgcgcgg    27

<210> SEQ ID NO 21
<211> LENGTH: 27
<212> TYPE: DNA
<213> ORGANISM: Artificial Sequence

```
<220> FEATURE:
<223> OTHER INFORMATION: Chemically synthesized oligonucleotide for
                        amplification of DNA encoding fiber protein
                        derived from adenovirus serotype

<400> SEQUENCE: 21
cckgtstacc catatgaaga tgaaagc                                              27

<210> SEQ ID NO 22
<211> LENGTH: 31
<212> TYPE: DNA
<213> ORGANISM: Artificial Sequence
<220> FEATURE:
<223> OTHER INFORMATION: Chemically synthesized oligonucleotide for
                        amplification of DNA encoding fiber protein
                        derived from adenovirus serotype

<400> SEQUENCE: 22
cccgtctacc catatgacac ctyctcaact c                                         31

<210> SEQ ID NO 23
<211> LENGTH: 36
<212> TYPE: DNA
<213> ORGANISM: Artificial Sequence
<220> FEATURE:
<223> OTHER INFORMATION: Chemically synthesized oligonucleotide for
                        amplification of DNA encoding fiber protein
                        derived from adenovirus serotype

<400> SEQUENCE: 23
cccgtttacc catatgaccc atttgacaca tcagac                                    36

<210> SEQ ID NO 24
<211> LENGTH: 30
<212> TYPE: DNA
<213> ORGANISM: Artificial Sequence
<220> FEATURE:
<223> OTHER INFORMATION: Chemically synthesized oligonucleotide for
                        amplification of DNA encoding fiber protein
                        derived from adenovirus serotype

<400> SEQUENCE: 24
ccgatgcatt tattgttggg ctatatagga                                           30

<210> SEQ ID NO 25
<211> LENGTH: 30
<212> TYPE: DNA
<213> ORGANISM: Artificial Sequence
<220> FEATURE:
<223> OTHER INFORMATION: Chemically synthesized oligonucleotide for
                        amplification of DNA encoding fiber protein
                        derived from adenovirus serotype

<400> SEQUENCE: 25
ccgatgcatt yattcttggg cratatagga                                           30

<210> SEQ ID NO 26
<211> LENGTH: 36
<212> TYPE: DNA
<213> ORGANISM: Artificial Sequence
<220> FEATURE:
<223> OTHER INFORMATION: Chemically synthesized oligonucleotide for
                        amplification of DNA encoding fiber protein
                        derived from adenovirus serotype

<400> SEQUENCE: 26
ccgatgcatt tattcttggg raatgtawga aaagga                                    36
```

<210> SEQ ID NO 27
<211> LENGTH: 30
<212> TYPE: DNA
<213> ORGANISM: Artificial Sequence
<220> FEATURE:
<223> OTHER INFORMATION: Chemically synthesized oligonucleotide for
amplification of DNA encoding fiber protein
derived from adenovirus serotype

<400> SEQUENCE: 27
ccgatgcatt cagtcatctt ctctgatata              30

<210> SEQ ID NO 28
<211> LENGTH: 30
<212> TYPE: DNA
<213> ORGANISM: Artificial Sequence
<220> FEATURE:
<223> OTHER INFORMATION: Chemically synthesized oligonucleotide for
amplification of DNA encoding fiber protein
derived from adenovirus serotype

<400> SEQUENCE: 28
ccgatgcatt tattgttcag ttatgtagca              30

<210> SEQ ID NO 29
<211> LENGTH: 30
<212> TYPE: DNA
<213> ORGANISM: Artificial Sequence
<220> FEATURE:
<223> OTHER INFORMATION: Chemically synthesized oligonucleotide for
amplification of DNA encoding fiber protein
derived from adenovirus serotype

<400> SEQUENCE: 29
gccatgcatt tattgttctg ttacataaga              30

<210> SEQ ID NO 30
<211> LENGTH: 37
<212> TYPE: DNA
<213> ORGANISM: Artificial Sequence
<220> FEATURE:
<223> OTHER INFORMATION: Chemically synthesized oligonucleotide for
amplification of DNA encoding fiber protein
derived from adenovirus serotype

<400> SEQUENCE: 30
ccgttaatta agcccttatt gttctgttac ataagaa              37

<210> SEQ ID NO 31
<211> LENGTH: 30
<212> TYPE: DNA
<213> ORGANISM: Artificial Sequence
<220> FEATURE:
<223> OTHER INFORMATION: Chemically synthesized oligonucleotide for
amplification of DNA encoding fiber protein
derived from adenovirus serotype

<400> SEQUENCE: 31
ccgatgcatt cagtcatcyt ctwtaatata              30

<210> SEQ ID NO 32
<211> LENGTH: 1068
<212> TYPE: DNA
<213> ORGANISM: Artificial sequence
<220> FEATURE:
<223> OTHER INFORMATION: DNA encoding Adenovirus Ad5/fib16 chimeric
fiber

```
<400> SEQUENCE: 32
atgaagcgcg caagaccgtc tgaagatacc ttcaaccccg tgtatccata tgaagatgaa      60
agcagctcac aacacccctt tataaaccct ggtttcattt cctcaaatgg ttttgcacaa     120
agcccagatg gagttctaac tcttaaatgt gttaatccac tcactaccgc cagcggaccc     180
ctccaactta aagttggaag cagtcttaca gtagatacta tcgatgggtc tttggaggaa     240
aatataactg ccgaagcgcc actcactaaa ctaaccactc cataggttta ttaataggat     300
ctggcttgca aacaaggat gataaacttt gtttatcgct gggagatggg ttggtaacaa      360
aggatgataa actatgttta tcgctgggag atgggttaat aacaaaaaat gatgtactat     420
gtgccaaact aggacatggc cttgtgtttg actcttccaa tgctatcacc atagaaaaca     480
acaccttgtg gacaggcgca aaaccaagcg ccaactgtgt aattaaagag ggagaagatt     540
ccccagactg taagctcact ttagttctag tgaagaatgg aggactgata aatggataca     600
taacattaat gggagcctca gaatatacta acaccttgtt taaacaatc aagttacaat      660 cgatgtaaac ctcgcatttg ataatactgg ccaaattatt acttacctat catcccttaa     720
aagtaacctg aactttaaag acaaccaaaa catggctact ggaaccataa ccagtgccaa     780
aggcttcatg cccagcacca ccgcctatcc atttataaca tacgccactg agaccctaaa     840
tgaagattac atttatggag agtgttacta caaatctacc aatggaactc tctttccact     900
aaaagttact gtcacactaa acagacgtat gttagcttct ggaatggcct atgctatgat     960
ttttcatggt ctctaaatgc agaggaagcc ccggaaacta ccgaagtcac tctcattacc    1020 tccccttct ttttttctta tatcagagaa gatgactgaa tgcattag                  1068

<210> SEQ ID NO 33
<211> LENGTH: 1062
<212> TYPE: DNA
<213> ORGANISM: Adenovirus 16

<400> SEQUENCE: 33
atggccaaac gagctcggct aagcagctcc ttcaatccgg tctaccccta tgaagatgaa      60
agcagctcac aacacccctt tataaaccct ggtttcattt cctcaaatgg ttttgcacaa     120
agcccagatg gagttctaac tcttaaatgt gttaatccac tcactaccgc cagcggaccc     180
ctccaactta aagttggaag cagtcttaca gtagatacta tcgatgggtc tttggaggaa     240
aatataactg ccgcagcgcc actcactaaa actaaccact ccataggttt attaatagga     300
tctggcttgc aaacaaagga tgataaactt tgtttatcgc tgggagatgg gttggtaaca     360
aaggatgata actatgtttt atcgctggga gatgggttaa taacaaaaaa tgatgtacta     420
tgtgccaaac taggacatgg ccttgtgttt gactcttcca atgctatcac catagaaaac     480
aacaccttgt ggacaggcgc aaaaccaagc gccaactgtg taattaaaga gggagaagat     540
tccccagact gtaagctcac tttagttcta gtgaagaatg gaggactgat aaatggatac     600
ataacattaa tgggagcctc agaatatact aacaccttgt ttaaaacaa tcaagttaca     660 atcgatgtaa acctcgcatt tgataatact ggccaaatta ttacttacct atcatccctt     720
aaaagtaacc tgaactttaa agacaaccaa acatggctac tggaaccat aaccagtgcc      780 aaaggcttca tgcccagcac caccgcctat ccatttataca tacgccac tgagaccct      840 aatgaagatt acatttatgg agagtgttac taaatctaa ccaatggaac tctctttcca      900
ctaaaagtta ctgtcacact aaacagacgt atgttagctt ctggaatggc ctatgctatg     960 aattttttcat ggtctctaaa tgcagaggaa gccccggaaa ctaccgaagt cactctcatt    1020
```
acctccccct tcttttttc ttatatcaga gaagatgact ga         1062

<210> SEQ ID NO 34
<211> LENGTH: 353
<212> TYPE: PRT
<213> ORGANISM: Artificial sequence
<220> FEATURE:
<223> OTHER INFORMATION: Chimeric Ad5/Fib16 protein

<400> SEQUENCE: 34

```
Met Lys Arg Ala Arg Pro Ser Glu Asp Thr Phe Asn Pro Val Tyr Pro
1               5                   10                  15

Tyr Glu Asp Glu Ser Ser Ser Gln His Pro Phe Ile Asn Pro Gly Phe
            20                  25                  30

Ile Ser Ser Asn Gly Phe Ala Gln Ser Pro Asp Gly Val Leu Thr Leu
        35                  40                  45

Lys Cys Val Asn Pro Leu Thr Thr Ala Ser Gly Pro Leu Gln Leu Lys
    50                  55                  60

Val Gly Ser Ser Leu Thr Val Asp Thr Ile Asp Gly Ser Leu Glu Glu
65                  70                  75                  80

Asn Ile Thr Ala Ala Ala Pro Leu Thr Lys Thr Asn His Ser Ile Gly
                85                  90                  95

Leu Leu Ile Gly Ser Gly Leu Gln Thr Lys Asp Lys Leu Cys Leu
            100                 105                 110

Ser Leu Glu Asp Gly Leu Val Thr Lys Asp Lys Leu Cys Leu Ser
        115                 120                 125

Leu Gly Asp Gly Leu Ile Thr Lys Asn Asp Val Leu Cys Ala Lys Leu
    130                 135                 140

Gly His Gly Leu Val Phe Asp Ser Ser Asn Ala Ile Thr Ile Glu Asn
145                 150                 155                 160

Asn Thr Leu Trp Thr Gly Ala Lys Pro Ser Ala Asn Cys Val Ile Lys
                165                 170                 175

Glu Gly Glu Asp Ser Pro Asp Cys Lys Leu Thr Leu Val Leu Val Lys
            180                 185                 190

Asn Gly Gly Leu Ile Asn Gly Tyr Ile Thr Leu Met Gly Ala Ser Glu
        195                 200                 205

Tyr Thr Asn Thr Leu Phe Lys Asn Asn Gln Val Thr Ile Asp Val Asn
    210                 215                 220

Leu Ala Phe Asp Asn Thr Gly Gln Ile Ile Thr Tyr Leu Ser Ser Leu
225                 230                 235                 240

Lys Ser Asn Leu Asn Phe Lys Asp Asn Gln Asn Met Ala Thr Gly Thr
                245                 250                 255

Ile Thr Ser Ala Lys Gly Phe Met Pro Ser Thr Thr Ala Tyr Pro Phe
            260                 265                 270

Ile Thr Tyr Ala Thr Glu Thr Leu Asn Glu Asp Tyr Ile Tyr Gly Glu
        275                 280                 285

Cys Tyr Tyr Lys Ser Thr Asn Gly Thr Leu Phe Pro Leu Lys Val Thr
    290                 295                 300

Val Thr Leu Asn Arg Arg Met Leu Ala Ser Gly Met Ala Tyr Ala Met
305                 310                 315                 320

Asn Phe Ser Trp Ser Leu Asn Ala Glu Glu Ala Pro Glu Thr Thr Glu
                325                 330                 335

Val Thr Leu Ile Thr Ser Pro Phe Phe Phe Ser Tyr Ile Arg Glu Asp
            340                 345                 350
```

-continued

Asp

<210> SEQ ID NO 35
<211> LENGTH: 353
<212> TYPE: PRT
<213> ORGANISM: Adenovirus Ad16

<400> SEQUENCE: 35

```
Met Ala Lys Arg Ala Arg Leu Ser Ser Phe Asn Pro Val Tyr Pro
1               5                   10                  15

Tyr Glu Asp Glu Ser Ser Gln His Pro Phe Ile Asn Pro Gly Phe
                20                  25                  30

Ile Ser Ser Asn Gly Phe Ala Gln Ser Pro Asp Gly Val Leu Thr Leu
                35                  40                  45

Lys Cys Val Asn Pro Leu Thr Ala Ser Gly Pro Leu Gln Leu Lys
    50                  55                  60

Val Gly Ser Ser Leu Thr Val Asp Thr Ile Asp Gly Ser Leu Glu Glu
65                  70                  75                  80

Asn Ile Thr Ala Ala Pro Leu Thr Lys Thr Asn His Ser Ile Gly
                85                  90                  95

Leu Leu Ile Gly Ser Gly Leu Gln Thr Lys Asp Asp Lys Leu Cys Leu
                100                 105                 110

Ser Leu Gly Asp Gly Leu Val Thr Lys Asp Asp Lys Leu Cys Leu Ser
                115                 120                 125

Leu Gly Asp Gly Leu Ile Thr Lys Asn Asp Val Leu Cys Ala Lys Leu
                130                 135                 140

Gly His Gly Leu Val Phe Asp Ser Ser Asn Ala Ile Thr Ile Glu Asn
145                 150                 155                 160

Asn Thr Leu Trp Thr Gly Ala Lys Pro Ser Ala Asn Cys Val Ile Lys
                165                 170                 175

Glu Gly Glu Asp Ser Pro Asp Cys Lys Leu Thr Leu Val Leu Val Lys
                180                 185                 190

Asn Gly Gly Leu Ile Asn Gly Tyr Ile Thr Leu Met Gly Ala Ser Glu
                195                 200                 205

Tyr Thr Asn Thr Leu Phe Lys Asn Asn Gln Val Thr Ile Asp Val Asn
    210                 215                 220

Leu Ala Phe Asp Asn Thr Gly Gln Ile Ile Thr Tyr Leu Ser Ser Leu
225                 230                 235                 240

Lys Ser Asn Leu Asn Phe Lys Asp Asn Gln Asn Met Ala Thr Gly Thr
                245                 250                 255

Ile Thr Ser Ala Lys Gly Phe Met Pro Ser Thr Thr Ala Tyr Pro Phe
                260                 265                 270

Ile Thr Tyr Ala Thr Glu Thr Leu Asn Glu Asp Tyr Ile Tyr Gly Glu
                275                 280                 285

Cys Tyr Tyr Lys Ser Thr Asn Gly Thr Leu Phe Pro Leu Lys Val Thr
    290                 295                 300

Val Thr Leu Asn Arg Arg Met Leu Ala Ser Gly Met Ala Tyr Ala Met
305                 310                 315                 320

Asn Phe Ser Trp Ser Leu Asn Ala Glu Glu Ala Pro Glu Thr Thr Glu
                325                 330                 335

Val Thr Leu Ile Thr Ser Pro Phe Phe Phe Ser Tyr Ile Arg Glu Asp
                340                 345                 350

Asp
```

-continued

```
<210> SEQ ID NO 36
<211> LENGTH: 42
<212> TYPE: DNA
<213> ORGANISM: Artificial Sequence
<220> FEATURE:
<223> OTHER INFORMATION: Chemically synthesized Primer NY-UP

<400> SEQUENCE: 36
cgacatatgt agatgcatta gtttgtgtta tgtttcaacg tg                        42

<210> SEQ ID NO 37
<211> LENGTH: 19
<212> TYPE: DNA
<213> ORGANISM: Artificial Sequence
<220> FEATURE:
<223> OTHER INFORMATION: Chemically synthesized Primer NY-DOWN

<400> SEQUENCE: 37
ggagaccact gccatgttg                                                  19

<210> SEQ ID NO 38
<211> LENGTH: 1103
<212> TYPE: DNA
<213> ORGANISM: Artificial sequence
<220> FEATURE:
<223> OTHER INFORMATION: DNA encoding Adenovirus Ad5/fib16 chimeric
                        fiber

<400> SEQUENCE: 38
atgaagcgcg caagaccgtc tgaagatacc ttcaaccccg tgtatccata tgaagatgaa       60
agcagctcac aacacccctt tataaaccct ggtttcattt cctcaaatgg ttttgcacaa      120
agcccagatg gagttctaac tcttaaatgt gttaatccac tcactaccgc cagcggaccc      180
ctccaactta aagttggaag cagtcttaca gtagatacta tcgatgggtc tttggaggaa      240
aatataactg ccgaagcgcc actcactaaa ctaaccactc cataggttta ttaataggat      300
ctggcttgca aacaaaggat gataaacttt gtttatcgct gggagatggg ttggtaacaa      360
aggatgataa actatgttta tcgctgggag atgggttaat aacaaaaaat gatgtactat      420
gtgccaaact aggacatggc cttgtgtttg actcttccaa tgctatcacc atagaaaaca      480
acaccttgtg gacaggcgca aaaccaagcg ccaactgtgt aattaaagag ggagaagatt      540
ccccagactg taagctcact ttagttctag tgaagaatgg aggactgata aatggataca      600
taacattaat gggagcctca gaatatacta acaccttgtt taaaacaatc aagttacaat      660
cgatgtaaac ctcgcatttg ataatactgg ccaaattatt acttacctat catcccttaa      720
aagtaacctg aactttaaag acaaccaaaa catggctact ggaaccataa ccagtgccaa      780
aggcttcatg cccagcacca ccgcctatcc atttataaca tacgccactg agaccctaaa      840
tgaagattac atttatggag agtgttacta caaatctacc aatggaactc tctttccact      900
aaaagttact gtcacactaa acagacgtat gttagcttct ggaatggcct atgctatgat      960 tttcatggt ctctaaatgc agaggaagcc ccggaaacta ccgaagtcac tctcattacc     1020
tcccccttct tttttctta tatcagagaa gatgactgaa tgcattagtt tgtgttatgt     1080
ttcaacgtgt ttatttcaa ttg                                             1103
```

MEANS AND METHODS FOR FIBROBLAST-LIKE OR MACROPHAGE-LIKE CELL TRANSDUCTION

CROSS-REFERENCE TO RELATED APPLICATIONS

This application is a continuation of application Ser. No. 09/517,898, filed Mar. 3, 2000, U.S. Pat. No. 6,869,936 which under the provisions of 35 U.S.C. § 119(e), claimed priority from U.S. Provisional Patent Application 60/122,732 filed Mar. 4, 1999 and U.S. Provisional Patent Application 60/123,061 filed on Mar. 5, 1999, the contents of all of which are incorporated by this reference.

TECHNICAL FIELD

The invention relates generally to biotechnology, particularly recombinant DNA technology. More particularly, the invention relates to means and methods for transferring nucleic acid into fibroblast-like or macrophage-like cells, such as synoviocytes. The invention further relates to means and methods for the treatment of diseases by at least transferring nucleic acid into fibroblast-like or macrophage-like cells, again preferably synoviocytes, for instance, for the treatment of rheumatoid arthritis ("RA").

BACKGROUND

Efficient delivery of foreign genetic material to fibroblast-like or macrophage-like cells, especially synoviocytes, has proven to be a difficult goal to achieve. Even with the currently developed viral vectors that are, in general, very effective in delivering foreign genetic material to cells, fibroblast-like or macrophage-like cells have been difficult to provide with foreign genetic material. The relative inefficient transduction of these cells, especially of synoviocytes, has hampered the development of therapeutic approaches based on nucleic acid transfer to these cells.

As a result of the inefficient delivery of nucleic acid into, for example, synoviocytes, therapeutic approaches based on nucleic acid transfer involving these cells have focused on strategies in which a low transduction efficiency could at least in part be tolerated. For instance, by relying on delivering nucleic acid encoding proteins with so-called bystander effect, i.e., the expression in a transduced cell of which affects the function of un-transduced cells in the vicinity of transduced cells. Non-limiting examples of proteins with bystander effect are, for instance, excreted factors and/or suicide gene expression such as herpes simplex virus ("HSV") thymidine kinase ("TK") expression which in the presence of gancyclovir leads to production of toxic metabolites. The HSV TK-gene encodes a protein capable of metabolizing the relatively non-toxic anti-viral drug gancyclovir ("GCV") into a mono-phosphorylated product. Subsequent phosphorylation by mammalian kinases results in a tri-phosphorylated nucleoside analogue ("GCV-PPP") that inhibits DNA-polymerase and kills cells, probably through apoptosis (Vincent et al., 1996).

Although the use of a bystander effect may, in part, reduce the requirement for efficient transduction of fibroblast-like or macrophage-like cells, a more efficient method of transferring genetic material nevertheless is still desirable for economic and safety reasons. Safety aspects include, for instance, the relative sensitivity of liver cells towards toxicity of HSV-TK based cell kill. When cells, other than liver cells, form the target population for suicide by HSV-TK, liver cell transduction should be prevented as much as possible. Unintended liver cell transduction can occur, for instance, through leakage of a nucleic acid delivery vehicle from the site of delivery into the blood stream from where it is transported to the liver. This leakage is dependent on, among other things, the amount of nucleic acid delivery vehicle used. Thus, when, for instance, synoviocytes form the target cells, a certain amount of nucleic acid delivery vehicle will be needed for obtaining a desired level of transduction. When less nucleic acid delivery vehicle is used, leakage of nucleic acid delivery vehicle is less of a problem.

Non-limiting examples in which nucleic acid transfer to fibroblast-like or macrophage-like cells would be beneficial are chronic erosive joint diseases like rheumatoid arthritis, ankylosing spondylitis, and juvenile chronic arthritis. A favorable target cell for nucleic acid transfer in these diseases is the synoviocyte. However, with current methods, the efficiency of transduction of such cells leaves much to be desired.

In a diarthrodial movable joint, smooth articulation is ensured by the unique macromolecular structure of articular cartilage, which covers the end of the bones. The articular cartilages move against one another within a cavity, the joint space, which is lined by a tissue called the synovium. The synovium consists of macrophage-like type A cells and fibroblast-like type B cells, and is underlain by a sparsely cellular subsynovium which, depending on anatomical localization, may be fibrous, adipose or areolar in nature. The fibroblast-like synoviocytes ("FLS") are distinguishable from normal fibroblast cells in the subintimal synovium by differential gene expression patterns. FLS have been shown to express high levels of uridine diphosphoglucose dehydrogenase ("UDPGD"), high levels of vascular cell adhesion molecule-1 ("VCAM-1"), intercellular adhesion molecule-1 ("ICAM-1") as well as CD44 (hyaluronic acid receptor), fibronectin receptor and β-integrins. Sublining fibroblasts or fibroblasts from other sources do not, or at a lower level, express these markers (reviewed by J. C. W. Edwards, 1995; G. S. Firestein, 1996).

Rheumatoid arthritis is characterized by massive hyperplasia of the synovium and the presence of inflammatory cells (lymphocytes, macrophages and mast cells) in and around the synovial tissue. Both the FLS and the type A macrophage-like cells play an important role in the destructive aspects of the disease. The type A cells constitute the majority of the cells in normal intima and hyperplastic RA tissue. The highly invasive FLS exhibits histological features usually associated with immature tumour like fibroblasts (Qu et al., 1994; Firestein 1996). Proliferation of these synovial cells leads to pannus tissue which invades and overgrows the cartilage, leading to bone destruction (Zvaifler and Firestein, 1994). Removal of the diseased synovium is beneficial by decreasing inflammation and by preventing destruction of the proliferating pannus in adjacent structures (Thompson et al., 1973). Specific removal of this proliferating pannus tissue by a simple, non-destructive local procedure, suitable for all joints and rather specific for cells that are proliferating, is a valuable treatment for RA. (Nakamura et al., 1997; Cruz-Esteban and Wilke, 1995).

Gene therapy is a promising treatment modality for RA. Nucleic acid transfer to rheumatoid synovial tissue may result either in the production of mediators that inhibit inflammation or hyperplasia or may result in toxic substances that destroy specifically the synovium. The first clinical trials in humans were based on ex-vivo transduction of synoviocytes with IL1-RA, in order to inhibit inflammation (Evans, 1996).

The present invention was made in the course of the manipulation of adenovirus vectors. In the following section, therefore, adenoviruses are discussed.

Adenoviruses

Adenoviruses contain a linear double-stranded DNA molecule of approximately 36,000 base pairs ("bp"). It contains identical Inverted Terminal Repeats ("ITRs") of approximately 90–140 bp, with the exact length dependent on the serotype. The viral origins of replication are within the ITRs exactly at the genome ends. The transcription units are divided in early and late regions. Shortly after infection, the E1A and E1B proteins are expressed, and function in transactivation of cellular and adenoviral genes. The early regions E2A and E2B encode proteins (DNA binding protein, pre-terminal protein and polymerase) required for the replication of the adenoviral genome (reviewed in van der Vliet, 1995). The early region E4 encodes several proteins with pleiotropic functions, for example, transactivation of the E2 early promoter, facilitating transport and accumulation of viral mRNAs in the late phase of infection and increasing nuclear stability of major late pre-mRNAs (reviewed in Leppard, 1997). The early region 3 encodes proteins that are involved in modulation of the immune response of the host (Wold et al., 1995). The late region is transcribed from one single promoter (major late promoter) and is activated at the onset of DNA replication. Complex splicing and poly-adenylation mechanisms give rise to more than 12 RNA species coding for core proteins, capsid proteins (penton, hexon, fiber and associated proteins), viral protease and proteins necessary for the assembly of the capsid and shut-down of host protein translation (Imperiale, M. J., Akusjnarvi, G. and Leppard, K. N. (1995) Post-transcriptional control of adenovirus gene expression. In: The molecular repertoire of adenoviruses I. P 139–171. W. Doerfler and P. Bohm (eds.), Springer-Verlag Berlin Heidelberg).

Interaction between Virus and Host Cell

The interaction of the virus with the host cell has mainly been investigated with the serotype C viruses Ad2 and Ad5. Binding occurs via interaction of the knob region of the protruding fiber with a cellular receptor. The receptor for Ad2 and Ad5 and probably more adenoviruses is known as the 'Coxsackievirus and Adenovirus Receptor' or CAR protein (Bergelson et al., 1997). Internalization is mediated through interaction of the RGD sequence present in the penton base with cellular integrins (Wickham et al., 1993). This may not be true for all serotypes, for example, serotype 40 and 41 do not contain a RGD sequence in their penton base sequence (Kidd et al., 1993).

The Fiber Protein

The initial step for successful infection is the binding of adenovirus to its target cell, a process mediated through fiber protein. The fiber protein has a trimeric structure (Stouten et al., 1992) with different lengths depending on the virus serotype (Signas et al., 1985; Kidd et al., 1993). Different serotypes have polypeptides with structurally similar N and C termini, but different middle stem regions. The first 30 amino acids at the N terminus are involved in anchoring of the fiber to the penton base (Chroboczek et al., 1995), especially the conserved FNPVYP (SEQ ID NO:39) region in the tail (Arnberg et al., 1997). The C-terminus, or "knob", is responsible for initial interaction with the cellular adenovirus receptor. After this initial binding, secondary binding between the capsid penton base and cell-surface integrins leads to internalization of viral particles in coated pits and endocytosis (Morgan et al., 1969; Svensson and Persson, 1984; Varga et al., 1991; Greber et al., 1993; Wickham et al., 1993). Integrins are ab-heterodimers of which at least 14 a-subunits and 8 β-subunits have been identified (Hynes, 1992). The array of integrins expressed in cells is complex and will vary between cell types and cellular environment. Although the knob contains some conserved regions between serotypes, knob proteins show a high degree of variability, indicating that different adenovirus receptors exist.

Adenoviral Serotypes

At present, six different subgroups of human adenoviruses have been proposed, which in total encompass approximately 50 distinct adenovirus serotypes. Besides these human adenoviruses, many animal adenoviruses have been identified. (See, e.g., Ishibashi and Yasue, 1984).

A serotype is defined on the basis of its immunological distinctiveness as determined by quantitative neutralization with animal antisera (e.g., horse, rabbit). If neutralization shows a certain degree of cross-reactivity between two viruses, distinctiveness of serotype is assumed if A) the hemagglutinins are unrelated, as shown by lack of cross-reaction on hemagglutination-inhibition, or B) substantial biophysical/biochemical differences in DNA exist (Francki et al., 1991). The serotypes identified last (nos. 42–49) were isolated for the first time from HIV infected patients (Hierholzer et al., 1988; Schnurr et al., 1993). For reasons not well understood, most of such immuno-compromised patients shed adenoviruses that were never isolated from immuno-competent individuals (Hierholzer et al., 1988, 1992; Khoo et al., 1995).

Besides differences towards the sensitivity against neutralizing antibodies of different adenovirus serotypes, adenoviruses in subgroup C, such as Ad2 and Ad5, bind to different receptors as compared to adenoviruses from subgroup B such as Ad3 and Ad7 (Defer et al., 1990; Gall et al., 1996). Likewise, it was demonstrated that receptor specificity could be altered by exchanging the Ad3 knob protein with the Ad 5 knob protein, and vice versa (Krasnykh et al., 1996; Stevenson et al., 1995, 1997). Serotypes 2, 4, 5 and 7 all have a natural affinity towards lung epithelia and other respiratory tissues. In contrast, serotypes 40 and 41 have a natural affinity towards the gastrointestinal tract. These serotypes differ in at least capsid proteins (penton-base, hexon), proteins responsible for cell binding (fiber protein), and proteins involved in adenovirus replication. It is unknown to what extent the capsid proteins determine the differences in tropism found between the serotypes. It may very well be that post-infection mechanisms determine cell type specificity of adenoviruses. It has been shown that adenoviruses from serotypes A (Ad12 and Ad31), C (Ad2 and Ad5), D (Ad9 and Ad15), E (Ad4) and F (Ad41) all are able to bind labeled, soluble CAR (sCAR) protein when immobilized on nitro-cellulose. Furthermore, binding of adenoviruses from these serotypes to Ramos cells, that express high levels of CAR but lack integrins (Roelvink et al., 1996), could be efficiently blocked by addition of sCAR to viruses prior to infection (Roelvink et al., 1998). However, the fact that (at least some) members of these subgroups are able to bind CAR does not exclude that these viruses have different infection efficiencies in various cell types. For example, subgroup D serotypes have relatively short fiber shafts compared to subgroup A and C viruses. It has been postulated that the tropism of subgroup D viruses is to a large extend determined by the penton base binding to integrins (Roelvink et al., 1996; Roelvink et al., 1998). Another example is provided by Zabner et al., 1998 who tested 14 different serotypes on infection of human ciliated airway epithelia ("CAE") and found that serotype 17 (subgroup D) was bound and internalized more efficiently then all other viruses, including other members of subgroup D. Similar experiments using serotypes from subgroup A-F in primary fetal rat cells showed that adenoviruses from subgroup A and B were inefficient whereas viruses from subgroup D were most efficient (Law et al., 1998). Also, in this case, viruses within one subgroup displayed different efficiencies. The importance of fiber binding for the improved infection of Ad 17 in CAE was shown by Armentano et al. (published PCT International Patent Application WO 98/22609) who made a recombinant LacZ Ad2 virus with a fiber gene from Ad 17 and showed that the chimaeric virus infected CAE more efficiently than LacZ Ad2 viruses with Ad2 fibers.

Thus, despite their shared ability to bind CAR, differences in the length of the fiber, knob sequence and other capsid proteins like penton base may determine the efficiency by which an adenovirus infects a certain target cell. Of interest is that Ad5 and Ad2 fibers bind to fibronectin III and MHC class 1 a2 derived peptides, while Ad3 fibers do not. This suggests that adenoviruses are able to use cellular receptors other than CAR (Hong et al., 1997).

Serotypes 40 and 41 (subgroup F) are known to carry two fiber proteins differing in the length of the shaft. The long shafted 41L fiber is shown to bind CAR whereas the short shafted 41S is not capable of binding CAR (Roelvink et al., 1998). The receptor for the short fiber is not known.

Adenoviral Nucleic Acid Delivery Vectors

Most adenoviral nucleic acid delivery vectors currently used in gene therapy are derived from the serotype C adenoviruses Ad2 or Ad5. The vectors have a deletion in the E1 region, where novel genetic information can be introduced. The E1 deletion renders the recombinant virus replication defective. It has been demonstrated extensively that recombinant adenovirus, in particular serotype 5, is suitable for efficient transfer of genes in vivo to the liver, the airway epithelium and solid tumors in animal models and human xenografts in immuno-deficient mice (Bout 1996, 1997; Blaese et al., 1995).

Nucleic acid transfer vectors derived from adenoviruses ("adenoviral vectors") have a number of features that make them particularly useful for nucleic acid transfer:
1) the biology of the adenoviruses is well characterized,
2) the adenovirus is not associated with severe human pathology,
3) the adenovirus is extremely efficient in introducing its DNA into the host cell,
4) the adenovirus can infect a wide variety of cells and has a broad host-range,
5) the adenovirus can be produced at high titers in large quantities, and
6) the adenovirus can be rendered replication defective by deletion of the early-region 1 (E1) of the viral genome (Brody and Crystal, 1994).

However, there are still a number of drawbacks associated with the use of adenoviral vectors. These include:
1) Adenoviruses, especially the well investigated serotypes Ad2 and Ad5, usually elicit an immune response by the host into which they are introduced,
2) it is currently not feasible to target the virus to certain cells and tissues,
3) Some cell types are not easily transduced by the current generation of adenovirus vectors.
4) the serotypes Ad2 or Ad5 are not ideally suited for delivering additional genetic material to organs other than the liver. The liver can be particularly well transduced with vectors derived from Ad2 or Ad5. Administration of these vectors via the bloodstream leads to a significant delivery of the vectors to the cells of the liver. In therapies were cell types other than liver cells need to be transduced some means of liver exclusion must be applied to prevent uptake of the vector by these cells. Current methods rely on the physical separation of the vector from the liver cells. Most of these methods rely on localizing the vector and/or the target organ via surgery, balloon angioplasty or direct injection into an organ or a bone structure via, for instance, needles. Liver exclusion is also being practiced through delivery of the vector to compartments in the body that are essentially isolated from the bloodstream thereby preventing transport of the vector to the liver. Although these methods mostly succeed in avoiding gross delivery of the vector to the liver, most of the methods are crude and still have considerable leakage and/or have poor target tissue penetration characteristics. In some cases, inadvertent delivery of the vector to liver cells can be toxic to the patient. For instance, delivery of a HSV TK gene for the subsequent killing of dividing cancer cells through administration of GCV is not without risk when also a significant amount of liver cells are transduced by the vector. Significant delivery and subsequent expression of the HSV-TK gene to liver cells is associated with severe toxicity. Thus, there is a discrete need for an inherently safe vector provided with the property of a reduced transduction efficiency of liver cells.

BRIEF SUMMARY OF THE INVENTION

The invention involves the introduction of genetic material into fibroblast-like or macrophage-like cells, preferably synoviocytes. The invention further involves various means and methods for at least in part preventing delivery of nucleic acid into liver cells. The invention further provides means and methods for treating disease by at least in part specifically transferring nucleic acid into synoviocytes.

The invention provides materials and methods to overcome at least part of the limitations of nucleic delivery vehicles.

In one aspect, the invention provides new adenoviruses, derived in whole or in part from serotypes different from Ad5. Specific genes of serotypes with preferred characteristics may be combined in a chimaeric vector to give rise to a vector that is better suited for specific applications. Preferred characteristics include, but are not limited to, improved infection of a specific target cell, reduced infection of non-target cells, improved stability of the virus, reduced uptake in antigen presenting cells ("APC"), or increased uptake in APC, reduced toxicity to target cells, reduced neutralization in humans or animals, reduced or increased CTL response in humans or animals, better and/or prolonged transgene expression, increased penetration capacity in tissues, improved yields in packaging cell lines, etc.

In one aspect, the invention facilitates the combination of the low immunogenicity of some adenoviruses with the characteristics of other adenoviruses. Such adenoviruses may be favorable for gene therapy approaches. Such characteristics may be a high specificity for certain host cells, a good replication machinery for certain cells, a high rate of infection in certain host cells, low infection efficiency in non-target cells, high or low efficiency of APC infection, etc.

The invention thus may provide chimaeric adenoviruses having the useful properties of at least two adenoviruses of different serotypes. Typically, two or more requirements from the above non-exhaustive list are required to obtain an adenovirus capable of efficiently transferring genetic material to a host cell. In one aspect, the present invention therefore provides adenovirus derived vectors which can be used as cassettes to insert different adenoviral genes from different adenoviral serotypes at the required sites. This way, one can obtain a vector capable of producing a chimaeric adenovirus, whereby of course also a gene of interest can be inserted (for instance at the site of E1 of the original adenovirus). In this manner, the chimaeric adenovirus to be produced can be adapted to the requirements and needs of certain hosts in need of gene therapy for certain disorders. To enable this virus production, a packaging cell will generally be needed in order to produce sufficient amount of safe chimaeric adenoviruses.

In one of its aspects, the invention provides adenoviral vectors comprising at least a part of a fiber protein of an adenovirus from subgroup B, in particular of serotypes 11, 16, 35 and/or 51. The fiber protein may be the native fiber protein of the adenoviral vector or may be derived from a serotype different from the serotype the adenoviral vector is based on. In the latter case the adenoviral vector according to the invention is a chimaeric adenovirus displaying at least a part of the fiber protein derived from subgroup B adenoviruses that part comprising at least the receptor binding sequence. Typically, such a virus will be produced using a vector (typically a plasmid, a cosmid or baculovirus vector). Such vectors are also subject of the present invention. A preferred vector is a vector that can be used to make a chimaeric recombinant virus specifically adapted to the host to be treated and the disorder to be treated.

The present invention also provides a chimaeric adenovirus based on adenovirus type 5 but having at least a part of the fiber sequence from adenovirus type 16, whereby the part of the fiber of Ad16 at least comprises a part of the fiber protein that is involved in binding a host cell.

The invention also provides chimaeric adenoviral vectors that show improved infection as compared to adenoviruses from other subgroups in specific host cells for example, but not limited to, fibroblast-like or macrophage-like cells, preferably synoviocytes of human or animal origin. An important feature of part of the present invention is a means to produce the chimaeric virus. Typically, one does not want an adenovirus batch to be administered to the host cell, which contains replication competent adenovirus. In general, therefore, it is desired to omit a number of genes (but at least one) from the adenoviral genome on the vector encoding the chimaeric virus and to supply these genes in the genome of the cell in which the vector is brought to produce chimaeric adenovirus. Such a cell is usually called a packaging cell. The invention thus also provides a packaging cell for producing a chimaeric adenovirus according to the invention, comprising in trans all elements necessary for adenovirus production not present on the adenoviral vector according to the invention. Typically, vector and packaging cell have to be adapted to one another in that they have all the necessary elements, but that they do not have overlapping elements which lead to replication competent virus by recombination. Thus, the invention also provides a kit of parts comprising a packaging cell according to the invention and a recombinant vector according the invention whereby there is essentially no sequence overlap leading to recombination resulting in the production of replication competent adenovirus between the cell and the vector.

For certain applications, for example when the therapy is aimed at eradication of tumour cells, the adenoviral vector according to the invention may be replication competent or capable of replicating under certain conditions, for example, in specific cell types like tumour cells.

It is within the scope of the invention to insert more genes, or a functional part of these genes from the same or other serotypes into the adenoviral vector replacing the corresponding native sequences. Thus, for example, replacement of (a functional part of the) fiber sequences with corresponding sequences of other serotypes may be combined with, for example, replacements of (a functional part of) other capsid genes like penton base or hexon with corresponding sequences of the serotype or of other distinct serotypes. Persons skilled in the art understand that other combinations, not limited to the genes, are possible and are within the scope of the invention.

A chimaeric adenoviral vector according to the invention may originate from at least two different serotypes. This may provide the vector with preferred characteristics such as improved infection of target cells and/or less infection of non-target cells, improved stability of the virus, reduced immunogenicity in humans or animals (e.g., reduced uptake in APC, reduced neutralization in the host and/or reduced cytotoxic T-lymphocyte ("CTL") response), increased penetration of tissue, better longevity of transgene expression, etc. In this aspect, it is preferred to use capsid genes, for example, penton and/or hexon genes from less immunogenic serotypes as defined by the absence or the presence of low amounts of neutralizing antibodies in the vast majority of hosts. It is also preferred to use fiber and/or penton sequences from serotypes that show improved binding and internalization in the target cells. Furthermore, it is preferred to delete from the viral vector those genes which lead to expression of adenoviral genes in the target cells. In this aspect, a vector deleted of all adenoviral genes is also preferred. Furthermore, it is preferred that the promoter driving the gene of interest to be expressed in the target cells is a cell type specific promoter.

In order to be able to precisely adapt the viral vector and provide the chimaeric virus with the desired properties at will, it is preferred that a library of adenoviral genes is provided whereby the genes to be exchanged are located on plasmid- or cosmid-based adenoviral constructs whereby the genes or the sequences to be exchanged are flanked by restriction sites. The preferred genes or sequences can be selected from the library and inserted in the adenoviral constructs that are used to generate the viruses. Typically, such a method comprises a number of restriction and ligation steps and transfection of a packaging cell. The adenoviral vector can be transfected in one piece, or as two or more overlapping fragments, whereby viruses are generated by homologous recombination. For example, the adenoviral vector may be built up from two or more overlapping sequences for insertion or replacements of a gene of interest in, for example, the E1 region, for insertion or replacements in penton and/or hexon sequences, and for insertions or replacements into fiber sequences. In one aspect, the invention provides a method for producing chimaeric adenoviruses having one or more desired properties like a desired host range and diminished antigenicity, comprising providing one or more vectors according to the invention having the desired insertion sites, inserting into the vectors at least a functional part of a fiber protein derived from an adenovirus serotype having the desired host range and/or inserting a functional part of a capsid protein derived from an adenovirus serotype having relatively low antigenicity and transfecting the vectors in a packaging cell according to the invention and allowing for production of chimaeric viral particles. Of course, other combinations of other viral genes originating from different serotypes can also be inserted as disclosed herein before. Chimaeric viruses having only one non-native sequence in addition to an insertion or replacement of a gene of interest in the E1 region, are also within the scope of the invention.

An immunogenic response to adenovirus that typically occurs, is the production of neutralizing antibodies by the host. This is typically a reason for selecting a capsid protein like penton, hexon and/or fiber of a less immunogenic serotype.

Of course, it may not be necessary to make chimaeric adenoviruses which have complete proteins from different serotypes. It is well within the skill of the art to produce chimaeric proteins. For instance, in the case of fiber proteins, it is very well possible to have the base of one serotype and the shaft and the knob from another serotype. In this manner, it becomes possible to have the parts of the protein responsible for assembly of viral particles originate from one serotype, thereby enhancing the production of intact viral particles. Thus, the invention also provides a chimaeric adenovirus according to the invention, wherein the hexon, penton, fiber and/or other capsid proteins are chimaeric proteins originating from different adenovirus serotypes. Besides generating chimaeric adenoviruses by swapping entire wild type capsid (protein) genes etc. or parts thereof, it is also within the scope of the present invention to insert capsid (protein) genes etc. carrying non-adenoviral sequences or mutations such as point mutations, deletions, insertions, etc. Such chimaeric adenoviruses can be easily screened for preferred characteristics such as temperature stability, assembly, anchoring, redirected infection, altered immune response etc. Again, other chimaeric combinations can also be produced and are within the scope of the present invention.

It has been demonstrated in mice and rats that upon in vivo systemic delivery of recombinant adenovirus of common used serotypes for gene therapy purposes, more than 90% of the virus is trapped in the liver (Herz et al., 1993; Kass-Eisler et al., 1994; Huard et al., 1995). It is also known that human hepatocytes are efficiently transduced by adenovirus serotype 5 ("Ad5") vectors (Castell, J. V., Hernandez, D. Gomez-Foix, A. M., Guillen, I, Donato, T. and Gomez-Lechon, M. J. (1997). Adenovirus-mediated gene transfer into human hepatocytes: analysis of the biochemical functionality of transduced cells. Gene Ther. 4(5), p455–464). Thus, in vivo gene therapy by systemic delivery of Ad2 or Ad5 based vectors is seriously hampered by the efficient uptake of the viruses in the liver leading to unwanted toxicity and less virus being available for transduction of the target cells. Therefore, alteration of the Ad5 host cell range to be able to target other organs in vivo is a major interest of the invention.

To obtain re-directed infection of recombinant Ad5, several approaches have been or still are under investigation. Wickham et al. have altered the RGD (Arg, Gly, Asp) motif in the penton base which is believed to be responsible for the $a_v b_3$ and $a_v b_5$ integrin binding to the penton base. They have replaced this RGD motif by another peptide motif which is specific for the $a_4 b_1$ receptor. In this way, targeting the adenovirus to a specific target cell could be accomplished (Wickham et al., 1995). Krasnykh et al. (1998) have made use of the HI loop available in the knob. This loop is, based on X-ray crystallography, located on the outside of the knob trimeric structure and therefore is thought not to contribute to the intramolecular interactions in the knob. Insertion of a FLAG coding sequence into the HI loop resulted in fiber proteins that were able to trimerise and it was further shown that viruses containing the FLAG sequence in the knob region could be made. Although interactions of the FLAG-containing knob with CAR are not changed, insertion of ligands in the HI loop may lead to retargeting of infection. Although successful introduction of changes in the Ad5 fiber and penton-base have been reported, the complex structure of knob and the limited knowledge of the precise amino acids interacting with CAR render such targeting approaches laborious and difficult. The use of antibodies binding to CAR and to a specific cellular receptor has also been described (Wickham et al., 1996; Rogers et al., 1997). This approach is however limited by the availability of a specific antibody and by the complexity of the gene therapy product.

To overcome the limitations described above we used pre-existing adenovirus fibers, penton base proteins, hexon proteins or other capsid proteins derived from other adenovirus serotypes. By generating chimaeric Ad5 libraries containing structural proteins of alternative adenovirus serotypes, we have developed a technology, which enables rapid screening for a recombinant adenoviral vector with preferred characteristics.

The invention provides methods for the generation of chimaeric capsids which can be targeted to specific cell types in vitro as well as in vivo, and thus have an altered tropism for certain cell types. The invention also provides methods and means by which an adenovirus or an adenovirus capsid can be used as a protein or nucleic acid delivery vehicle to a specific cell type or tissue.

The generation of chimaeric adenoviruses based on Ad5 with modified late genes is described. For this purpose, three plasmids, which together contain the complete Ad5 genome, were constructed. From one of these plasmids, part of the DNA encoding the Ad5 fiber protein was removed and replaced by linker DNA sequences that facilitate easy cloning. This plasmid subsequently served as template for the insertion of DNA encoding fiber protein derived from different adenovirus serotypes. The DNA sequences derived from the different serotypes were obtained using the polymerase chain reaction technique in combination with (degenerate) oligonucleotides. At the former E1 location in the genome of Ad5, any gene of interest can be cloned. A single transfection procedure of the three plasmids together results in the formation of a recombinant chimaeric adenovirus. Alternatively, cloning of sequences obtained from a library of genes can be such that the chimaeric adenoviral vector is built up from one or more fragments. For example, one construct contains at least the left ITR and sequences necessary for packaging of the virus, an expression cassette for the gene of interest and sequences overlapping with a second construct, wherein a second construct comprises all sequences necessary for replication and virus formation not present in the packaging cell as well as non-native sequences providing the preferred characteristics. This new technology of libraries consisting of chimaeric adenoviruses thus allows for a rapid screening for improved recombinant adenoviral vectors for in vitro and in vivo gene therapy purposes.

The use of adenovirus type 5 for in vivo gene therapy is limited by the apparent inability to infect certain cell types efficiently, for example, fibroblast-like or macrophage-like cells, preferably synoviocytes and the preference of infection of certain organs, for example, liver and spleen. Specifically, this has consequences for treatment of rheumatoid arthritis (RA). Adenovirus-mediated delivery of, for instance, HSV TK into synoviocytes has been proposed as a possible treatment for RA. However, efficient delivery of the gene is required.

In one embodiment, the invention describes adenoviral vectors that are, amongst other things, especially suited for nucleic acid delivery to fibroblast-like or macrophage-like cells, most especially to synoviocytes. This feature is of particular importance for the treatment of diseases related to joints, particularly for the treatment of rheumatoid arthritis. The adenoviral vectors preferably are derived from subgroup B adenoviruses or contain at least a functional part of the fiber protein from an adenovirus from subgroup B comprising at least the cell-binding moiety of the fiber protein.

In a further preferred embodiment, the adenoviral vectors are chimaeric vectors based on adenovirus type 5 and contain at least a functional part of the fiber protein from adenovirus type 16.

In another embodiment, the invention provides adenoviral vectors or chimaeric adenoviral vectors that escape at least in part the liver following systemic administration. Preferably, the adenoviral vectors are derived from subgroup B, in particular serotype 16 or contain at least the cell-binding moiety of the fiber protein derived from the adenovirus.

It is to be understood that in all embodiments adenoviral vectors and/or particles may be derived solely from one serotype having the desired properties or that an adenoviral vector and/or particle comprises sequences and/or protein or functional parts, derivatives and/or analogues thereof, of two or more adenovirus serotypes.

In another aspect, the invention provides chimaeric adenoviruses and methods to generate viruses that have an altered tropism different from that of Ad5. For example, viruses based on Ad5 but displaying any adenovirus fiber existing in nature. This chimaeric Ad5 is able to infect certain cell types more efficiently, or less efficiently in vitro and in vivo than the Ad5. Such cells include, but are not limited to, endothelial cells, smooth muscle cells, dendritic cells, neuronal cells, monocytic/macrophage cells, glial cells, synovical cells, lung epithelial cells, hemopoietic stem cells, tumour cells, skeletal muscle cells, mesothelial cells, synoviocytes, etc.

In another aspect, the invention provides for the construction and use of libraries consisting of distinct parts of Ad5 in which one or more genes or sequences have been replaced with DNA derived from alternative human or animal serotypes. This set of constructs, in total encompassing the complete adenovirus genome, allows for the construction of unique chimaeric adenoviruses customized for a certain disease, group of patients or even a single individual.

In all aspects of the invention, the chimaeric adenoviruses may, or may not, contain deletions in the E1 region and insertions of heterologous genes linked either or not to a promoter. Furthermore, chimaeric adenoviruses may, or may not, contain deletions in the E3 region and insertions of heterologous genes linked to a promoter. Furthermore, chimaeric adenoviruses may, or may not, contain deletions in the E2 and/or E4 region and insertions of heterologous genes linked to a promoter. In the latter case, E2 and/or E4 complementing cell lines are required to generate recombinant adenoviruses. In fact, any functional nucleic acid in the genome of the viral vector can be taken out and supplied in trans. Thus, in the extreme situation, chimaeric viruses do not contain any adenoviral genes in their genome and are by definition minimal adenoviral vectors. In this case, required adenoviral functions are supplied in trans using stable cell lines and/or transient expression of these genes. A method for producing minimal adenoviral vectors is described in published International Patent Application WO97/00326, the contents of which are incorporated by this reference. In another case, Ad/AAV chimaeric molecules are packaged into the adenovirus capsids of the invention. A method for producing Ad/AAV chimaeric vectors is described in European Patent Appl'n EP 97204085.1, the contents of which are incorporated by this reference. In principle, any nucleic acid may be provided with the adenovirus capsids of the invention.

In one embodiment, the invention provides a nucleic acid delivery vehicle comprising or having been provided with, at least a tissue tropism for fibroblast-like or macrophage-like cells, preferably synoviocytes; In another embodiment, the invention provides a nucleic acid delivery vehicle comprising an at least in part reduced or having at least in part been deprived of a tissue tropism for at least liver cells. Preferably, the nucleic acid delivery vehicle is provided with a tissue tropism for at least fibroblast-like or macrophage-like cells, preferably synoviocytes and at least in part deprived of a tissue tropism for at least liver cells. In a preferred embodiment, the nucleic acid delivery vehicle is provided with a tissue tropism for at least fibroblast-like or macrophage-like cells, preferably synoviocytes and/or at least in part deprived of a tissue tropism for at least liver cells using a fiber protein derived from a subgroup B adenovirus, typically of serotypes 11, 16, 35 and/or 51 and preferably of adenovirus 16.

In a preferred embodiment, the nucleic acid delivery vehicle comprises a virus capsid or a functional part, derivative and/or analogue thereof. Preferably, the virus capsid comprises a virus capsid derived in whole or in part from an adenovirus of subgroup B, preferably from adenovirus 16, or it comprises proteins, or functional parts, derivatives or analogues thereof, from an adenovirus of subgroup B, preferably of adenovirus 16.

In a preferred embodiment, the virus capsid comprises proteins, or functional parts, derivatives or analogues thereof, from at least two different viruses, preferably adenoviruses. In a preferred embodiment, at least one of the viruses is an adenovirus of subgroup B, preferably adenovirus 16.

In a preferred embodiment, the nucleic acid delivery vehicle comprises an adenovirus fiber protein or parts thereof. The fiber protein is preferably derived from an adenovirus of subgroup B, preferably of adenovirus 16. The nucleic acid delivery vehicle may further comprise other fiber proteins, or parts thereof, from other adenoviruses. The nucleic acid delivery vehicle may or may not comprise other adenovirus proteins. Nucleic acid may be linked directly to the fiber protein, or parts thereof, but may also be linked indirectly. Examples of indirect linkages include but are not limited to, packaging of nucleic acid into adenovirus capsids or packaging of nucleic acid into liposomes, wherein a fiber protein, or a part thereof, is incorporated into an adenovirus capsid or linked to a liposome. Direct linkage of nucleic acid to a fiber protein, or a part thereof, may be performed when the fiber protein, is not part of a complex or when the fiber protein is part of complex such as an adenovirus capsid.

In one embodiment, the invention provides a nucleic acid delivery vehicle comprising an adenovirus fiber protein wherein the fiber protein comprises at least a tissue determining part of an adenovirus of subgroup B adenovirus, preferably of adenovirus 16. Adenovirus fiber protein comprises at least three functional domains. One domain, the base, is responsible for anchoring a fiber to a penton base of an adenovirus capsid. Another domain, the knob, is responsible for receptor recognition whereas the shaft domain functions as a spacer separating the base from the knob. The different domains may also have other function. For instance, the shaft is presumably also involved in target cell specificity. Each of the domains mentioned above alone or in combination, may be used to define a part of a fiber. However, parts may also be identified in another way. For instance, the knob domain comprises of a receptor binding part and a shaft binding part. The base domain comprises of a penton base binding part and a shaft binding part. Moreover, the shaft comprises of repeated stretches of amino acids. Each of these repeated stretches may be a part or used in combination with one or more other parts to form a tissue determining part of a fiber protein. Preferably, the tissue determining part of a fiber protein comprises at least the knob domain of the fiber protein, or a functional part, derivative and/or analogue thereof.

A tissue tropism determining part of a fiber protein may be a single part of a fiber protein or a combination of parts derived from at least one fiber protein, wherein the tissue tropism determining part, either alone or in combination with a virus capsid, determines the efficiency with which a nucleic acid delivery vehicle can transduce a given cell or cell type, preferably but not necessarily in a positive way. With a tissue tropism for liver cells is meant a tissue tropism for cells residing in the liver, preferably liver parenchyma cells.

A tissue tropism for a certain tissue may be provided by increasing the efficiency with which cells of the tissue are transduced, alternatively, a tissue tropism for a certain tissue may be provided by decreasing the efficiency with which other cells than the cells of the tissue are transduced.

Fiber proteins possess tissue tropism determining properties. The best described part of fiber protein involved in tissue tropism is the knob domain. However, the shaft domain of the fiber protein also possesses tissue tropism determining properties. However, not all of the tissue tropism determining properties of an adenovirus capsid are incorporated into a fiber protein.

In a preferred embodiment, a fiber protein derived from a subgroup B adenovirus, typically ad 11, 16, 35 and/or 51, preferably adenovirus 16 or a functional part, derivative and/or analogue thereof, is combined with at least one non-fiber capsid proteins from an adenovirus of subgroup C, preferably of adenovirus 5.

In one aspect, the invention provides a nucleic acid delivery vehicle comprising at least part of a nucleic acid derived from an adenovirus. In a preferred embodiment, the adenovirus nucleic acid comprises at least one nucleic acid encoding a fiber protein comprising at least a tissue tropism determining part of a subgroup B adenovirus fiber protein, preferably of adenovirus 16. In a preferred aspect the adenovirus comprises nucleic acid from at least two different adenoviruses. In a preferred aspect, the adenovirus comprises nucleic acid from at least two different adenoviruses wherein at least part of the nucleic acid encodes a fiber protein comprising at least a tissue tropism determining part of a subgroup B adenovirus fiber protein, preferably of adenovirus 16.

In a preferred embodiment, adenovirus nucleic acid is modified such that the capacity of the adenovirus nucleic acid to replicate in a target cell has been reduced or disabled. This may be achieved by among other ways, through inactivating or deleting genes encoding early region 1 proteins.

In another preferred embodiment, the adenovirus nucleic acid is modified such that the capacity of a host immune system to mount an immune response against adenovirus proteins encoded by the adenovirus nucleic acid has been reduced or disabled. This may be achieved, by among other means, through deletion of genes encoding proteins of early region 2 and/or early region 4. Alternatively, genes encoding early region 3 proteins, may be deleted, or on the contrary, considering the anti-immune system function of some of the proteins encoded by the genes in early region 3, the expression of early region 3 proteins may be enhanced for some purposes. Also, adenovirus nucleic acid may be altered by a combination of two or more of the alterations of adenovirus nucleic acid mentioned above. It is clear that when nucleic acid encoding essential functions are deleted from adenovirus nucleic acid, the essential functions must be complemented in the cell that is going to produce adenovirus nucleic acid, adenovirus vector, vehicle or chimaeric capsid. Adenovirus nucleic acid may also be modified such that the capacity of a host immune system to mount an immune response against adenovirus proteins encoded by the adenovirus nucleic acid has been reduced or disabled, in other ways then mentioned above, for instance, through exchanging capsid proteins, or parts thereof, by capsid proteins, or parts thereof, from other serotypes for which humans or animals do not have, or have low levels of, neutralizing antibodies. Another example is the exchange of nucleic acid encoding capsid proteins with nucleic acid encoding capsid proteins from other serotypes. Also, capsid proteins, or parts thereof, may be exchanged for other capsid proteins, or parts thereof, for which individuals are not capable of, or have a low capacity of, raising an immune response against.

An adenovirus nucleic acid may be altered further or instead of one or more of the alterations mentioned above, by inactivating or deleting genes encoding adenovirus late proteins such as but not-limited to, hexon, penton, fiber and/or protein IX.

In a preferred embodiment, all genes encoding adenovirus proteins are deleted from the adenovirus nucleic acid, turning the nucleic acid into a minimal adenovirus vector.

In another preferred embodiment, the adenovirus nucleic acid is an Ad/AAV chimaeric vector, wherein at least the integration means of an adeno-associated virus (AAV) are incorporated into the adenovirus nucleic acid.

In a preferred embodiment, a vector or nucleic acid, which may be or may not be one and the same, further comprises at least one non-adenoviral nucleic acid. Preferably, at least one of the non-adenovirus nucleic acid is a nucleic acid encoding the following protein or a functional part, derivative and/or analogue thereof: an apolipoprotein, a nitric oxide synthase, a HSV TK, an interleukin-3, an interleukin-1RA, an interleukin-1α, an (anti)angiogenesis protein such as angiostatin or endostatin, an anti-proliferation protein, a vascular endothelial growth factor ("VGEF"), a basic fibroblast growth factor ("bFGF"), a hypoxia inducible factor 1α ("HIF-1α"), a PAI-1, a smooth muscle cell anti-migration protein, an erythropoietin, a CD40, a FasL, an interleukin-12, an interleukin-10, an interleukin-4, an interleukin-13, an excreted single chain antibody to CD4, CD5, CD7, CD52, interleukin-2, interleukin-1, interleukin-6, tumour necrosis factor ("TNF"), etc. or an excreted single chain antibody to a T-cell receptor on the auto-reactive T-cells, a dominant negative mutant of promyelocytic leukemia ("PML") to inhibit the immune response, an antagonist of inflammation promoting cytokines such as, for example, interleukin-1RA (receptor antagonist) and soluble receptors like soluble interleukin 1 receptor I ("IL-1RI"), soluble interleukin 1 receptor II ("sIL-1RII"), soluble tumour necrosis factor receptor I ("sTNFRI") and II ("sTN-FRII"), a growth and/or immune response inhibiting protein such as a protein encoded by a the genes Bcl3, cactus or IκBα, β or γ, an apoptosis inducing protein like the VP3 protein of chicken anemia virus or a protein encoded by a suicide gene like cytosine deaminase, nitroreductase and linamerase. Gene delivery vehicles according to the invention comprising nucleic acid encoding one or more of the proteins or a functional parts, derivatives and/or analogues thereof can be used to kill or inhibit growth of synoviocytes and/or T-cells in the affected joints.

In another aspect, the invention provides a cell for the production of a nucleic acid delivery vehicle comprising or provided with at least a tissue tropism for fibroblast-like or macrophage-like cells, preferably synoviocytes. In another aspect, the invention provides a cell for the production of a nucleic acid delivery vehicle comprising a reduced tissue tropism for liver cells or having at least in part been deprived of a tissue tropism for liver cells. In another aspect, the invention provides a cell for the production of a nucleic acid delivery vehicle comprising or provided with at least a tissue tropism for fibroblast-like or macrophage-like cells, preferably synoviocytes and comprising a reduced tissue tropism for liver cells or having at least in part been deprived of a tissue tropism for liver cells. In a preferred embodiment, the cell is an adenovirus packaging cell, wherein an adenovirus nucleic acid is packaged into an adenovirus capsid. In one aspect, of an adenovirus packaging cell of the invention all functions required for the replication and packaging of an adenovirus nucleic acid, except for the proteins encoded by early region 1, are provided by proteins and/or RNA encoded by the adenovirus nucleic acid. Early region 1 encoded proteins in this aspect of the invention may be encoded by genes incorporated into the cells genomic DNA. In a preferred embodiment, the cell is PER.C6 (deposited under ECACC deposit number 96022940). In general, when gene products required for the replication and packaging of adenovirus nucleic acid into adenovirus capsid are not provided by a adenovirus nucleic acid, they are provided by the packaging cell, either by transient transfection, or through stable transformation of the packaging cell. However, an adenovirus product provided by the packaging cell may also, in addition, be provided by a nucleic acid present on the adenovirus nucleic acid. For instance, fiber protein may be provided by the packaging cell, for instance, through transient transfection, and may be encoded by adenovirus nucleic acid. This feature can among others be used to generate adenovirus capsids comprising of fiber proteins with two different tissue tropisms, for instance, through the use of fiber proteins from two different viruses.

Nucleic acid delivery vehicles of the invention are useful for the treatment diseases, preferably joint related diseases such as rheumatoid arthritis, ankylosing spondylitis and juvenile chronic arthritis. Non-limiting examples of proteins or functional parts, derivatives and/or analogues thereof, of which expression in, for instance, synoviocytes ameliorates at least in part symptoms of diseases are, an apolipoprotein, a nitric oxide synthase, a HSV TK, an interleukin-3, an interleukin-1RA, an interleukin-1α, an (anti)angiogenesis protein such as angiostatin or endostatin, an anti-proliferation protein, a vascular endothelial growth factor (VGEF), a basic fibroblast growth factor ("bFGF"), a hypoxia inducible factor 1α ("HIF-1α"), a PAI-1, a smooth muscle cell anti-migration protein, an erythropoietin, a CD40, a FasL, an interleukin-12, an interleukin-10, an interleukin-4, an interleukin-13, an excreted single chain antibody to CD4, CD5, CD7, CD52, interleukin-2, interleukin-1, interleukin-6, tumour necrosis factor ("TNF"), etc. or an excreted single chain antibody to a T-cell receptor on the auto-reactive T-cells, a dominant negative mutant of promyelocytic leukemia (PML) to inhibit the immune response, an antagonist of inflammation promoting cytokines such as, for example, interleukin-1RA (receptor antagonist) and soluble receptors like soluble interleukin 1 receptor I (IL-1RI), soluble interleukin 1 receptor II (sIL-1RII), soluble tumour necrosis factor receptor I (sTNFRI) and II (sTNFRII), a growth and/or immune response inhibiting protein such as a protein encoded by a the genes Bcl3, cactus or IκBα, β or γ, an apoptosis inducing protein like the VP3 protein of chicken anemia virus or a protein encoded by a suicide gene like cytosine deaminase, nitroreductase and linamerase.

Nucleic acid delivery vehicles of the invention may be used as a pharmaceutical for the treatment of diseases. Alternatively, nucleic acid delivery vehicles of the invention may be used for the preparation of a medicament for the treatment of diseases.

In one aspect, the invention provides an adenovirus capsid with or provided with a tissue tropism for fibroblast-like or macrophage-like cells, preferably synoviocytes wherein the capsid preferably comprises proteins from at least two different adenoviruses and wherein at least a tissue tropism determining part of a fiber protein is derived from a subgroup B adenoviruses, preferably of adenovirus 16. In another aspect the invention provides an adenovirus capsid with a reduced or having at least in part been deprived of a tissue tropism for liver cells wherein the capsid preferably comprises proteins from at least two different adenoviruses and wherein at least a tissue tropism determining part of a fiber protein is derived from a subgroup B adenovirus, preferably of adenovirus 16.

In one embodiment, the invention comprises the use of an adenovirus capsid of the invention, for the delivery of nucleic acid to fibroblast-like or macrophage-like cells, preferably synoviocytes. In another embodiment the invention comprises the use of an adenovirus capsid of the invention, for at least in part preventing delivery of nucleic acid to liver cells.

In another embodiment, the invention provides adenovirus for the treatment rheumatoid arthritis or disease treatable by nucleic acid delivery to fibroblast-like or macrophage-like cells, preferably synoviocytes.

In yet another embodiment, the invention provides adenovirus capsids as part of a pharmaceutical for the treatment of diseases. In yet another embodiment the invention provides adenovirus capsids for the preparation of a medicament for the treatment of diseases.

In another aspect, the invention provides construct pBr/Ad.BamRΔFib, comprising adenovirus 5 sequences 21562–31094 and 32794–35938.

In another aspect, the invention provides construct pBr/AdBamRfib16, comprising adenovirus 5 sequences 21562–31094 and 32794–35938, further comprising an adenovirus 16 nucleic acid encoding fiber protein.

In yet another aspect, the invention provides construct pBr/AdBamR.pac/fib16, comprising adenovirus 5 sequences 21562–31094 and 32794–35938, further comprising an adenovirus 16 nucleic acid encoding fiber protein, and further comprising a unique PacI-site in the proximity of the adenovirus 5 right terminal repeat, in the non-adenovirus sequence backbone of the construct.

In another aspect, the invention provides construct pWE/Ad.AflIIrITRfib16 comprising Ad5 sequence 3534–31094 and 32794–35938, further comprising an adenovirus 16 nucleic acid encoding fiber protein.

In another aspect, the invention provides construct pWE/Ad.AflIIrITRDE2Afib16 comprising Ad5 sequences 3534–22443 and 24033–31094 and 32794–35938, further comprising an adenovirus 16 nucleic acid encoding fiber protein.

In the numbering of the sequences mentioned above, the number is depicted until and not until plus.

In a preferred embodiment, the constructs are used for the generation of a nucleic acid delivery vehicle or an adenovirus capsid with a tissue tropism for fibroblast-like or macrophage-like cells, preferably synoviocytes.

In another aspect, the invention provides a library of adenovirus vectors, or nucleic acid delivery vehicles which may be one and the same or not, comprising a large selection of non-adenovirus nucleic acids. In another aspect, adenovirus genes encoding capsid proteins are used to generate a library of adenovirus capsids comprising of proteins derived from at least two different adenoviruses, the adenoviruses preferably being derived from two different serotypes, wherein preferably one serotype is an adenovirus of subgroup B. In a particularly preferred embodiment of the invention, a library of adenovirus capsids is generated comprising proteins from at least two different adenoviruses and wherein at least a tissue tropism determining part of fiber protein is derived from an adenovirus of subgroup B, preferably of adenovirus 16.

In one embodiment, the invention provides a subgroup B adenovirus capsid comprising a nucleic acid encoding at least one non-adenovirus proteinaceous molecule or RNA molecule. Preferably, the subgroup B adenovirus nucleic acid further comprises subgroup B adenovirus nucleic acid. More preferably, the subgroup B adenovirus nucleic acid has been deprived of the capacity to express E1-region encoded proteins. Most preferably, the subgroup B adenovirus is adenovirus 16.

In another aspect, the invention provides a method for at least in part removing synovium from a joint in an individual comprising administering to the joint a nucleic acid delivery vehicle comprising nucleic acid encoding at least HSV TK or a functional part, derivative and/or analogue thereof and administering to the individual GCV or a functional part, derivative and/or analogue thereof. Preferably, the gene delivery vehicle is vehicle of the invention.

A fiber protein of adenovirus 16 preferably comprises at least part of the sequence given in FIGS. 7A–C. However, within the scope of the present invention, other sequences may be used, for instance, obtained through using codon degeneracy. Alternatively, a fiber sequence may comprise amino-acid substitutions or insertions or deletions compared to the sequence depicted in FIGS. 7A–C, as long as the desired tissue tropism determining property is not significantly altered. Amino-acid substitutions may be within the same polarity group or without.

A transduced cell is a cell provided with nucleic acid. The cell may have been provided with nucleic acid through any means. Similarly, to measure transduction of a cell means to measure nucleic acid transfer into the cell. The transfer may have occurred through any means capable of transferring nucleic into a cell.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 4: Nucleotide sequence of chimeric fiber Ad5/fib16, SEQ ID NO: 32.

FIGS. 7A–7C: Sequences including the gene encoding adenovirus 16 fiber protein as published in GenBank with nucleotide sequence SEQ ID NO: 33 and amino acid sequence SEQ ID NO: 35; and sequences including a gene encoding a fiber from an adenovirus 16 variant as isolated in the present invention with nucleotide sequence SEQ ID NO: 38 and amino acid sequence SEQ ID NO: 34, wherein the sequences of the fiber protein are from the NdeI-site. FIG. 7A nucleotide sequence comparisons of SEQ ID NO: 33 and SEQ ID NO: 38. FIG. 7B amino-acid comparisons of SEQ ID NO: 35 and SEQ ID NO: 34.

FIGS. 16A & 16B are graphs depicting the infection efficiency of Ad5.GFP and Ad5.fib16.GFP in RA synoviocytes and the respective luciferase counts respectively.

DETAILED DESCRIPTION OF THE INVENTION

The invention is further explained by the use of the following illustrative, detailed Examples.

EXAMPLES

Example 1

Generation of Ad5 Based Viruses with Chimaeric Fiber Proteins

Figure 1:
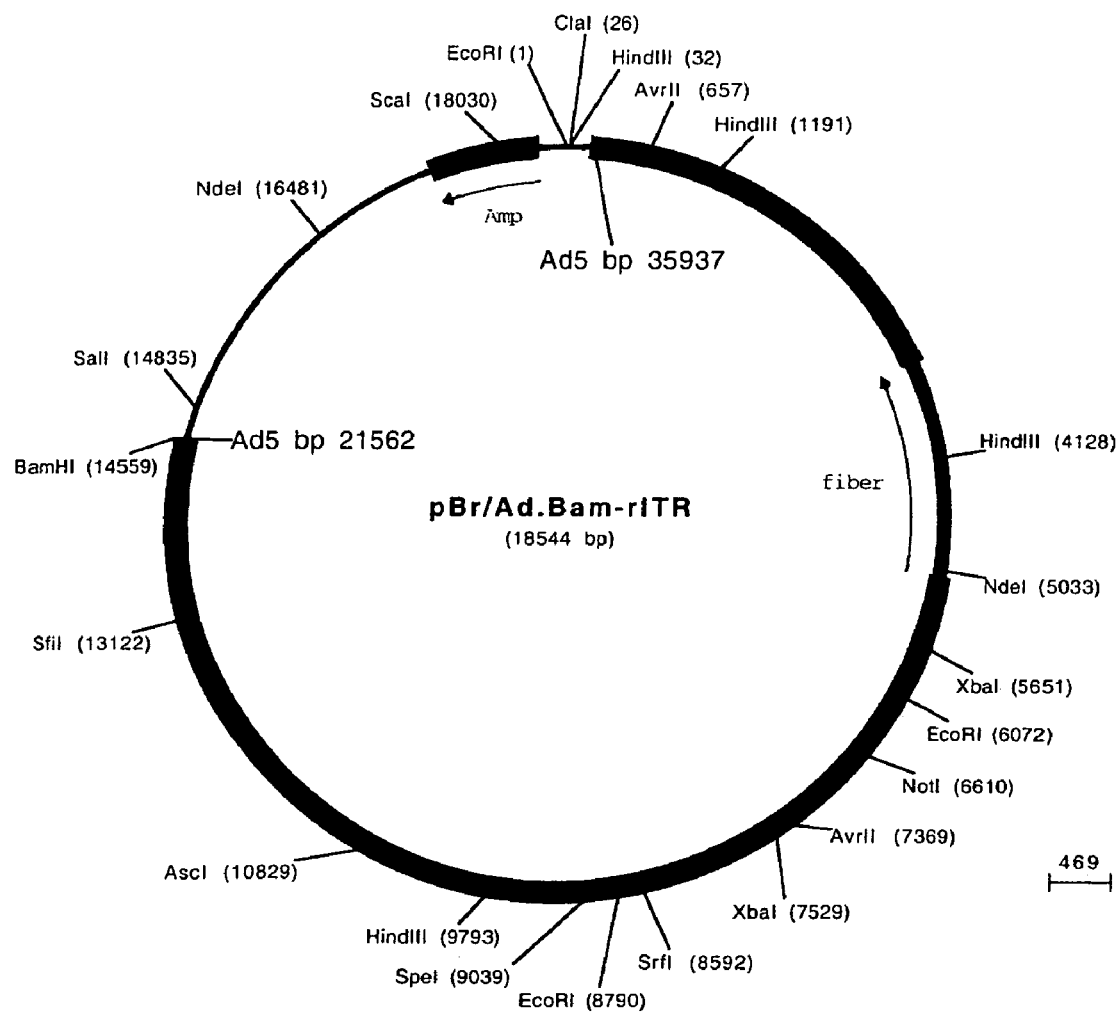
FIG. 1: Schematic drawing of the pBr/Ad.Bam-rITR construct.
Figure 2:
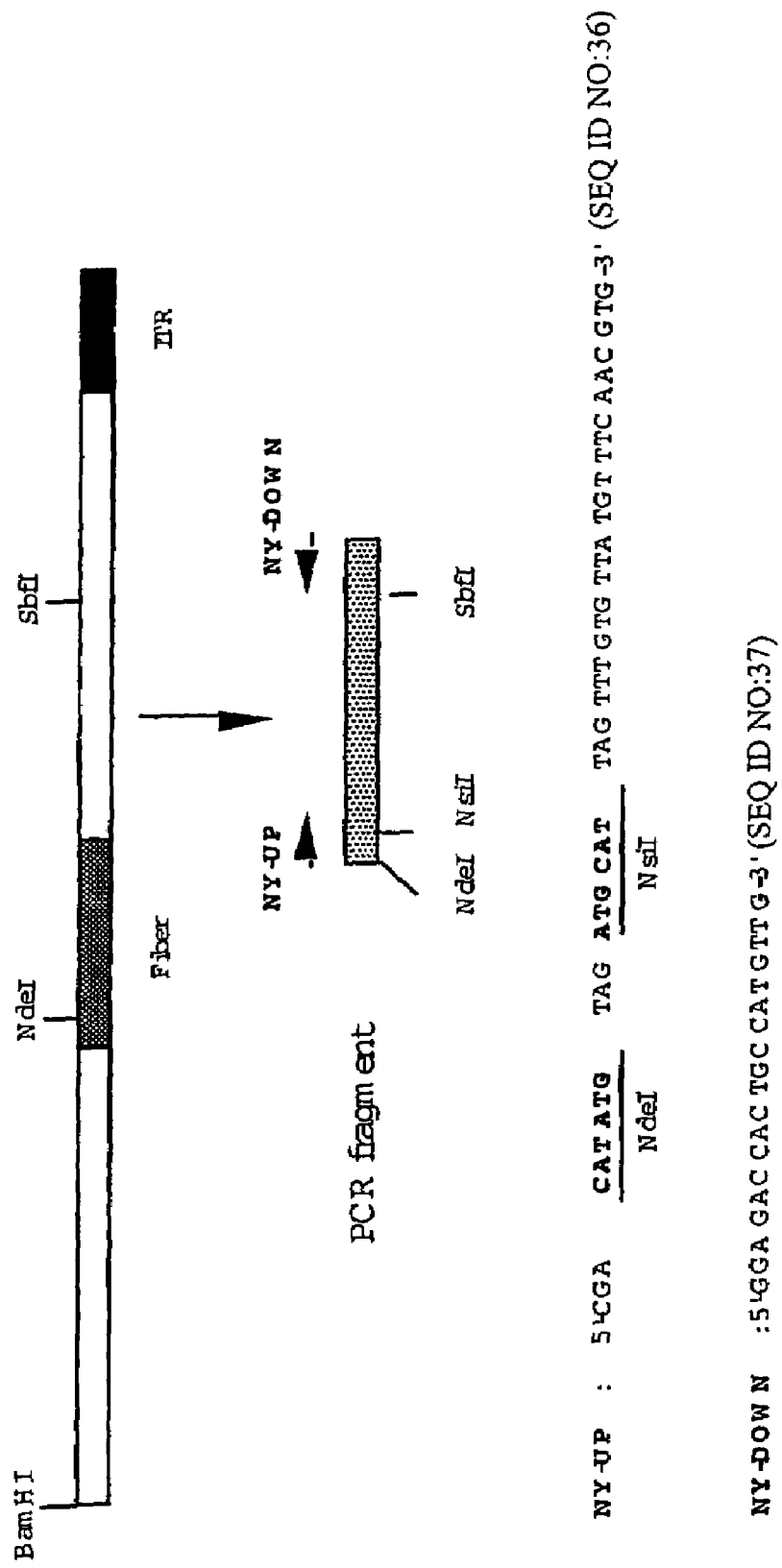
FIG. 2: Schematic drawing of the strategy used to delete the fiber gene from the pBr/Ad.Bam-rITR construct, using primers NY-UP (SEQ ID NO: 36) and NY-DOWN (SEQ ID NO: 37).
Figure 3:
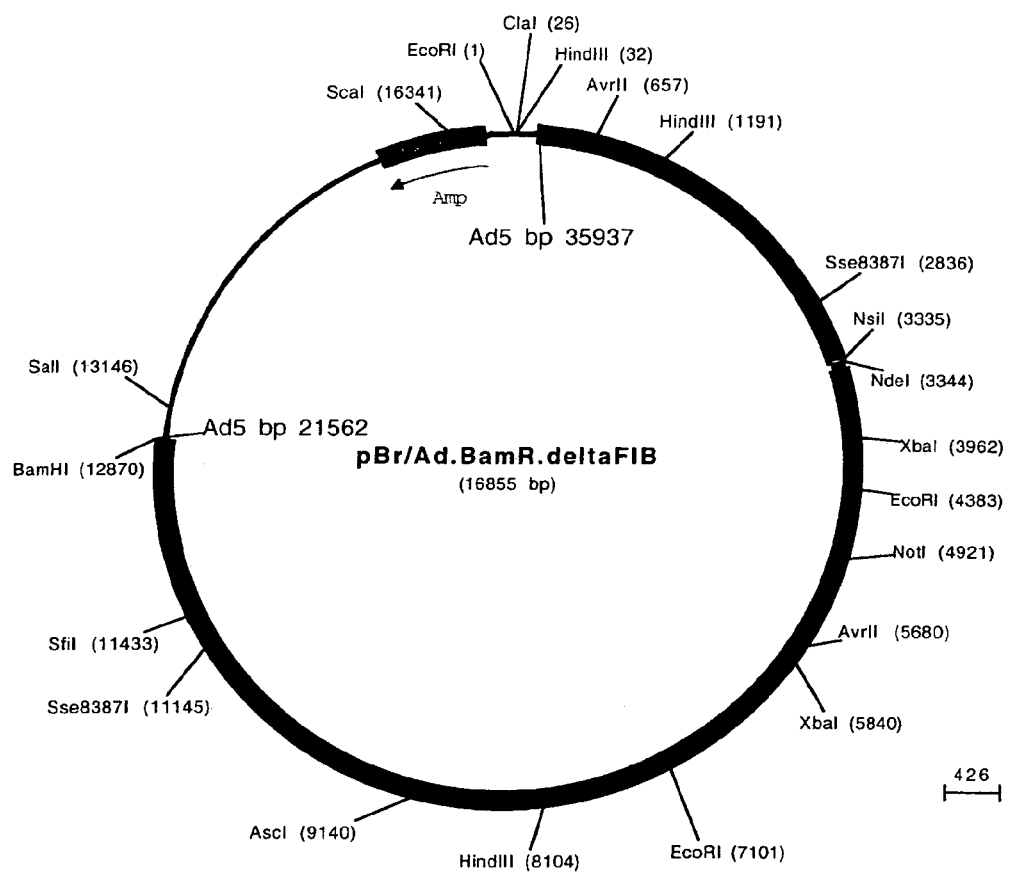
FIG. 3: Schematic drawing of construct pBr/Ad.BamRD-fib.

Generation of adenovirus template clones lacking DNA encoding for fiber. The fiber coding sequence of Ad5 is located between nucleotides 31042 and 32787. To remove the Ad5 DNA encoding fiber we started with construct pBr/Ad.Bam-rITR (FIG. 1; deposited under ECACC deposit P97082122). From this construct, first a NdeI site was removed. For this purpose, pBr322 plasmid DNA was digested with NdeI after which protruding ends were filled using Klenow enzyme. This pBr322 plasmid was then re-ligated, digested with NdeI and transformed into *E. coli* DH5a. The obtained pBr/DNdeI plasmid was digested with ScaI and SalI and the resulting 3198 bp vector fragment was ligated to the 15349 bp ScaI-SalI fragment derived from pBr/Ad.BamrITR, resulting in plasmid pBr/Ad.Bam-rITRDNdeI which hence contained a unique NdeI site. Next a PCR was performed with oligonucleotides "NY-up" and "NY-down" (FIG. 2). During amplification, both a NdeI and a NsiI restriction site were introduced to facilitate cloning of the amplified fiber DNAs. Amplification consisted of 25 cycles of each 45 sec. at 94° C., 1 min. at 60° C., and 45 sec. at 72° C. The PCR reaction contained 25 pmol of oligonucleotides NY-up or NY-down, 2 mM dNTP, PCR buffer with 1.5 mM MgCl$_2$, and 1 unit of Elongase heat stable polymerase (Gibco, The Netherlands). One-tenth of the PCR product was run on an agarose gel which demonstrated that the expected DNA fragment of ±2200 bp was amplified. This PCR fragment was subsequently purified using Geneclean kit system.(Bio101 Inc.) Then, both the construct pBr/Ad.Bam-rITRDNdeI as well as the PCR product were digested with restriction enzymes NdeI and SbfI. The PCR fragment was subsequently cloned using T4 ligase enzyme into the NdeI and SbfI sites thus generating pBr/Ad.Bam-RDFib (FIG. 3).

Amplification of Fiber Sequences from Adenovirus Serotypes.

To enable amplification of the DNAs encoding fiber protein derived from alternative serotypes degenerate oligonucleotides were synthesized. For this purpose, first known DNA sequences encoding for fiber protein of alternative serotypes were aligned to identify conserved regions in both the tail region as well as the knob region of the fiber protein. From the alignment, which contained the nucleotide sequence of 19 different serotypes representing all 6 subgroups, (degenerate) oligonucleotides were synthesized (See, Table I). Also shown in Table I is the combination of oligonucleotides used to amplify the DNA encoding fiber protein of a specific serotype. The amplification reaction (50 ml) contained 2 mM dNTPs, 25 pmol of each oligonucleotide, standard 1×PCR buffer, 1.5 mM MgCl$_2$, and 1 Unit Pwo heat stable polymerase (Boehringer Mannheim) per reaction. The cycler program contained 20 cycles, each consisting of 30 sec. 94° C., 60 sec. 60–64° C., and 120 sec. 72° C. One-tenth of the PCR product was run on an agarose gel to demonstrate that a DNA fragment was amplified. Of each different template, two independent PCR reactions were performed.

Generation of Chimaeric Adenoviral DNA Constructs

All amplified fiber DNAs as well as the vector (pBr/Ad.BamRDFib) were digested with NdeI and NsiI. The digested DNAs were subsequently run on a agarose gel after which the fragments were isolated from the gel and purified using the Geneclean kit (Bio101 Inc). The PCR fragments were then cloned into the NdeI and NsiI sites of pBr/AdBamRDFib, thus generating pBr/AdBamRFibXX (where XX stands for the serotype number of which the fiber DNA was isolated). The inserts generated by PCR were sequenced to confirm correct amplification. The obtained sequences of the different fiber genes are shown in FIG. 4.

Generation of Recombinant Adenovirus Chimaeric for Fiber Protein.

Figure 5:
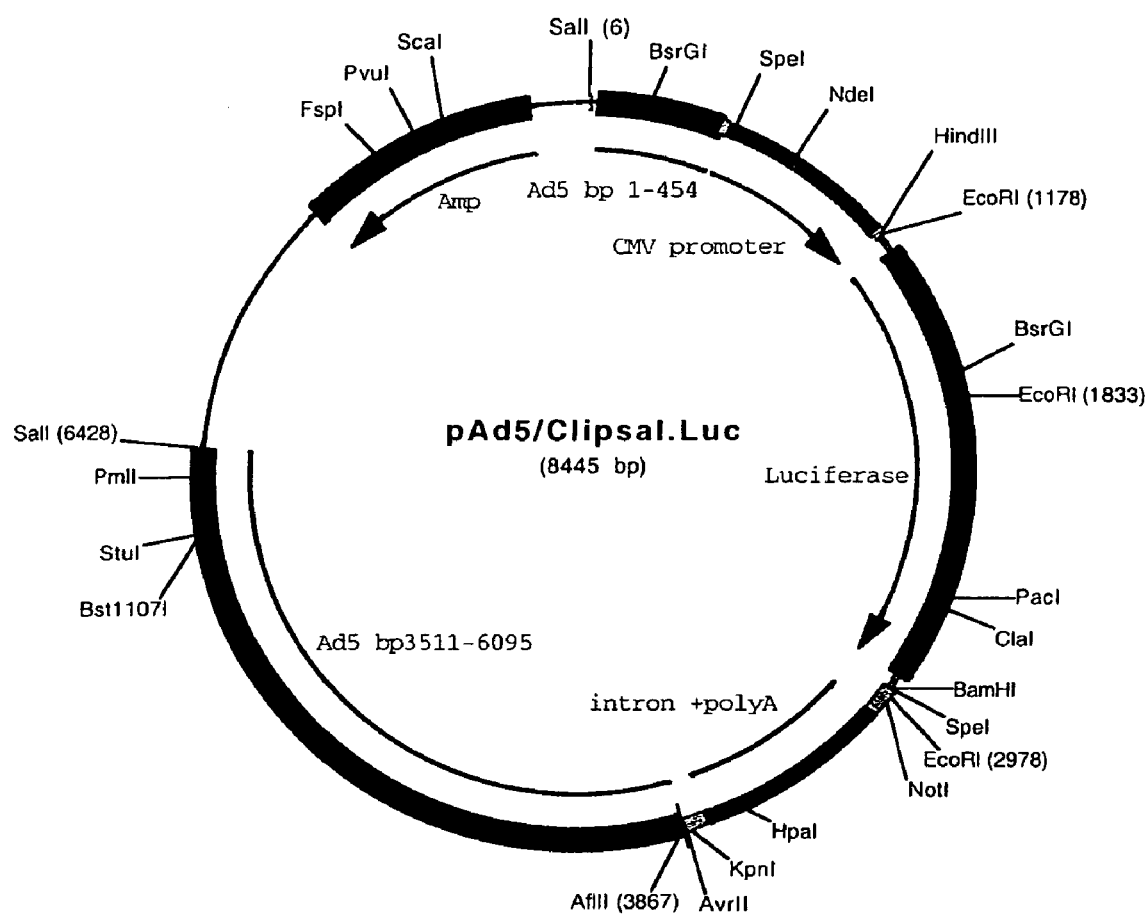
FIG. 5: Schematic drawing of the construct pClipsal-Luc.
Figure 6:
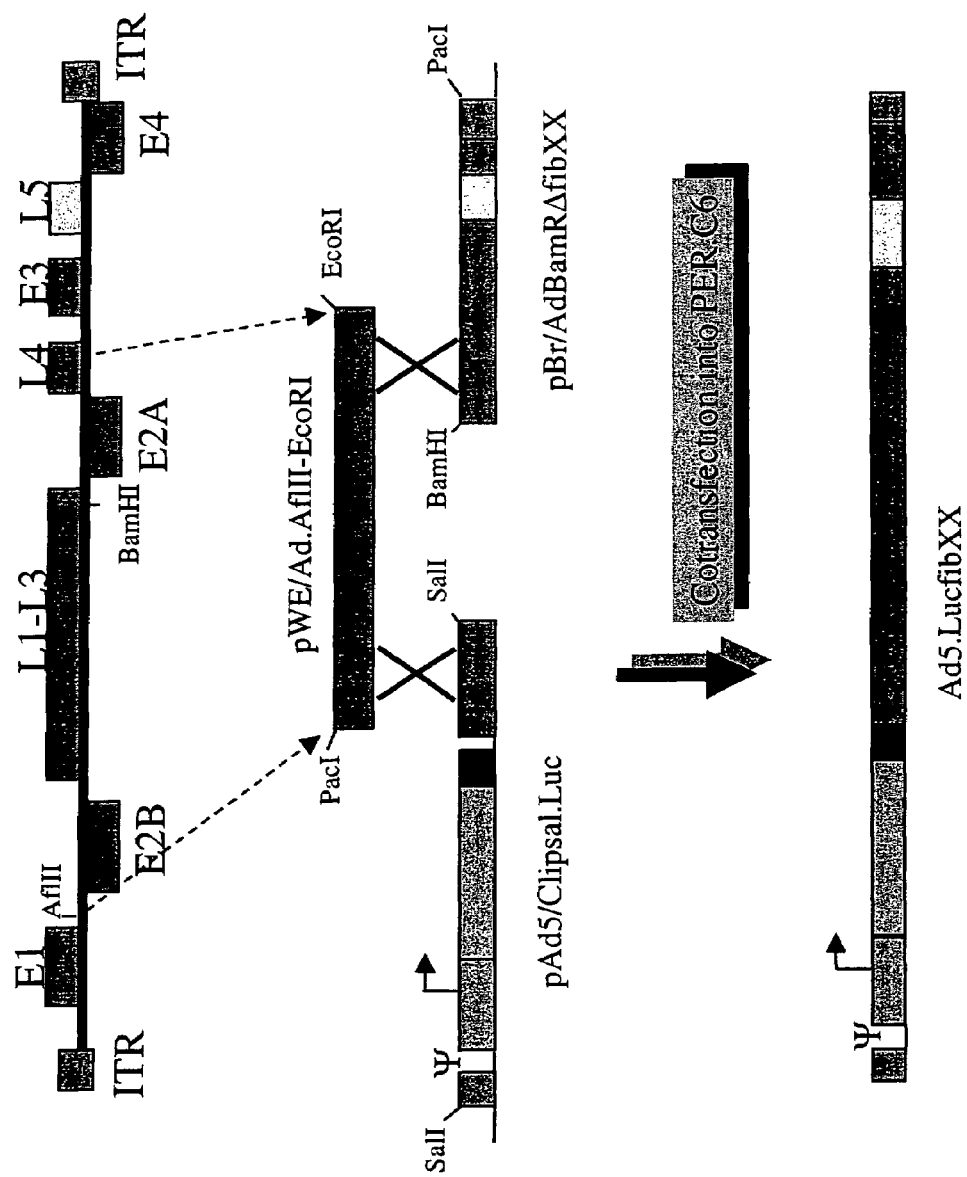
FIG. 6: Schematic drawing of the method to generate chimaeric adenoviruses using three overlapping fragments. Early (E) and late regions (L) are indicated. L5 is the fiber coding sequence.

To enable efficient generation of chimaeric viruses an AvrII fragment from the pBr/AdBamRFib16, pBr/AdBamRFib28, pBr/AdBamRFib40-L constructs was subcloned into the vector pBr/Ad.Bam-rITR.pac#8 (ECACC deposit #P97082121) replacing the corresponding sequences in this vector. pBr/Ad.Bam-rITR.pac#8 has the same adenoviral insert as pBr/Ad.Bam-rITR but has a PacI site near the rITR that enables the ITR to be separated from the vector sequences. The construct pWE/Ad.AflII-Eco was generated as follows. pWE.pac was digested with ClaI and the 5 prime protruding ends were filled in with Klenow enzyme. The DNA was then digested with PacI and isolate from agarose gel. pWE/AflIIrITR was digested with EcoRI and after treatment with Klenow enzyme digested with PacI. The large 24 kb. fragment containing the adenoviral sequences was isolated from agarose gel and ligated to the ClaI digested and blunted pWE.pac vector. Use was made of the ligation express kit from Clontech. After transformation of XL10-gold cells from Stratagene, clones were identified that contained the expected construct. pWE/Ad.AlfII-Eco contains Ad5 sequences from base pairs 3534–27336. Three constructs, pClipsal-Luc (FIG. 5) digested with SalI, pWE/Ad.AflII-Eco digested with PacI and EcoRI and pBr/Ad-BamR.pac/fibXX digested with BamHI and PacI were transfected into adenovirus producer cells (PER.C6, Fallaux et al., 1998). FIG. 6 schematically depicts the method and fragments used to generate the chimaeric viruses. Only pBr/Ad.BamRfib12 was used without subcloning in the PacI containing vector and therefore was not liberated from vector sequences using PacI but was digested with ClaI which leaves approximately 160 bp of vector sequences attached to the right ITR. Furthermore, the pBr/Ad.BamR-fib12 and pBr/Ad.BamRfib28 contain an internal BamHI site in the fiber sequences and were therefor digested with SalI which cuts in the vector sequences flanking the BamHI site. For transfection, 2 mg of pCLIPsal-Luc, and 4 mg of both pWE/Ad.AflII-Eco and pBr/AdBamR.pac/fibXX were diluted in serum free DMEM to 100 ml total volume. To this DNA suspension 100 ml 2.5× diluted lipofectamine (Gibco) in serum-free medium was added. After 30 minutes at room temperature the DNA-lipofectamine complex solution was added to 2.5 ml of serum-free DMEM which was subsequently added to a T25 cm² tissue culture flask. This flask contained PER.C6 cells that were seeded 24-hours prior to transfection at a density of 1×10⁶ cells/flask. Two hours later, the DNA-lipofectamine complex containing medium was diluted once by the addition of 2.5 ml DMEM supplemented with 20% fetal calf serum. Again 24 hours later the medium was replaced by fresh DMEM supplemented with 10% fetal calf serum. Cells were cultured for 6–8 days, subsequently harvested, and freeze/thawed 3 times. Cellular debris was removed by centrifugation for 5 minutes at 3000 rpm room temperature. Of the supernatant (12.5 ml) 3–5 ml was used to infect again PER.C6 cells (T80 cm² tissue culture flasks). This re-infection results in full cytopathogenic effect (CPE) after 5–6 days after which the adenovirus is harvested as described above.

Production of Chimaeric Adenoviruses 10 ml of the above crude cell lysate was used to inoculate a 1 liter fermentor which contained 1–1.5×10⁶ PER.C6 cells/ml growing in suspension. Three days after inoculation, the cells were harvested and pelleted by centrifugation for 10 min at 1750 rpm at room temperature (RT). Adenovirus present in the pelleted cells was subsequently extracted and purified using the following downstream processing protocol. The pellet was dissolved in 50 ml 10 mM $NaPO_4^-$ and frozen at −20° C. After thawing at 37° C., 5.6 ml deoxycholate (5% w/v) was added. The solution was mixed and incubated for 15 minutes at 37° C. to completely lyse the cells. After homogenizing the solution, 1875 ml 1M $MgCl_2$ and 5 ml glycerol was added. After the addition of 375 ml DNase (10 mg/ml) the solution was incubated for 30 minutes at 37° C. Cell debris was removed by centrifugation at 1880×g for 30 minutes at RT without brake. The supernatant was subsequently purified from proteins by extraction with FREON (3×). The cleared supernatant was loaded on a 1M TRIS/HCl buffered cesium chloride block gradient (range: 1.2/1.4 gr/ml) and centrifuged at 21000 rpm for 2.5 hours at 10° C. The virus band is isolated after which a second purification using a 1M TRIS/HCl buffered continues gradient of 1.33 gr/ml of cesium chloride was performed. The virus was then centrifuged for 17 hours at 55000 rpm at 10° C. The virus band is isolated and sucrose (50% w/v) is added to a final concentration of 1%. Excess cesium chloride is removed by dialysis (three times 1 hr at RT) in dialysis slides (Slide-a-lizer, cut off 10000 kDa, Pierce, USA) against 1.5 ltr PBS supplemented with $CaCl_2$ (0.9 mM), $MgCl_2$ (0.5 mM) and an increasing concentration of sucrose (1, 2, 5%). After dialysis, the virus is removed from the slide-a-lizer after which it is aliquoted in portions of 25 and 100 ml upon which the virus is stored at −85° C.

To determine the number of virus particles per ml, 50 ml of the virus batch is run on an high pressure liquid chromatograph (HPLC) as described by Shabram et al. (1997) using a 300–600 mM NaCl gradient. The virus titer of the chimaeric virus was found to be in the same range as the Ad5.Clip.Luc virus batch (Ad5.Clip.Luc: $2.2 \times 10^{11}$ vp/ml; Ad5.Luc-fib16: $3.1 \times 10^{12}$ vp/ml).

Example 2

Biodistribution of Chimaeric Viruses after Intravenous Tail Vein Injection of Rats.

To investigate the biodistribution of the chimaeric adenovirus Ad5.Luc-fib16 in comparison to Ad5 based luciferase viruses, $1 \times 10^{10}$ particles of each of the virus batches were diluted to 1 ml with PBS and the virus was injected in the tail vein of adult male Wag/Rij rats (3 rats/virus). Forty-eight hours after the administration of the virus, the rats were sacrificed after which the liver, spleen, lung, kidney, heart and brain were dissected. These organs were subsequently mixed with 1 ml of lysis buffer (1% Triton X-100 in PBS) and minced for 30 seconds to obtain a protein lysate. The protein lysate was tested for luciferase activity and the protein concentration was determined. The results, shown in Table II, demonstrate that the Ad5 is targeted for a large part to the liver and to the spleen, whereas the Ad5.Luc-fib16 chimeric virus is not. This experiment shows that it is possible to circumvent the uptake of adenoviruses by the liver by making use of fibers of other serotypes.

Example 3

Production of Fiber Chimeric Adenovirus

Another batch of Ad5.Luc-fib16 was made by using 10 ml crude extract to inoculate a 1 liter fermentor which contained 1–1.5×10⁶ cells/ml PER.C6 that were specifically adapted to grow in suspension. Three days after inoculation, the cells were harvested and pelleted by centrifuging for 10 min at 1750 rpm at room temperature. The chimeric adenovirus present in the pelleted cells was subsequently extracted and purified using the following downstream processing protocol. The pellet was dissolved in 50 ml 10 mM $NaPO_4^-$ and frozen at −20° C. After thawing at 37° C., 5.6 ml deoxycholate (5% w/v) was added after which the solution was homogenized. The solution was subsequently incubated for 15 minutes at 37° C. to completely crack the cells. After homogenizing the solution, 1875 μl (1M) $MgCl_2^-$ was added and 5 ml 100% glycerol. After the addition of 375 μl DNase (10 mg/ml) the solution was incubated for 30 minutes at 37° C. Cell debris was removed by centrifugation at 1880×g for 30 minutes at room temperature without the brake on. The supernatant was subsequently purified from proteins by loading on 10 ml of FREON. Upon centrifugation for 15 minutes at 2000 rpm without brake at room temperature three bands are visible of which the upper band represents the adenovirus. This band was isolated by pipetting after which it was loaded on a TRIS/HCl (1M) buffered cesium chloride block gradient (range: 1.2 to 1.4 gr./ml). Upon centrifugation at 21000 rpm for 2.5 hours at 10° C., the virus was purified from remaining protein and cell debris since the virus, in contrast to the other components, does not migrate into the 1.4 gr./ml cesium chloride solution. The virus band is isolated after which a second purification using a TRIS/HCl (1M) buffered continues gradient of 1.33 gr./ml of cesium chloride is performed. After virus loading on top of this gradient, the virus is centrifuged for 17 hours at 55.000 rpm at 10° C. Subsequently, the virus band is isolated and after the addition of 30 μl of sucrose (50 w/v) excess cesium chloride is removed by three rounds of dialysis, each round comprising of 1 hour. For dialysis the virus is transferred to dialysis slides (Slide-a-lizer, cut off 10.000 kDa, Pierce, USA). The buffers used for dialysis are PBS which are supplemented with an increasing concentration of sucrose (round 1 to 3: 30 ml, 60 ml, and 150 ml sucrose (50% w/v)/1.5 liter PBS, all supplemented with 7.5 ml 2% (w/v) $CaMgCl_2$). After dialysis, the virus is removed from the slide-a-lizer after which it is aliquoted in portions of 25 and 100 µl upon which the Ad5.Luc-fib16 virus is stored at −85° C.

To determine the number of virus particles per milliliter, 50 µl of the virus batch is run on a high-pressure liquid chromatograph (HPLC). The adenovirus is bound to the column (anion exchange) after which it is eluted using a NaCl gradient (range 300–600 mM). By determination of the area under the virus peak the number of virus particles can be calculated. To determine the number of infectious units (IU) per ml present in a virus batch, titrations are performed on 911 cells. For this purpose, $4 \times 10^4$ 911 cells are seeded per well of 96-well plates in rows B, D, and F in a total volume of 100 µl per well. Three hours after seeding the cells are attached to the plastic support after which the medium can be removed. To the cells a volume of 200 µl is added, in duplicate, containing different dilutions of virus (range: $10^2$ times diluted to $2 \times 10^9$). By screening for CPE the highest virus dilution which still renders CPE after 14 days is considered to contain at least one infectious unit. Using this observation, together with the calculated amount of virus volume present in these wells renders the number of infectious units per ml of a given virus batch.

Example 4

Chimeric Viruses Display Differences in Synoviocyte Cell Transduction

Infection of Human Synoviocytes

Figure 8:
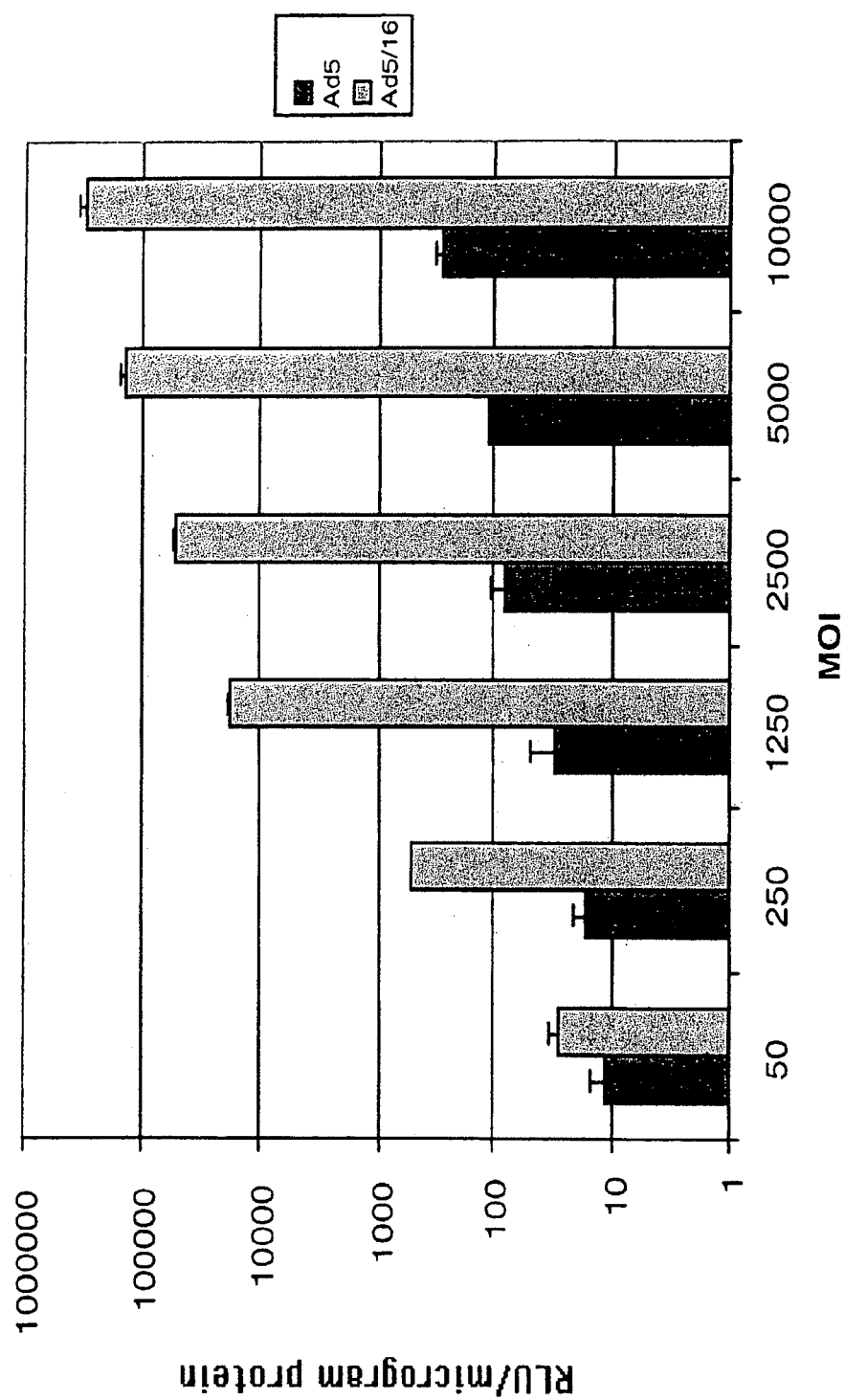
FIG. 8: Infection of synoviocytes using different amounts of virus particles per cell (MOI) and two different adenoviruses: Ad5=Ad5.Clip.Luc; Ad5/16=Ad5.Luc-fib16. Luciferase transgene expression, 48 hours after a 2 hours infection procedure is depicted as relative light units (=RLU) per microgram whole cell lysate. Error bars represent standard error of the mean (SEM).

In a first set of experiments, 50.000 synoviocytes (derived from 1 individual) were seeded in each well of a 24-wells plate in a volume of 1 ml per well. Twenty-four hours after seeding, the cells were washed with PBS after which 200 µl of DMEM supplemented with 2% FCS was added to the cells. This medium contained various amounts of virus (a multiplicity of infection (MOI) of 50, 250, 1250, 2500, 5000, and 10000 vp/cell was used). Viruses were either Ad5.Clip.Luc or Ad5.Luc-fib16. Two hours after addition of virus the medium was replaced by normal medium thus removing the non-bound virus (each infection in duplicate). Again forty-eight hours later cells were washed and lysed by the addition of 100 µl lysis buffer after which luciferase transgene expression was monitored. In FIG. 8, results are shown of the luciferase transgene expression per microgram protein after infection of synoviocytes. These results show that the fiber 16 chimeric adenovirus infects synoviocytes significantly better, based on transgene expression, as compared to the control Ad5. The fold increase of the fiber 16 chimeric adenovirus over the control Ad5 ranged, depending on the MOI used, from 2.4× (MOI 50) to 1052× (MOI 10000). Identical experiments demonstrated on average (n=4) at least a factor 100 difference in transgene expression between the Ad5 and the fiber 16 chimeric adenovirus.

Figure 9:
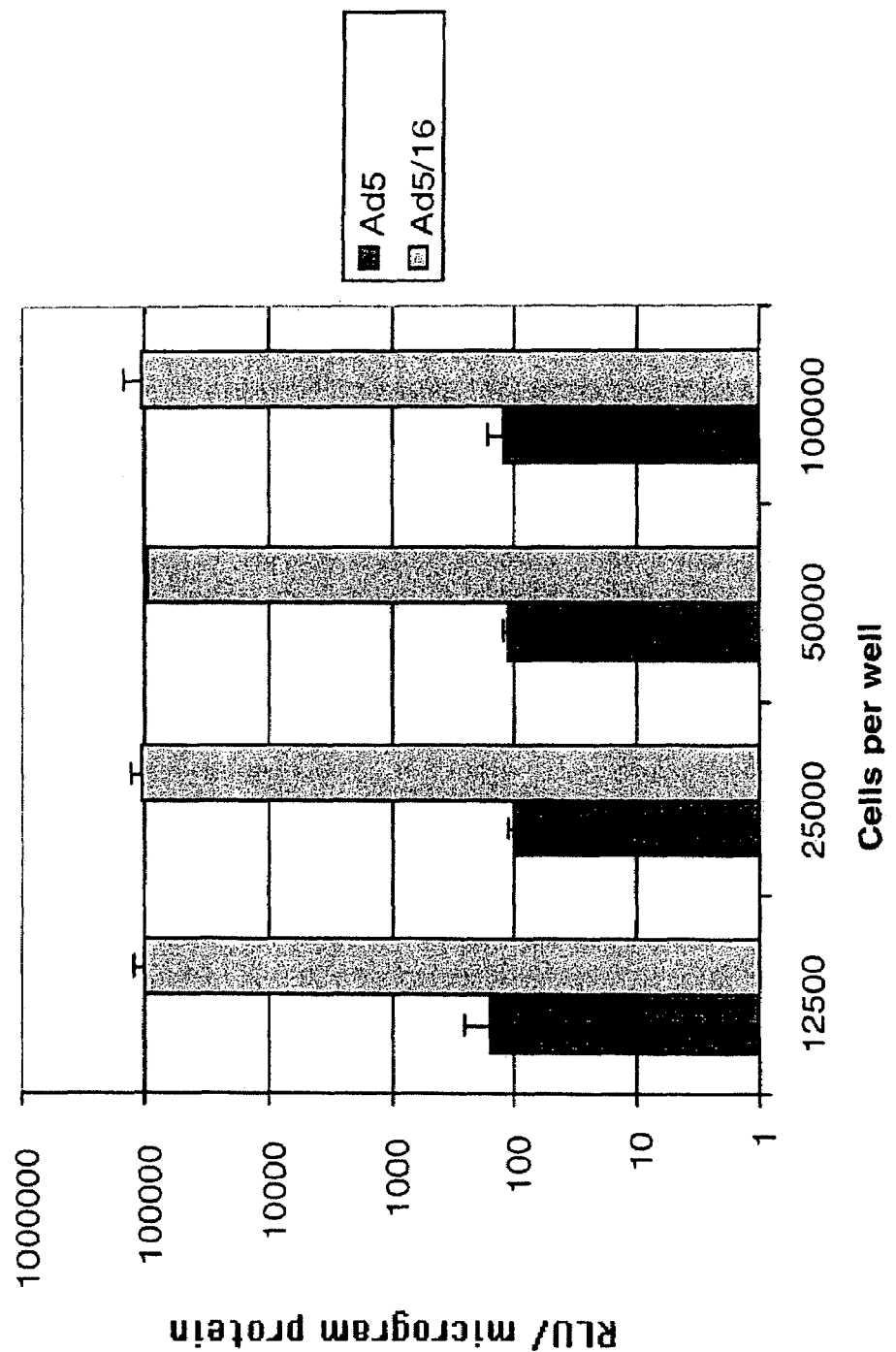
FIG. 9: Infection of synoviocytes using different concentrations of cells. Luciferase transgene expression, 48 hours after a 2 hours infection procedure is depicted as relative light units (=RLU) per microgram total protein. Error bars represent SEM. The actual MOI differed between the cell concentrations and ranged from 20,000 virus particles per cell (cell density 12,500) to 2,500 virus particles per cell (cell density 100,000).

In a second set of experiments, an equal number of virus particles was added to different concentrations of synoviocytes. This experiment was performed since it is possible that the efficiency of infection of these cells is dependent on the confluency of the synoviocyte cell layer. A highly confluent cell layer may mimic the in vivo situation better. For this purpose, synoviocytes were seeded at concentrations of 12.500, 25.000, 50.000, and 100.000 cells per well of 24-well plates (in duplicate). Twenty-four hours later these cells were infected as described above with medium containing $2.5 \times 10^8$ virus particles. The result of the luciferase transgene expression determined 48 hours after a two hours infection procedure (See, FIG. 9) shows that the fiber 16 chimeric adenovirus renders a ±1000 fold higher expression of luciferase and thus is clearly better suited to infect synoviocytes also when cells are 100% confluent.

Figure 10:
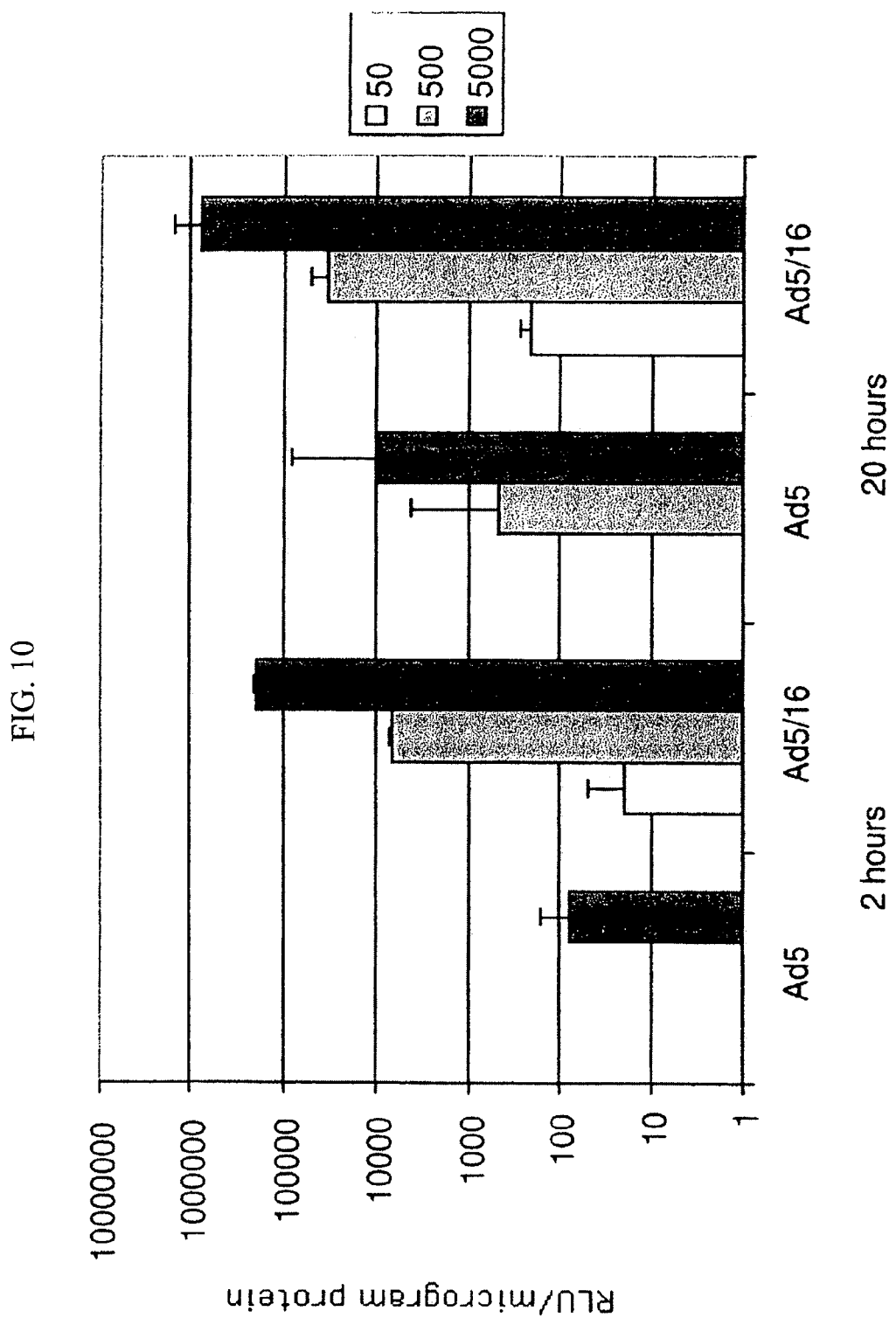
FIG. 10: Infection of synoviocytes using different virus exposure periods. Luciferase transgene expression, 48 hours after either a 2 hours or a 20 hours virus exposure is depicted as relative light units (=RLU) per microgram protein. Error bars represent standard deviations.

In a third set of experiments, we determined the differences in the level of luciferase transgene expression versus the time of virus exposure. This experiment was performed to demonstrate that the binding kinetics of the fiber 16 chimeric adenovirus is different from that of the Ad5 control virus. For this purpose, 15.000 synoviocytes were seeded in 24-well plates in a volume of 1 ml. Twenty-four hours later, cells were infected (in triplicate) with an MOI of 50, 500, or 5.000 vp/cell infection was allowed to proceed either for two hours or for 20 hours. The results, shown in FIG. 10, demonstrate that binding kinetics and characteristics of the fiber 16 chimeric adenovirus is distinct from that of the control Ad5 and that the fiber 16 chimeric adenovirus infects synoviocytes much more efficient as compared to the control Ad5 virus.

From the described results, it is clear that the fiber 16 chimeric virus is better suited to infect synoviocytes as compared to the Ad5. Since it is known that Ad5 requires the coxacki adenovirus receptor ("CAR") and the integrins $\alpha_v\beta3$ and $\alpha_v\beta5$ for entry, we monitored expression of these molecules on synoviocytes using flow cytometry. For this purpose, $1 \times 10^5$ synoviocytes were transferred to tubes designed specifically for flow cytometry. Cells were washed once with PBS/0.5% BSA after which the cells were pelleted by centrifugation for 5 minutes at 1750 rpm at room temperature. Subsequently, 10 µl of a 100 times diluted $\alpha_v\beta3$ antibody (Mab 1961, Brunswick Chemie, Amsterdam, NL), a 100 times diluted antibody $\alpha_v\beta5$ (antibody (Mab 1976, Brunswick chemie, Amsterdam, NL), or 2000 times diluted CAR antibody (a gift from Dr. Bergelson, Harvard Medical School, Boston, USA (Hsu et al., 1988) was added to the cell pellet after which the cells were incubated for 30 minutes at 4° C. in a dark environment. After this incubation, cells were washed twice with PBS/0.5% BSA and again pelleted by centrifugation for 5 minutes at 1750 rpm room temperature. To label the cells, 10 µl of rat-anti-mouse IgG1 labeled with phycoerythrine (PE) was added to the cell pellet upon which the cells were incubated for 30 minutes at 4° C. in a dark environment. Finally, the cells were washed twice with PBS/0.5% BSA and analyzed on a flow cytometer. The results of this experiment are shown in Table III.

These flow cytometric results demonstrate that synoviocytes do not express detectable levels of CAR, which may be at least one of the reasons that these cells are difficult to transduce with the Ad5.

As a control for the experiments performed on synoviocytes, A549 and PER.C6 cells were infected. These cell lines can be readily infected by Ad5. This experiment is performed to investigate whether the observed differences on the synoviocytes can indeed be attributed to differences in cell binding or that the differences are caused by differences in virus particle per infectious unit ratio. For this purpose, $10^5$ A549 cells were seeded in 24-well plates in a volume of 200 µl. Two hours after seeding the medium was replaced by medium containing different amounts of particles of either Ad5.Luc-fib16 or Ad5.Clip.Luc (MOI=0, 5, 10, 25, 100, 500). Twenty-four hours after the addition of virus, the cells were washed once with PBS after which the cells were lysed by the addition of 100 µl lysis buffer to each well (1% Triton X-100 in PBS) after which transgene expression (luciferase activity) and the protein concentration was determined.

Subsequently, the luciferase activity per µg protein was calculated. These data, shown in Table IV, demonstrate that when using a identical amount of virus particles, differences in transgene expression observed in relevant cell types is due to differences in binding and/or internalization of the virus and not to the amount of virus used.

A similar experiment was performed on PER.C6 cells using Ad5 and the fiber chimera fiber 16. For this purpose, $10^5$ PER.C6 cells, were seeded in 24-wells plates in a total volume of 100 µl. Three hours after seeding, the medium was replaced by medium containing $10^6$ particles of either Ad5.Clip.Luc or Ad5.Luc-fib16 (MOI=10). Twenty-four hours after addition of the virus, cells were washed once with PBS after which 100 µl lysis buffer was added to the attached cells. The lysate was subsequently used to determine transgene expression (luciferase activity) and the protein concentration. The results, shown in Table V, again demonstrate that the differences in infection efficiency as observed on synoviocytes, in favor of the fiber 16 chimeric adenovirus, are differences related to binding efficiency rather than to the amount of virus used.

Example 5

Treatment of RA with HSV TK

Materials and Methods

Recombinant Adenoviral Vectors:

The adenoviral vectors used in this study contain the recombinant gene inserted into the E1 region of an Ad type 5 mutant. The cytomegalovirus promoter ("CMV") and the major late promoter ("mlp") were used to drive gene expression in the constructs harboring the lacZ and luciferase marker genes. Mlp was used to drive gene expression in the Ad harboring the TK gene. Virus concentrations were determined by titration of the virus. Ad were tested to contain no replication competent wild-type Ad or E1 a recombination. The adenoviral vectors IG.Ad.CMV.lacZ, IG.Ad.mlp.lacZ, IG.Ad.CMV.luc, IG.Ad.mlp.luc and IG.Ad.mlp-I. TK and their production have been previously described in detail (Imler et al.; Vincent et al., 1996).

Synovial Fibroblast Culture.

Human synovium was obtained from patients with RA defined by ARA-criteria 1987 (Arnett et al., 1988) at the time of joint replacement surgery. Synovial tissue was collected in sterile Phosphate Buffered Saline (PBS). Fat and connective tissue were discarded and tissue was incubated with 0.5 mg collagenase/ml for 2 h at 37 EC. Cells were washed and seeded in 75-cm² flasks in 10 ml of Iscoves Modified Dulbeco's Medium (IMDM) 17% fetal calf serum (FCS). Medium was refreshed twice a week. Confluent cultures of adherent synoviocytes were passaged at a 1:2 ratio in 75-cm² flasks. The cells were detached from the flasks with 1.5 ml 0.25% trypsin-EDTA dissolved in PBS at room temperature.

Infections:

The day prior to infections, synovial cells were plated at a density of 100,000 per 25-cm² bottle in reporter gene experiments or 5,000 per well (24 wells plate) in TK experiments. Cells were cultured in respectively 10 or 1 ml of IMDM 17% FCS. In the procedure of infection of synoviocytes, medium was replaced by the appropriate dose of modulated virus in IMDM 17% FCS.

LacZ In-Vitro Experiments:

After 2 days of incubation the number of synoviocytes were counted in a negative control and in a sample incubated with virus concentration multiplicity of infection (MOI) 100. Remaining samples were washed with PBS, fixed briefly with glutaraldehyde 0.25%, washed with PBS (2×) and stained by immersion in 5 mM $K_4Fe(CN)_6$, 5 mM $K_3Fe(CN)_6$, 2 mM $MgCl_2$ in PBS containing 0.5 mg/ml of X-gal stain (5-bromo-4-chloro-3-indolyl-8-D-galactopyranoside; Sigma Chemical Co., St. Louis, Mo., USA). After four to six hours samples were washed twice and the reaction was stopped by glutaraldehyde 0.25% Percentage of infected cells was assessed by light microscopy after counting at least 300 cells (magnification 110×40).

Luciferase In-Vitro Experiments:

After 3 days of incubation with Ad.luc synoviocyte counts were made comparable to lacZ experiment. Remaining samples were washed with PBS and trypsinized briefly. Synoviocytes were lysed using 200:1 lysis buffer. Samples of 20:1 were analyzed by luminometric methods.

TK In-Vitro Experiments:

One day after incubation with Ad.TK medium was replaced by IMDM 40% Normal Human Serum ("NHS"). In half of the cultures 10 µg GCV (9-[1,3-dihydrate-2-propoxy] methyl]guanine, Roche Nederland BV, NL) was added per ml medium. Medium plus or minus GCV was refreshed on day 3. Cells counts were made 5 days after virus infection.

In the TK-bystander killing experiment, one 75-cm² flask with synoviocytes was trypsinized and divided over three flasks. Two flasks were infected with respectively IG.Ad-.mlpI.TK or IG.Ad.CMV.TK. One day later infected and non-infected cells were mixed according to scheme (See, FIG. 14). Medium was replaced by IMDM 40% NHS plus or minus GCV. Cell counts were made after 7 days.

Animals and Intra-Articular Injections:

All animal protocols were approved by the Medical Ethical Committee and performed according to institutional guidelines. 8 Adult rhesus monkeys (*Macaca mulatta*) suffering from CIA (Bakker, 1992) were used for these experiments and held under D2 containment. Before handling, monkeys were anaesthetized with a single intramuscular dose of approximately 1 ml of 85–90% ketamine [100:1/kg, 10 mg/ml] (ASP Pharma BV Oudewater, NL) and 10–15% vetranquil. If an animal was experiencing severe pain it was given twice a day 0.06 mg Burprenorfine (Temgesic-R, Schering-Plough BV, Amstelveen, NL).

Before intra-articular punction the area surrounding knees was shaved and rinsed with iodine. Using sterile technique, respectively 1 ml or 0.1 ml of purified recombinant virus suspended in PBS was injected according to scheme into the intra-articular space of the knee or proximal interphalangeal joint (pip). Beginning forty-eight hours after injection of the virus, monkey 7 and 8 received 10 mg/kg GCV infused in half an hour, daily for fourteen days. Animals were killed by intracordial punction and bleeding. For summary of rhesus monkeys experiments see Table VI Parameters Animals were monitored daily for general health, which included recording of behavior, appetite and stool consistency. Evaluation of biochemical parameters was performed on a number of days after virus administration (See, Table VI). For this purpose, animals were sedated as described above, body weight and rectal temperature were measured and venous blood samples were collected [clotted and sodium ethylenediamine tetra-acetic acid (EDTA)-treated blood]. Analysis of the blood serum included electrolytes (Na, K, Cl and bicarbonate); kidney function (urea, creatinine) and liver function [alkaline phosphatase, asparagine-aminotransferase (ASAT), alanine-aminotransferase (ALAT); lactate dehydrogenate (LDH) and total bilirubin]; total protein and albumin; and hematological parameters (red and white blood cell counts, differential count, platelet count, erythrocyte sedimentation rate (ESR). In monkey 5–8 venous blood was drawn in clot tubes and analyzed for the presence of antibodies against Ad by complement fixation assay, according to routine procedures at the department of infectious diseases and immunology (SSDZ Delft, NL).

Feces, urine and pharyngeal swabs were collected on different sampling days (See, Table VI) and stored frozen. Analysis consisted of culturing extracts on 293 cells (growth of wild-type and recombinant virus) and hep-2 cells (growth of wild-type virus)(Bout et al., 1994).

A complete post-mortem necropsy and histopathological examination of aorta, axillary lymph nodes, bladder, colon, duodenum, hart, inguinal lymph nodes, lung, liver, lymph nodes of the lung hilus, spleen, left kidney, esophagus, pancreas, thyroid gland, skeleton muscle, bone marrow, thymus, trachea, cervix/vagina and ovary or prostate and testis were performed. Samples of these tissues were fixed in 10% phosphate buffered formalin for routine histopathological analysis.

In addition in monkey 1–5 snap frozen samples of axillary lymph nodes, hart, inguinal lymph nodes, liver, spleen, left kidney, lung, bladder, esophagus, bone marrow and synovium injected joints and non-injected control joints were taken for luciferase assay (Sawchuk, 1996). Joints were opened, colored with X-gal staining solution (Roessler et al., 1993; Bout et al., 1993) and post-fixed in formalin for at least 72 hours. Joints were cut using a diamond saw, subsequently pieces were imbedded in plastic and 6: slices were cut using a microtome. Slices were stained with haematoxylin and eosin according to standard procedures at the pathological laboratory of Leiden University Hospital, The Netherlands.

Results

In-Vitro

Possibility of Gene Transfer to Synoviocytes

Synoviocytes were infected with modified Ad using different reporter genes and different promoters. Two days after infection of synoviocytes with IG.Ad.CMV.lacZ at MOI 100, 67% cells were positive for X-gal, as evidenced by a microscopically visible blue color of the cells. In synovial cell cultures a doses response relation was observed between the amount of virus added and gene expression of the reporter gene, both after infection with IG.Ad.CMV.lacZ and IG.Ad.CMV.luc (See, Table XI and Table XII). When incubation time was prolonged to five days, 100% of synoviocytes stained blue. Gene expression after infection with Ad constructs driven by the CMV promoter is higher than by Ad constructs driven by the mlp-promoter. This difference is more prominent using lacZ as a reporter gene (±100×) than using luciferase as a reporter gene (±10×). Two days after infection with IG.Ad.mlp.lacZ at MOI 100, less than 1% was positive for lacZ. However, clear gene expression in a dose dependent fashion was observed if the luciferase reporter gene was used (Table XII).

Toxicity of Gene Transfer to Synoviocytes.

To assess possible toxicity of high doses Ad for synoviocytes, synoviocytes were cultured without virus or incubated with Ad.lacZ, Ad.luc or Ad.TK at MOI 100. Cell counts of synoviocyte cultures after infection with modified Ad at MOI 100 showed no significant differences compared to non-infected cultures (Table VII). Students t-test for paired samples $p>0.2$.

Efficacy of Cell-Killing.

Figure 11:
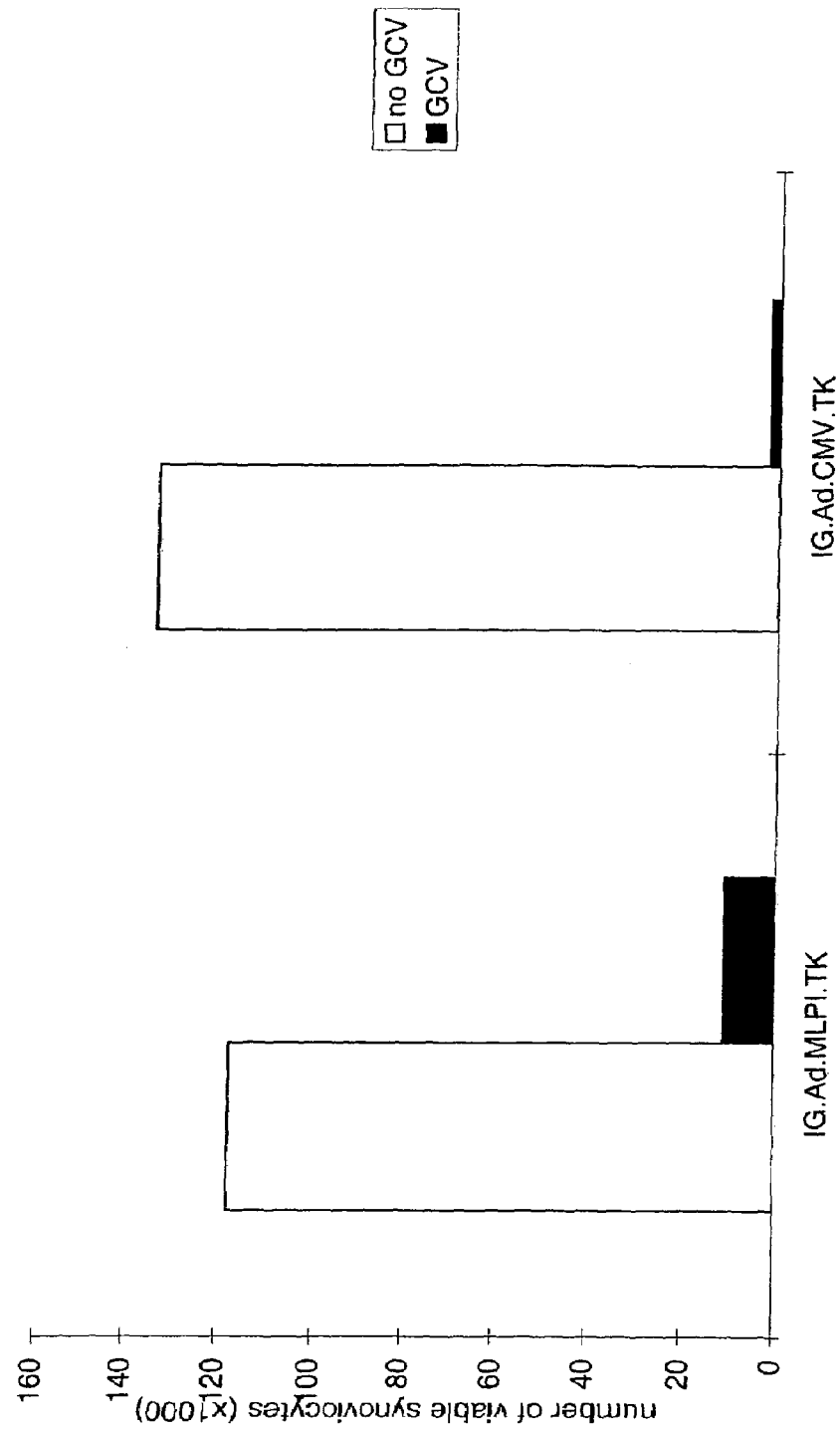
FIG. 11: Synoviocytes were incubated with IG.Ad.CM-V.TK or IG.Ad.mlp-I.TK. Cells were cultured with or without GCV.
Figure 12:
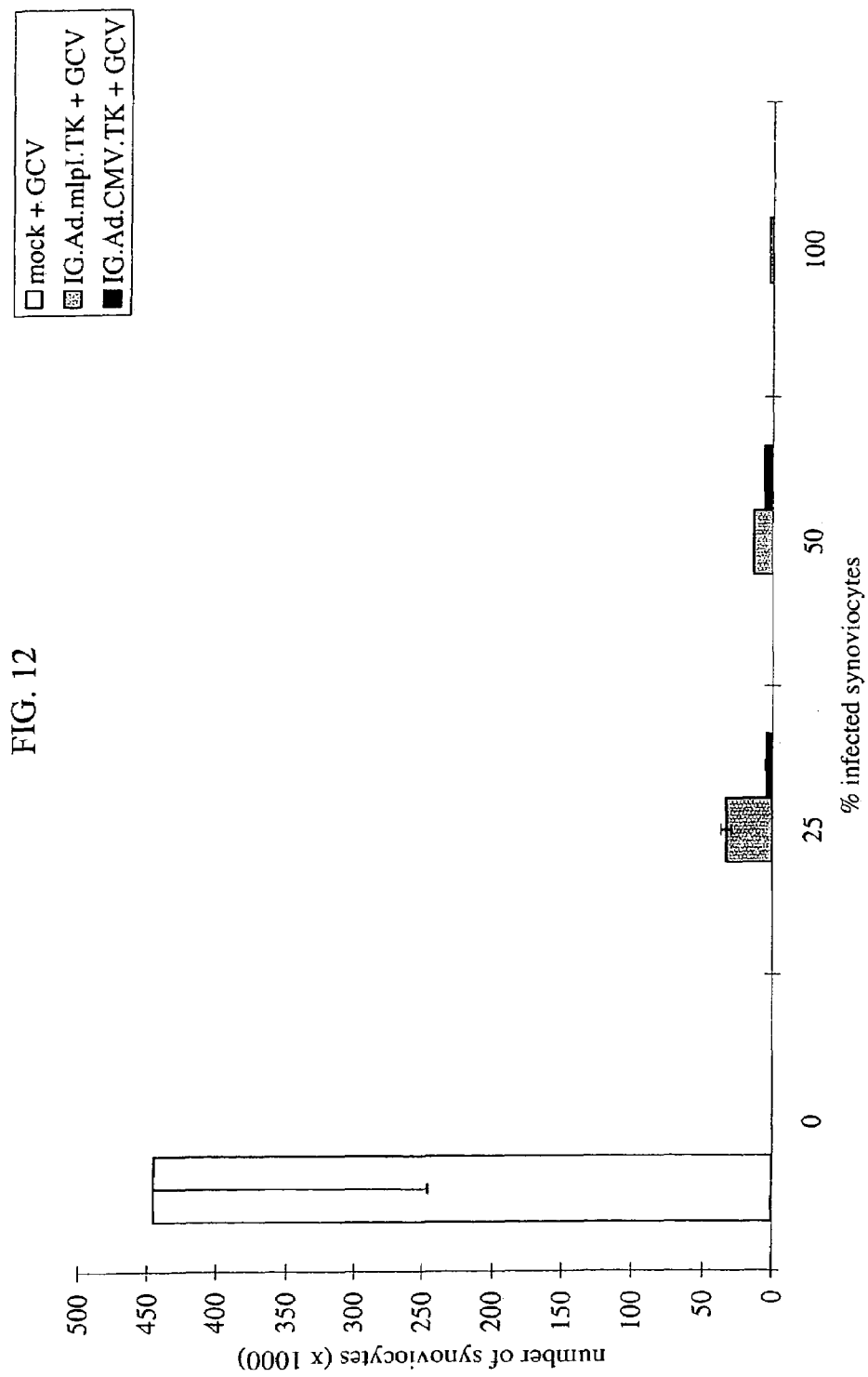
FIG. 12: Bystander killing was assessed in cultures containing both TK-infected and non-TK-infected synoviocytes in a proportion 0/100, 50/50, 25/75 and 0/100. Cells were cultured with or without GCV.

Synoviocytes incubated with IG.Ad.mlp.TK were cultured with or without 10:mg/ml GCV. 99 percent cell killing was observed after infection of synoviocytes with IG.Ad.CMV.TK and incubation with GCV, infection with IG.Ad.mlp.TK led to 80% cell killing (See, FIG. 11). After mixing 25% transduced with 75% untransduced synoviocytes, bystander killing was assessed. Both in IG.Ad.CMV.TK and IG.Ad.mlp.TK experiments extensive cell killing was observed (See, FIG. 12).

In-Vivo:

Possibility and specificity of gene transfer to inflamed synovial tissue in-vivo:

36 joints (10 knees and 26 pip's) of 8 different monkeys were injected with different amounts of IG.Ad.lacZ, IG.Ad.luc or IG.Ad.mlp-I.TK. In the biodistribution experiments, a CMV promoter was chosen to allow maximum sensitivity in detection of reporter gene product.

Figure 13A:
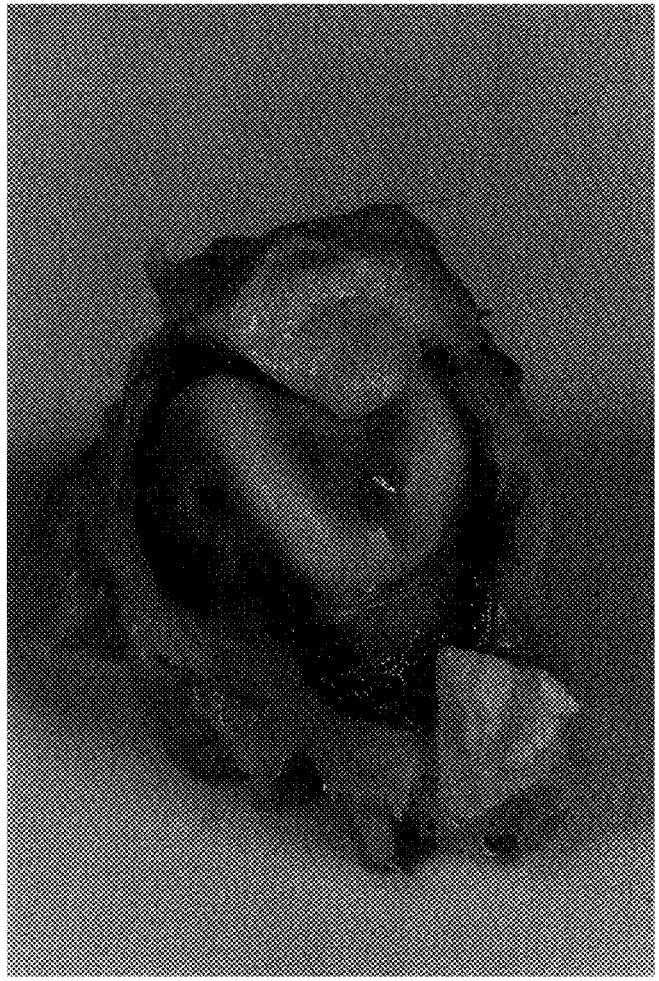
FIGS. 13A & 13B: X-gal expression in synovial tissue 3 days after intra-articular injection of IG.Ad.CMV.lacZ in the knee. 13A: macroscopy. 13B: direct LacZ staining of synovial tissue counterstained with Mayers Hamalanlosung.
Figure 13B:
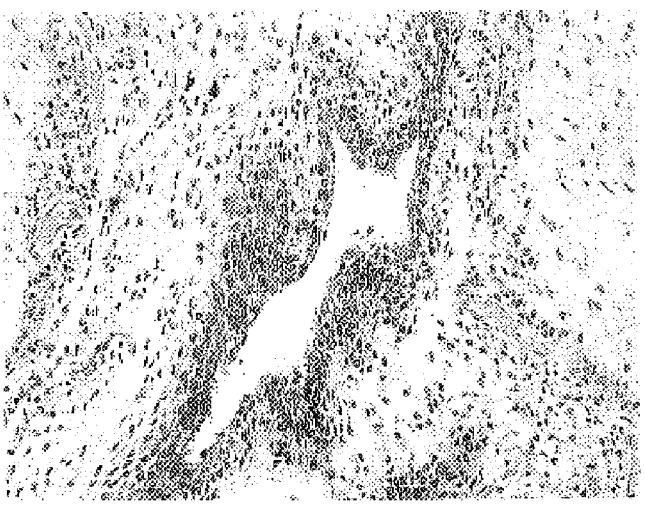

Histological examination of articular and peri-articular tissues obtained 2–3 days after infection with IG.Ad.CMV.lacZ showed lacZ expressing cells present in synovial villi as well as in the synovial tissue covering tendons, bone, articular cartilage and subsynovial adipose tissue (FIG. 13). The cells expressing lacZ activity were synoviocytes as evidenced by typical location and morphologic appearance. The percentage of infected cells ranged from 5 to 70%. Joints injected with PBS and non-injected joints did not show any lacZ positive cells. No infection of cartilage, bone, fat or muscle tissue was observed. If the less efficient mlp promoter was used (in monkey 5 and in pip 2 monkey 2) no lacZ positive cells could be found.

Dose Response After Gene Transfer to Synoviocytes In-Vivo

In monkey 4 and 5 increasing amounts of modified Ad were injected in consecutive pip-joints in the monkeys. In the pip-joints of monkey 4, injected with IG.Ad.CMV.lacZ, an obvient dose-response relation was observed in percentage of lacZ expressing cells (Table VIII). In monkey 5, injected with IG.Ad.mlp.lacZ, no lacZ positive cells were observed in the synovium.

Toxicity of Intra-Articular (i.a.) Administration of Ad Harboring a Reporter Gene Biodistribution To assess toxicity of the procedure, biodistribution of the virus was determined using Ad harboring the luciferase reporter gene. Luciferase-activity, measured by luminometric methods, indicates infection of the organ by Ad. Monkey 1–5 were injected by Ad.CMV.luc or IG.Ad.mlp.luc and were sacrificed 2–3 days after virus administration. Specimens of synovial tissue were harvested. From the same biopsies histological confirmation was obtained to judge if the sample contained relevant tissue. In monkey 4 the samples contained mainly connective tissue and no synovial tissue. Samples of above mentioned organs and joints were analyzed using the luciferase assay. Samples obtained from a non-treated monkey were used as a control. Except for one sample (cervix) and two non-virus injected joints that had slightly elevated luciferase counts, only IG.Ad.luc injected joints were positive in the luciferase assay (Table IX).

To assess shedding of the virus excreta were cultured during the first 3 days of the experiment. In the feces (day 0–3) of monkey 5 Ad could be cultured both on 293- and hep-2 cells. The throat swab of this monkey was positive on 293 cells on day 1. In the other monkey's feces, urine and throat swabs were negative in the Ad culture assay.

Clinical Behavior.

During the experiment, monkeys 3 and 5 suffered from severe arthritis, which made climbing difficult and led to diminished appetite and weight loss. One monkey that suffered from severe arthritis had a slightly elevated body temperature up to 40° C. Analyses on blood samples indicated increase in CRP, thrombocytosis, hypalbuminaemia and anemia related to the presence of arthritis symptoms. A small increase in LDH-levels was observed (Table X).

Histopathological analysis showed synovitis, moderate chronic pleuritis, necrotizing dermatitis, mild-chronic enteritis and inguinal and axillary lymphadenopathy in all monkeys. In order to analyze local inflammation induced by the procedure of i.a. administration of Ad, non-injected, saline-injected and Ad-injected joints were compared by routine histopathological analysis. No significant differences were observed in synovial hyperplasia or lymphocyte infiltration.

Toxicity of i.a. Administration of Ad Harboring the Suicide Gene TK.

During the TK-experiments, monkeys were closely observed to detect any toxicity of the procedure. The behavior of the monkeys, clinical observations, biochemical parameters and histopathological analysis did only show abnormalities as has been reported before in monkeys with CIA. No additional toxicity was seen in suicide gene treated groups as compared to reporter gene treated groups. Histopathological analysis revealed no differences except for multifocal mid-zonal and peripheral infiltrations with lymphocytes and plasma cells in the liver of monkey 6 with single hepatocellular necrosis.

Effectiveness of suicide gene transfer to inflamed synovial tissue can be seen as local toxicity of the procedure. Histopathological analysis of the injected joint revealed no differences in synovial hyperplasia or lymphocyte infiltration compared to control joints. Joint circumference diminished 1 cm in knees injected with IG.Ad.mlp-I.TK followed by GCV and 1 to 1.5 cm in non-injected knees.

In monkeys 6, 7 and 8 who were terminated 14 to 18 days after intra-articular injection, a turn in antibody titer from negative to positive was observed after day 5–7. No viruses were cultured from the excreta.

Example 6

Plasmid-Based System for Rapid RCA-Free Generation of Recombinant Adenoviral Vectors Construction of Adenovirus Clones 1. pBr/Ad.Bam-rITR (ECACC Deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LMP agarose gel (Sea Plaque GTG). After transformation into competent E. coli DH5α (Life Techn.) and analysis of ampicillin resistant colonies, one clone was selected that showed a digestion pattern as expected for an insert extending from the BamHI site in Ad5 to the right ITR.

Sequence analysis of the cloning border at the right ITR revealed that the most 3' G residue of the ITR was missing, the remainder of the ITR was found to be correct. The missing G residue is complemented by the other ITR during replication.

2. pBr/Ad.Sal-rITR (ECACC Deposit P97082119)

pBr/Ad.Bam-rITR was digested with BamHI and SalI. The vector fragment including the adenovirus insert was isolated in LMP agarose (Sea Plaque GTG) and ligated to a 4.8 kb SalI-BamHI fragment obtained from wt Ad5 DNA and purified with the Geneclean II kit (Bio 101, Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3' G residue).

3. pBr/Ad.Cla-Bam (ECACC Deposit P97082117)

wt Adeno type 5 DNA was digested with ClaI and BamHI, and the 20.6 kb fragment was isolated from gel by electroelution. pBr322 was digested with the same enzymes and purified from agarose gel by Geneclean. Both fragments were ligated and transformed into competent DH5α. The resulting clone pBr/Ad.Cla-Bam was analyzed by restriction enzyme digestion and shown to contain an insert with adenovirus sequences from bp 919 to 21566.

4. pBr/Ad.AflII-Bam (ECACC deposit P97082114)

Clone pBr/Ad.Cla-Bam was linearized with EcoRI (in pBr322) and partially digested with AflII. After heat inactivation of AflII for 20' at 65° C. the fragment ends were filled in with Klenow enzyme. The DNA was then ligated to a blunt double stranded oligo linker containing a PacI site (5'-AATTGTCTTAATTAACCGCTTAA-3') (SEQ ID NO:1). This linker was made by annealing the following two oligonucleotides: 5'-AATTGTCTTAATTAACCGC-3' (SEQ ID NO:2) and 5'-AATTGCGGTTAATTAAGAC-3'(SEQ ID NO:3), followed by blunting with Klenow enzyme. After precipitation of the ligated DNA to change buffer, the ligations were digested with an excess PacI enzyme to remove concatameres of the oligo. The 22016 bp partial fragment containing Ad5 sequences from bp 3534 up to 21566 and the vector sequences, was isolated in LMP agarose (Sea Plaque GTG), religated and transformed into competent DH5α. One clone that was found to contain the PacI site and that had retained the large adeno fragment was selected and sequenced at the 5' end to verify correct insertion of the PacI linker in the (lost) AflII site.

5. pBr/Ad.Bam-rITRpac#2 (ECACC Deposit P97082120) and pBr/Ad.Bam-rITR#8 (ECACC Deposit P97082121)

To allow insertion of a PacI site near the ITR of Ad5 in clone pBr/Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2', 5', 10' and 15'). The extend of nucleotide removal was followed by separate reactions on pBr322 DNA (also digested at the ClaI site), using identical buffers and conditions. Bal31 enzyme was inactivated by incubation at 75° C. for 10', the DNA was precipitated and resuspended in a smaller volume TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples Generation of Adapter Plasmids and Recombinant Adenoviruses.

Generation of the Adapter Plasmid pMLPI.TK

Adapter plasmid pMLPTK (EPO patent application 95202213) was modified as follows: SV40 polyA sequences were amplified with primer SV40-1 (introduces a BamHI site) and SV40-2 (introduces a BglII site). In addition, Ad5 sequences present in this construct (from nt. 2496 to nt. 2779; Ad5 sequences nt. 3511 to 3794) were amplified with primers Ad5-1 (introduces a BglII site) and Ad5-2.

| | | |
|---|---|---|
| SV40-1: | 5'-GGG<u>GGATCC</u>GAACTTGTTTATTGCAGC-3' | (SEQ ID NO:4) |
| SV40-2: | 5'-GGG<u>AGATCT</u>AGACATGATAAGATAC-3' | (SEQ ID NO:5) |
| Ad5-1: | 5'-GGG<u>AGATCT</u>GTACTGAAATGTGTGGGC-3' | (SEQ ID NO:6) |
| Ad5-2: | 5'-GGAGGCTGCAGTCTCCAACGGCGT-3' | (SEQ ID NO:7) | treated for 10' or 15'. The 10' or 15' treated pBr/Ad.Bam-rITR samples were then ligated to the above described blunted PacI linkers (See, pBr/Ad.AflII-Bam). Ligations were purified by precipitation, digested with excess PacI and separated from the linkers on an LMP agarose gel. After religation, DNAs were transformed into competent DH5α and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

pWE/Ad.AflII-rITR (ECACC deposit P97082116)

Cosmid vector pWE 15 (Clontech) was used to clone larger Ad5 inserts. First, a linker containing a unique PacI site was inserted in the EcoRI sites of pWE 15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.Bam-rITR#2 digested with BamHI and PacI. These fragments were ligated together and packaged using λ phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

pWE/Ad.AflII-EcoRI pWE.pac was digested with ClaI and 5' protruding ends were filled using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultracompetent XL10-Gold cells from Stratagene, clones were identified that contained the expected insert. pWE/AflII-EcoRI contains Ad5 sequences from bp 3534–27336.

Both PCR fragments were digested with BglII and ligated. The ligation product was amplified with primers SV40-1 and Ad5-2 and digested with BamHI and AflII. The digested fragment was then ligated into pMLP.TK predigested with the same enzymes. The resulting construct, named pMLPI.TK, contains a deletion in adenovirus E1 sequences from nt. 459 to nt. 3510.

Generation of pAd5/L420.HSA, pAd5/Clip and pAd5/Clipsal pMLPI.TK was used to make a new vector in which nucleic acid molecules comprising specific promoter and gene sequences can be easily exchanged. First, a PCR fragment was generated from pZipΔMo+PyF101(N⁻) template DNA (described in published International Patent Application PCT/NL96/00195) with the following primers: LTR-1: 5'-CTG TAC GTA CCA GTG CAC TGG CCT AGG CAT GGA AAA ATA CAT AAC TG-3' (SEQ ID NO:8) and LTR-2: 5'-GCG GAT CCT TCG AAC CAT GGT AAG CTT GGT ACC GCT AGC GTT AAC CGG GCG ACT CAG TCA ATC G-3'(SEQ ID NO:9). Pwo DNA polymerase (Boehringer Mannheim) was used according to manufacturer's protocol with the following temperature cycles: once 5' at 95° C.; 3' at 55° C.; and 1' at 72° C., and 30 cycles of 1' at 95° C., 1' at 60° C., 1' at 72° C., followed by once 10' at 72° C. The PCR product was then digested with BamHI and ligated into pMLP10 (Levrero et al., 1991; Gene 101, 195–202) digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Sequencing confirmed correct amplification of the LTR fragment however the most 5' bases in the PCR fragment were missing so that the PvuII site was not restored. Next, the coding region of the murine HSA gene was inserted. pLTR10 was digested with BstBI followed by Klenow treatment and digestion with NcoI. The HSA gene was obtained by PCR amplification on pUC 18-HSA (Kay et al., 1990; J. Immunol. 145, 1952–1959) using the following primers: HSA1,5'-GCG CCA CCA TGG GCA GAG CGA TGG TGG C-3'(SEQ ID NO:10), 5'-CTG TAC GTA CCA GTG CAC TGG CCT AGG CAT GGA AAA ATA CAT AAC TG-3' (SEQ ID NO:11) and LTR-2:

5'-GCG GAT CCT TCG AAC CAT GGT AAG CTT GGT ACC GCT AGC GTT AAC CGG GCG ACT CAG TCA ATC G-3'(SEQ ID NO:12) and HSA2,5'-GTT AGA TCT AAG CTT GTC GAC ATC GAT CTA CTA ACA GTA GAG ATG TAG AA-3' (SEQ ID NO:13) 5'-CTG TAC GTA CCA GTG CAC TGG CCT AGG CAT GGA AAA ATA CAT AAC TG-3' (SEQ ID NO:14) and LTR-2: 5'-GCG GAT CCT TCG AAC CAT GGT AAG CTT GGT ACC GCT AGC GTT AAC CGG GCG ACT CAG TCA ATC G-3'(SEQ ID NO:15). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI(sticky)-SalI(blunt) fragment and cloned into the 3.5 kb NcoI(sticky)/BstBI(blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd5/L420-HSA that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from HSA coding region to replace genes in this construct.

Another adapter plasmid that was designed to allow easy exchange of nucleic acid molecules was made by replacing the promoter, gene and polyA sequences in pAd5/L420-HSA with the CMV promoter, a multiple cloning site, an intron and a polyA signal. For this purpose, pAd5/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pAd5/Clip. To enable removal of vector sequences from the adenoviral fragment pAd5/Clip was partially digested with EcoRI and the linear fragment was isolated. An oligo of the sequence 5' TTAAGTCGAC-3' (SEQ ID NO:16) was annealed to itself resulting in a linker with a SalI site and EcoRI overhang. The linker was ligated to the partially digested pAd5/Clip vector and clones were selected that had the linker inserted in the EcoRI site 23 bp upstream of the left adenovirus ITR in pAd5/Clip resulting in pAd5/Clipsal.

Generation of pAd5ClipLacZ, pAd5Clip.Luc, pAd5Clip.TK and pAd5Clipsal.Luc

The adapter plasmid pAd5/Clip.LacZ was generated as follows: The *E. coli* LacZ gene was amplified from the plasmid pMLP.nlsLacZ (EP 95-202 213) by PCR with the primers 5'GGGGTGGCCAGGGTACCTCTAG-GCTTTTGCAA (SEQ ID NO:17) and 5'GGGGGGATC-CATAAACAAGTTCAGAATCC (SEQ ID NO:18). The PCR reaction was performed Ex Taq (Takara) according to the suppliers protocol at the following amplification program: 5 minutes 94° C., 1 cycle; 45 seconds 94° C. and 30 seconds 60° C. and 2 minutes 72° C., 5 cycles; 45 seconds 94° C. and 30 seconds 65° C. and 2 minutes 72° C., 25 cycles; 10 minutes 72; 45 seconds 94° C. and 30 seconds 60° C. and 2 minutes 72° C., 5 cycles, I cycle. The PCR product was subsequently digested with KpnI and BamHI and the digested DNA fragment was ligated into KpnI/BamHI digested pcDNA3 (Invitrogen), giving rise to pcDNA3.nlsLacZ. Next, the plasmid pAd5/Clip was digested with SpeI. The large fragment containing part of the 5' part CMV promoter and the adenoviral sequences was isolated. The plasmid pcDNA3.nlsLacZ was digested with SpeI and the fragment containing the 3'part of the CMV promoter and the lacZ gene was isolated. Subsequently, the fragments were ligated, giving rise to pAd/Clip.LacZ. The reconstitution of the CMV promoter was confirmed by restriction digestion.

The adapter plasmid pAd5/Clip.Luc was generated as follows: The plasmid pCMV.Luc (EP patent application 95-202 213) was digested with HindIII and BamHI. The DNA fragment containing the luciferase gene was isolated. The adapter plasmid pAd5/Clip was digested with HindIII and BamHI, and the large fragment was isolated. Next, the isolated DNA fragments were ligated, giving rise to pAd5/Clip.Luc. The adapter pClipsal.Luc was generated in the same way but using the adapter pClipsal digested with HIII and BamHI as vector fragment. Likewise, the TK containing HIII-BamHI fragment from pCMV.TK (EP patent application 95-202 213) was inserted in pClipsal to generate pAd5/Clip.TK. The presence of the SalI site just upstream of the left ITR enables liberation of vector sequences from the adeno insert. Removal of these vector sequences enhances frequency of vector generation during homologous recombination in PER.C6.

Generation of pWE/Ad.AflII-rITRfib16

To enable convenient generation of recombinant adenoviruses with a Ad5/Ad16 chimeric fiber we cloned the chimeric fiber gene in the place of the Ad5 fiber in the cosmid clone pWE/Ad.AflII-rITR.

The pBr/AdBamRpac.fib16 constructs and the pBr/Ad.AflII-BamHI construct were digested with BamHI and PacI to free it from the pBr plasmid. They were isolated from gel and cleaned by using agarase (Boehringer). The pWE.pac construct was digested with PacI to linearize it and cleaned by phenol/chloroform. A three-point ligation was used in which the BamHI sites of the pBr/AdBamRpac.fib16 constructs and the pBr/Ad.AflII-BamHI construct are ligated together and the pWE.pac construct is ligated at the PacI sites. The ligation mix consists out of the three constructs, T4 ligase, 5 mM ATP and ligation buffer without PEG. 1–4 μl of the ligation mixture, containing 0.1–1.0 μg of ligated DNA, is added to the packaging extract. Separately, 1 μl of the positive wild-type lambda DNA control was packaged. The tubes were spun quickly and incubated at RT for maximum 2 hrs. Respectively 500 μl SM buffer (5.8 g NaCl, 2.0 g $MgSO_4.7H_2O$, 50 ml 1M Tris-HCl (pH 7.5), 5 ml 2% (w/v) gelatin and deionized water up to 1 liter) and 20 μl of chloroform was added to the packaging mixture to stop the reaction. The tube was spun briefly to sediment the debris. The supernatant, which contains the phage, can now be stored at 4° C. up to 1 month.

A bacterial glycerol stock of DH5α strain and VCS257 strain were streaked onto LB agar plates and incubated O/N at 37° C. The next day 10 ml LB medium supplemented with 10 mM $MgSO_4$ and 0.2% (w/v) maltose was inoculated with a single colony of each bacteria strain. This was grown at 37° C. until an $OD_{600}$ value of maximum 1.0 is reached. The bacteria were then pelleted at 500×g for 10 minutes. The pellet is resuspended into 5 ml of sterile 10 mM $MgSO_4$ and diluted in 10 mM $MgSO_4$ till an $OD_{600}$ value of approximately 0.5 is reached.

Of the positive wild-type lambda phage control a $10^{-2}$ and a $10^{-4}$ dilution was made in SM buffer. Of the other final packaged reactions a $10^{-1}$ and a $10^{-2}$ dilution was made in SM buffer. Out of the $10^{-4}$ dilution of the positive control 10 µl was added to 200 µl of VCS257 host cells ($OD_{600}$ 0.5). This is incubated for 15 minutes at 37° C., 3 ml of LB top agar (0.7% agarose in LB medium) (50° C.) is added and immediately plated on a pre-warmed LB agar plate. Out of the $10^{-1}$ and a $10^{-2}$ dilution of the other final packaged reactions 25 µl was added to 25 µl of DH5α a host cells ($OD_{600}$ 0.5). This is incubated for 30 minutes at RT. Respectively 200 µl LB medium is added and an incubation for 1 hr at 37° C. followed. The mixture is spun down shortly, the bacteria pellet is resuspended in 100 µml LB medium and plated on LB agar plates with the required amount of ampicillin. The plates are incubated O/N at 37° C. Eventually the colonies are grown and the required DNA is tested by restriction digestion. pWE/Ad.AflII-rITRfib16 contains all adenovirus type 5 sequences except for the fiber coding region 3' from the NdeI site present in Ad5 fiber, these sequences are replaced by fiber sequences from Ad16 leaving the open reading frame intact.

Generation of Recombinant Viruses With Fiber Modifications

The adapter plasmids pAd5/Clip.TK, pAd5/Clip.LacZ or pAd5/Clip.Luc were digested with SalI to liberate the homologous adenovirus sequences and the left ITR from the vector. pWE/Ad.AflII-rITRfib16 was digested with PacI. DNA was then purified using phenol/chloroform extraction and EtOH precipitation and re-dissolved in sterile transfection qualified water. Four µgr of each construct was transfected into PER.C6 cells in a T25 flask seeded one day before with $2.5 \times 10^6$ cells. At the occurrence of full CPE 6–8 days later cells were harvested in the medium and amplified by infection of 3 ml 3x freeze-thawed cell lysate on fresh PER.C6 cells. At full CPE cells were harvested by freeze-thawing and virus was purified by two rounds of plaque purification on PER.C6 cells. In all cases plaques were positive for transgene expression and one was picked to generate seed stocks for production.

Example 7

Infection of Synoviocytes With Recombinant Adenoviral Vectors in Non-Human Primates Suffering from Collagen Induced Arthritis The transducibility of arthritic synovium by chimeric adenoviruses carrying the LacZ gene from *E. coli*, which codes for the enzyme β-galactosidase, was tested in vivo in a non-human primate model for RA. The rhesus monkey *Maccaca mulatta* was injected 10 times subcutaneously with, in total, 5 mg Bovine Collagen type II (10 mg/ml) emulsified in an equal volume of Complete Freund's Adjuvant. The animal developed a full blown collagen induced arthritis (CIA) within a period of 8 weeks. Subsequently, the left knee was injected intra-articularly with $1*10^{11}$ virus particles (vp) IG.Ad.CLIP.LacZ. The right knee was injected with $1*10^{11}$ vp IG.Ad.ClipLacZ.fib16. The vectors were administered in a total volume of 1 ml diluent (PBS supplemented with 5% sucrose). The site of entry was medially, just below the midpoint of the patella. The needle was introduced in a line towards the suprapatellar pouch. After passing the joint capsule, the vector was injected into the joint cavity. Thereafter, the syringe and needle were removed from the joint. At day 3 post infection, the animal was sacrificed. The left elbow was injected with 1 ml diluent only and served as a negative control. The right elbow was left untreated. The knee joints and elbows were isolated and fixed in phosphate buffered 2% paraformaldehyde/0.25% glutaraldehyde for 3 hours and washed 3 times with PBS, incubated over night in X-Gal solution (5 mM $K_4Fe(CN)_6$, 5 mM $K_3Fe(CN)_6$, 2 mM $MgCl_2$ and 0.5 mg/ml 5-bromo-4-chloro-3-indolyl-8-D-galactopyranoside) and extensively washed with PBS. The hyperplastic synovial lining of the knee joint stained blue with IG.Ad.CLIP.LacZ. However, the knee IG.Ad.ClipLacZ.fib16 injected with stained blue more intensely, showing that recombinant chimeric adenoviruses carrying the fiber of Ad16 infects hyperplastic synovium more efficiently than recombinant adenoviruses carrying fiber of Ad5. Detailed analysis of the transduced tissue confirmed that the number of positive nuclei in the pannus tissue of the IG.Ad.ClipLacZ.fib16 treated joint was significantly higher than the number of positive nuclei found in the IG.Ad.CLIP.LacZ treated joints. Stained nuclei were found several cell layers deep in the pannus tissue. No staining was found in chondrocytes of the cartilage layer or in the diluent or non-injected injected joint. These results show that hyperplastic synovium can be transduced more efficiently with chimeric recombinant IG.Ad.ClipLacZ.fib16 vectors in vivo, as compared to IG.Ad.CLIP.LacZ vectors. Moreover, the results show that the diseased tissue (hyperplastic synovium), but not the chondrocytes (benign cells that are required for cartilage regeneration) were at least preferably transduced by the recombinant adenoviral vectors.

Example 8

Dose Dependent Transduction of Synoviocytes with Recombinant Adenoviral Vectors in Non-Human Primates Suffering from Collagen Induced Arthritis The transducibility of arthritic synovium by chimeric adenoviruses carrying the LacZ gene was tested in a dose escalation study in vivo in the non-human primate model for RA as described above. A monkey suffering from CIA was treated with increasing doses of IG.Ad.CLIP.LacZ or IG.Ad.ClipLacZ.fib16 given intra-articularly in the proximal interphalangeal (pip) in a total volume of 0.1 ml. Pip 2 to 5 were injected with increasing vector doses, ranging from $1 \times 10^7$ to $1 \times 10^{10}$ vp, in the left or right hand, for IG.Ad.CLIP.LacZ or IG.Ad.ClipLacZ.fib16 respectively. As a control, 0.1 ml diluent was injected in pip 1 of both hands. After sacrifice on day 5, the pip joints of the hands were fixed in 2% paraformaldehyde/0.25% and stained with X-GAL to monitor lacZ expression, as described above. A positive correlation was observed between injected dose of LacZ Adenoviruses and the number of lacZ expressing cells in the synovial tissue. Moreover, the IG.Ad.ClipLacZ.fib16 vector treated joints contained more LacZ positive cells than the IG.Ad.CLIP.LacZ treated joints at the same vector dose, confirming that hyperplastic synovium is transduced more efficiently by chimeric recombinant IG.Ad.ClipLacZ.fib16 vectors than by IG.Ad.CLIP.LacZ vectors in a relevant model for rheumatoid arthritis. Microscopy of the injected joints confirmed that the cells expressing lacZ activity were synoviocytes, as evidenced by typical location and morphologic appearance.

Example 9

Killing of Diseased Synovium from Patients Suffering from RA Infected With IG.Ad.CLIP.TK and IG.Ad.CLIP.TK.fib16 Followed by Treatment with GCV In Vitro Synovium was isolated from patients suffering from RA as discussed above. The day prior to infection, $10^4$ synovium cells were plated on a tissue culture dish. The next day, eight dishes with synovial cells were infected with either IG.Ad.CLIP.TK or IG.Ad.CLIP.TK.fib16 at an increasing m.o.i. of 1, 10, 100 and 1000 vp/cell or mock treated. Four hours post infection, the infection medium was replaced by IMDM containing 40% normal human serum supplemented with or without 10 μg/ml GCV. At day 0, 5, 7 and 10 cells were counted. IG.Ad.CLIP.TK.fib infected cells were killed in medium containing GCV more efficiently, especially at lower m.o.i.'s, than IG.Ad.CLIP.TK infected cells, as determined by the decrease in the total cell numbers in these dishes. Neither the mock treated cells, nor the infected cells in medium without GCV were killed, showing that killing was caused by the combination of Ad.TK vectors and GCV. Thus, hyperplastic synovium from patients suffering from RA is sensitive to infection with recombinant IG.Ad vectors expressing TK in combination with treatment with the pro-drug GCV. Moreover, killing of synoviocytes following IG.Ad.CLIP.TK.fib16 infection was more efficient than killing after IG.Ad.CLIP.TK infection in the presence of GCV.

Next, the bystander effect of the treatment was addressed. To that end, synovial cells were infected with IG.Ad.CLIP.TK at an M.O.I. of 100 as described above. The next day, the infected cells were trypsinized and mixed with non-infected synovial cells from the same patient at the ratio of 1:4 (25%) or 1:2 (50%). As controls, non-infected (0%) and non-mixed (100%) cells were included in the experiment. The following 7 days, the cells were cultured in IMDM supplemented with 40% normal human serum and 10 μg/ml GCV and the total amount of cells per dish was determined. The synovial cells infected (100%) with IG.Ad.CLIP.TK were killed. Moreover, the mixed cell populations in which only a percentage of the cells (50% and 25% respectively) was infected with IG.Ad.CLIP.TK were killed too. This shows that human synovium cells that are infected with recombinant IG.Ad vectors expressing the TK gene have a substantial bystander effect following GCV treatment.

Example 10

Killing of Hyperplastic Synovium after Intra-Articular Injection of IG.Ad.CLIP.TK and IG.Ad.CLIP.TK.fib16 Followed by GCV Treatment in Non-Human Primates Suffering from Collagen Induced Arthritis A rhesus monkey was injected 10 times subcutaneously with, in total, 5 mg Bovine Collagen type II (10 mg/ml) emulsified in an equal volume of Complete Freund's Adjuvant to induce CIA. The animal developed a full-blown arthritis within a period of 8 weeks. Subsequently, the left knee was injected intra-articularly with $1\times10^{11}$ vp IG.Ad.CLIP.TK in a total volume of 1 ml diluent. The right knee was injected with $1\times10^{11}$ vp IG.Ad.CLIP.TK.fib16 in a total volume of 1 ml diluent. The sites of entry were medially, just below the midpoint of the patella. The needle was introduced in a line towards the suprapatellar pouch. After the joint capsule was passed, the substances were injected into the knee joint. Thereafter, syringes and needles were removed from the joints. The left elbow was injected with 1 ml diluent and served as a negative control. From day 2 to day 15 the monkey was treated daily intravenously with GCV, 10 mg/kg/day in 25 ml sterile water given in approximately 30 minutes. After sacrifice on day 18 the knees and elbows of the monkey were taken out for histopathological analysis. Synovial biopsies of the knees were snap-frozen in liquid nitrogen and stored at $<-60°$ C.

Cleaving of genomic DNA during apoptosis yields double-stranded low molecular weight nuclear DNA fragments (mono- and oligonucleosomes) as well as single strand breaks ("nicks") in high molecular weight DNA. TUNEL (TdT-mediated dUTP nick end labeling) is a method for enzymatic in situ labeling of apoptosis induced DNA strand breaks. Strand breaks in the DNA can be identified by labeling the free 3'-OH termini of DNA fragments with modified nucleotides in an enzymatic reaction. Terminal deoxynucleotidyl transferase ("TdT"), which catalyses polymerization of nucleotides to the free 3'-OH termini of fragmented DNA, is used as the polymerase. Incorporated fluorescein-12-dUTP is detected by anti-fluorescein antibody Fab fragments from sheep, conjugated with horseradish peroxidase ("POD"). The procedure is extensively described by the supplier (Promega). After substrate reaction, the labeled fragmented genomic DNA were visualized under the light microscope.

The synovial tissue from the elbow that was injected with diluent showed background tissue staining, indicating that some apoptosis has taken place in diseased synovium. In the negative control (no TdT enzyme was added) no staining could be observed. The positive control (a sample that was treated with DNase to induce DNA strand breaks before the TUNEL assay was started) showed staining in all parts of the tissue. The sample from the IG.Ad.CLIP.TK injected joint showed more stained cells than the synovial tissue sample of the diluent treated joint, indicating that more cells went into apoptosis due to the IG.Ad.CLIP.TK-GCV treatment. Most stained cells were found in the joint injected with IG.Ad.CLIP.TK.fib16. The staining was present both in the synovial membrane and in the subsynovial tissue, suggesting that the treatment is efficacious throughout the whole tissue sample. These data show that treatment with recAd vectors expressing the TK gene followed by GCV treatment is a feasible method to perform non-surgical synovectomy in arthritic joints. In addition, these data show that recombinant adenoviral vectors containing fiber 16 are superior in transducing transgenes to synovial tissue.

Example 11

Comparison of Infection of Ad5.luc and Ad5.fib16.luc on RA Synoviocytes

Figure 14:
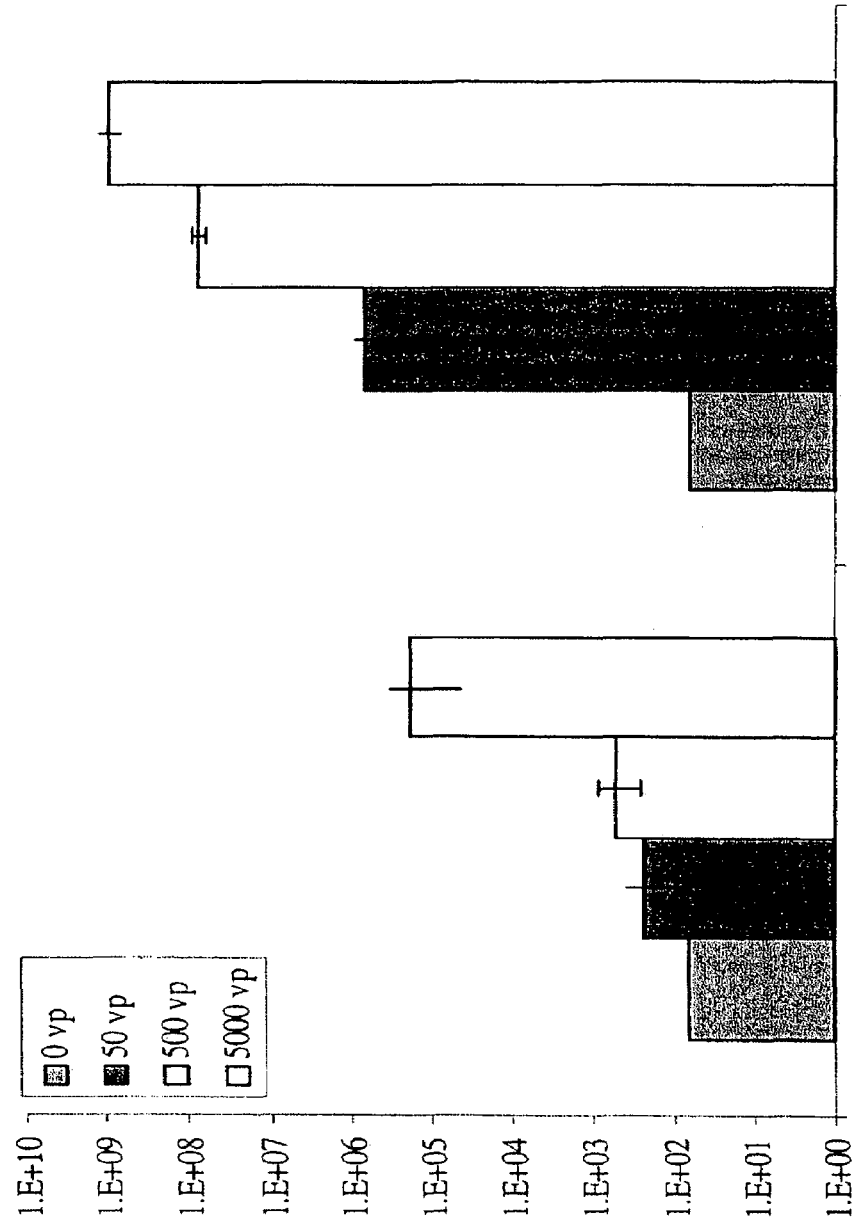
FIG. 14 is a graph comparing infection of Ad5.luc and Ad5.fib16.luc on RA synoviocytes.

In each experiment, a total of 15,000 RA synoviocytes was seeded per well in 12-well microtiter dishes. Cells were infected with Ad5.luc (batch no. IC020-032) or Ad5.fib16.luc (batch no. B204-130C) at various m.o.i.'s, and incubated overnight. Luciferase activity was measured after 72 hours. Data are summarized in Table XIII (FIG. 14).

Example 12

Comparison of Infection of Ad5.lacZ and Ad5.fib16.lacZ on RA Synoviocytes

Figure 15:
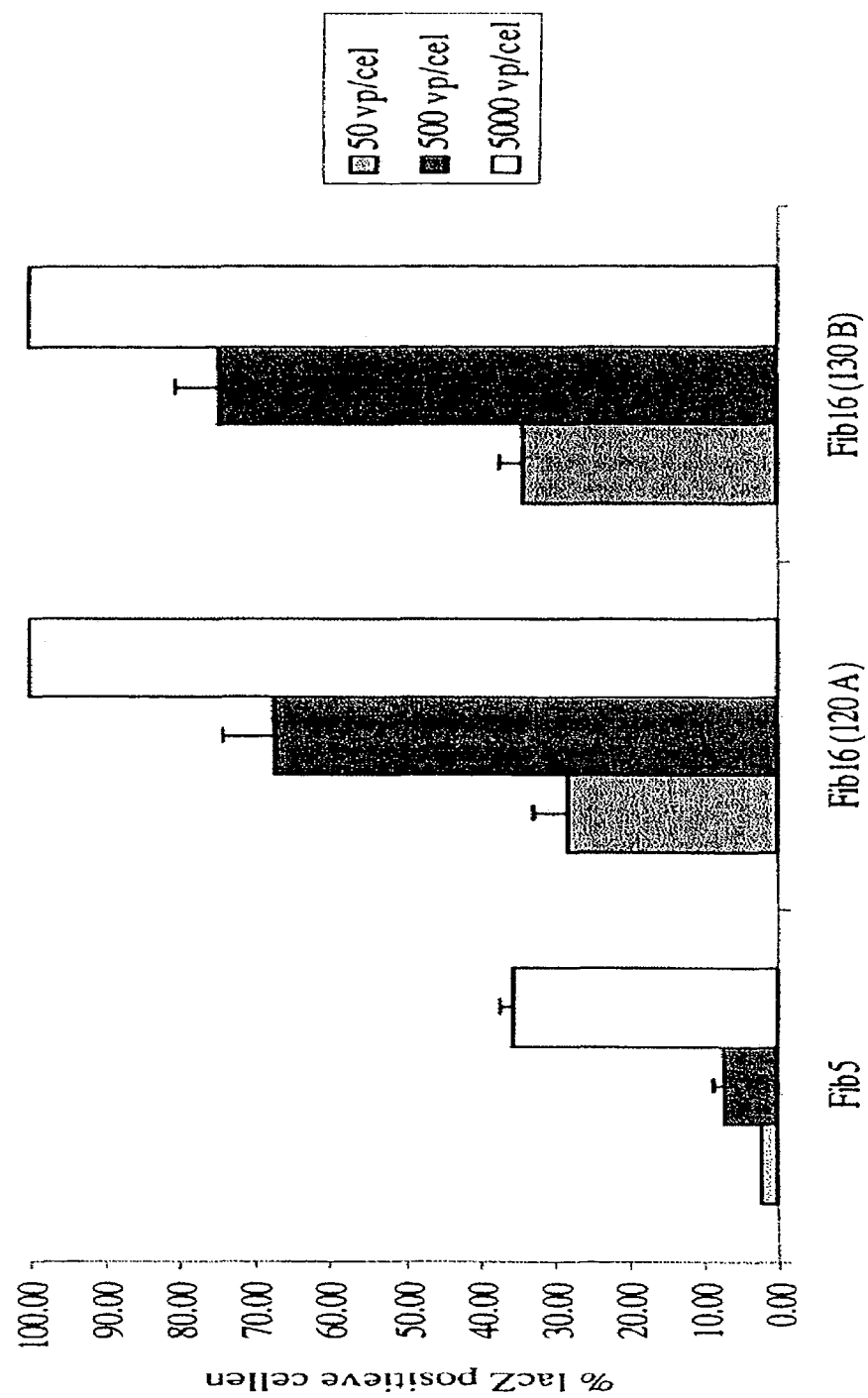
FIG. 15 is a graph depicting the percentage of lacZ positive cells with Ad5.lacZ and Ad5.fib16.lacZ in RA synoviocytes.

In each experiment, a total of 15,000 RA synoviocytes was seeded per well in 12-well microtiter dishes. Cells were infected with Ad5.lacZ (batch no. B269-186) or Ad5.fib16.lacZ (batch nos. B204-120A and B204-120B) at various m.o.i.'s, and incubated overnight. % of lacZ-positive cells was determined after 72 hrs. Data are summarized in Table XIV and FIG. 15.

Example 13

Comparison of Infection of Ad5.GFP and Ad5.fib16.GFP on RA Synoviocytes

Figure 16A:
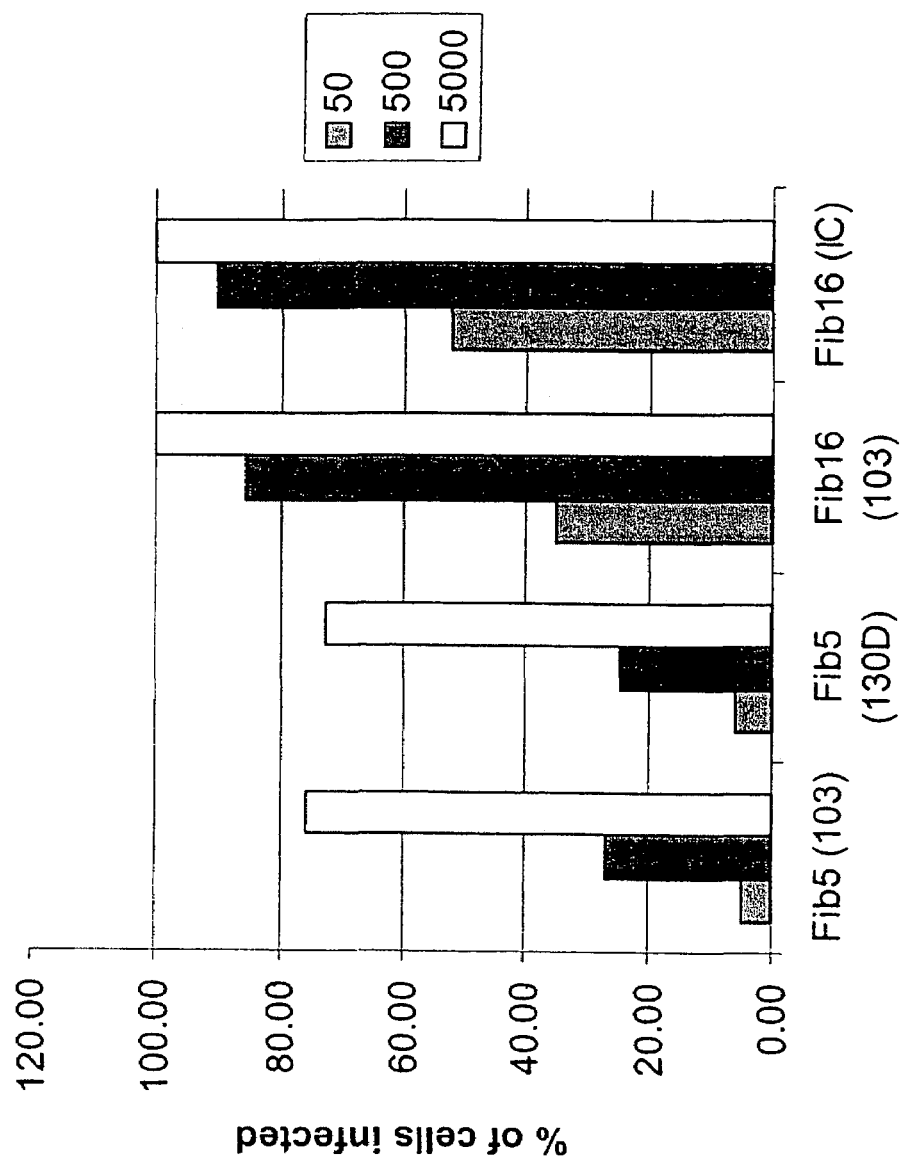

In each experiment, a total of 15,000 RA synoviocytes was seeded per well in 12-well microtiter dishes. Cells were infected with Ad5.GFP (batch no. B204-103 and B204-130D) or Ad5.fib16.GFP (batch nos. B204–103 and IC054-024B) at various m.o.i.'s, and incubated overnight. GFP activity was measured after 72 hrs, and % of GFP-positive cells was determined. Data are summarized in Tables XVa and Xvb and FIGS. 16A and B.

Example 14

Figure 17:
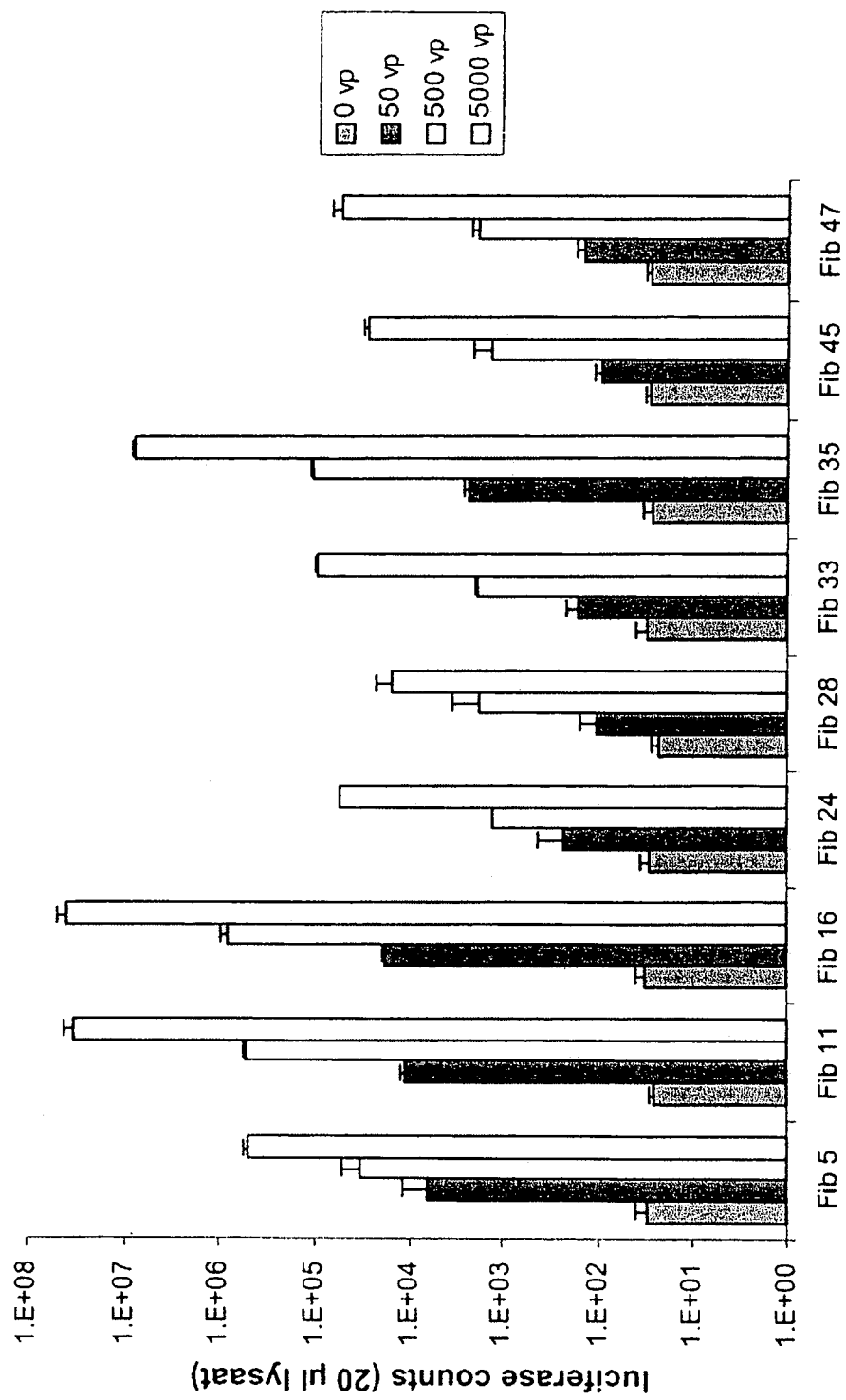
FIG. 17 is a graph depicting the infectivity of chimeric adenoviruses on RA synoviocytes.

Comparison of Infection of Panel of Fiber-Modified Viruses on RA Synoviocytes A panel of chimeric adenoviruses was tested for its infectivity on RA synoviocytes. The following chimeric adenoviruses were produced: Ad5.fib5, 11, 16, 24, 28, 33, 35, 45 and 47, each carrying a luciferase transgene. In each experiment, a total of 15,000 RA synoviocytes was seeded per well in 12-well microtiter dishes. Cells were infected the chimeric adenoviruses at various m.o.i.'s, and incubated overnight. Luciferase activity was measured after 72 hrs. Data are summarized in Table XVI; the graphic representation is in FIG. 17.

Example 15

Figure 18A:
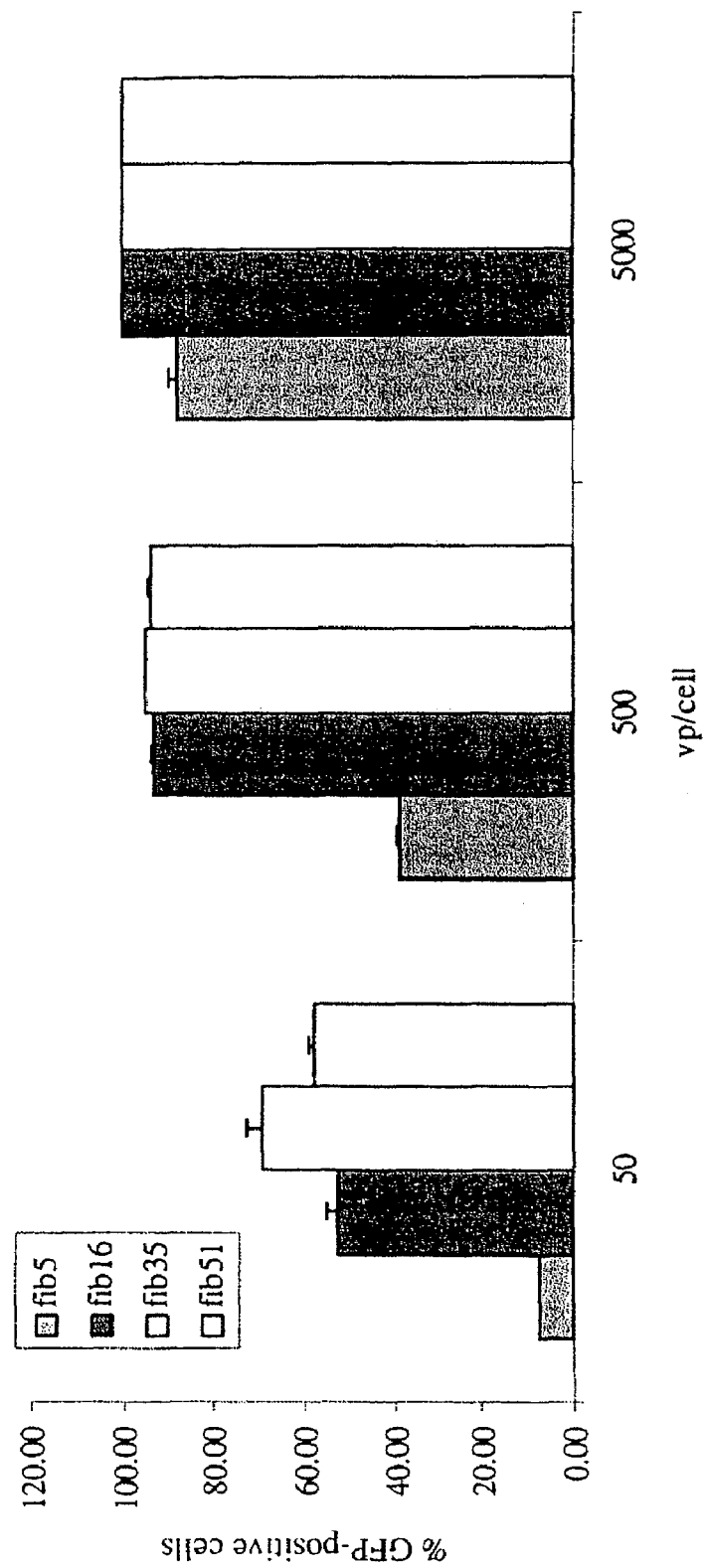
FIG. 18A is a graph depicting the percentage of infected cells with three B-type fiber-modified viruses on RA synoviocytes.
Figure 18B:
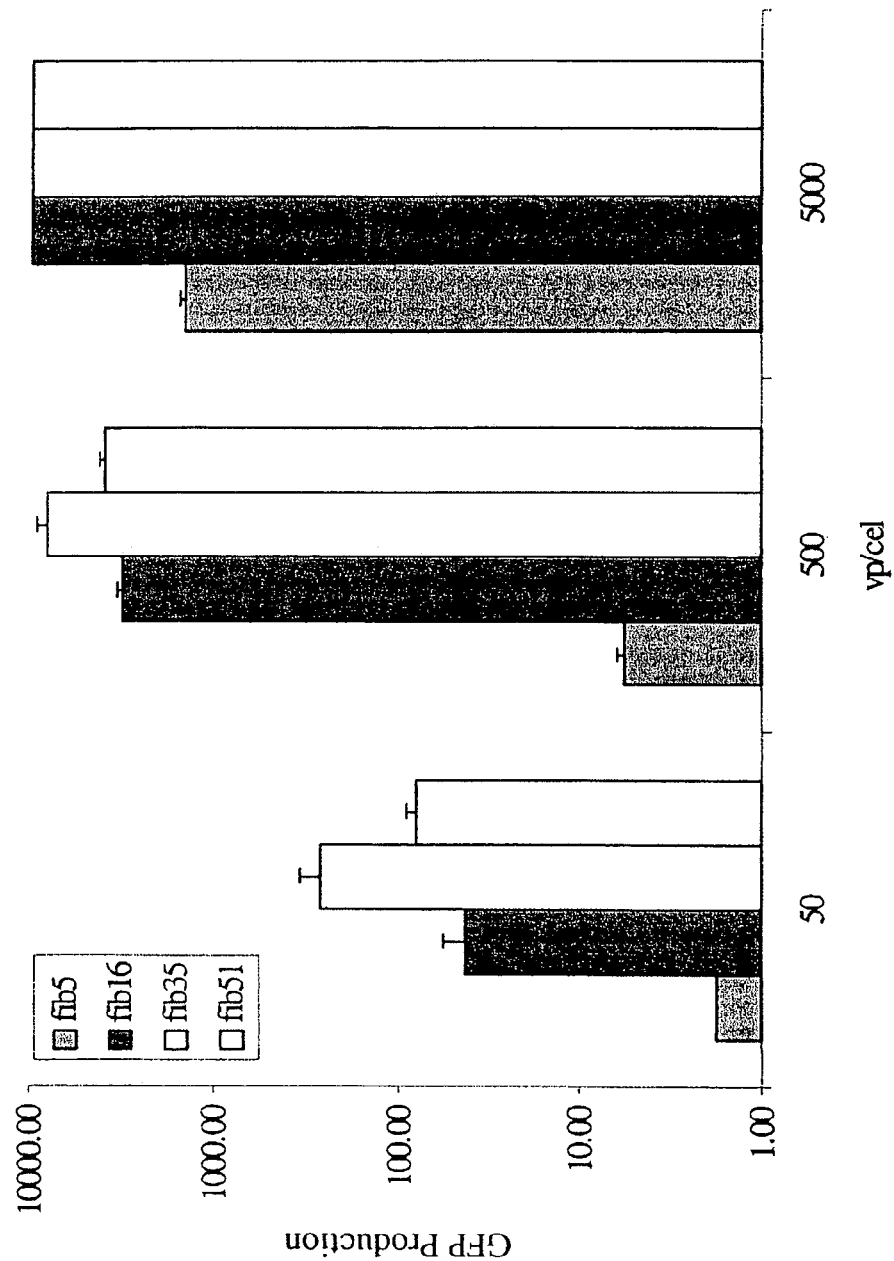
FIG. 18B is a graph depicting GFP production with three B-type fiber-modified viruses on RA synoviocytes.

Comparison of Infection of Three B-Type Fiber-Modified Viruses on RA Synoviocytes Three chimeric adenoviruses, each carrying a B-type fiber were tested for its infectivity on RA synoviocytes, in comparison to Ad5. The following chimeric adenoviruses were produced: Ad5.fib16, 35 and 51, each carrying a GFP transgene. In each experiment, a total of 50,000 RA synoviocytes was seeded per well in 12-well microtiter dishes. Cells were infected the chimeric adenoviruses at various m.o.i.'s, and incubated overnight. GFP activity was measured after 72 hrs, and % of GFP-positive cells was determined. Data are summarized in Tables XVIIa and b; the graphic representation is in FIGS. 18a and b.

Example 16

Figure 19:
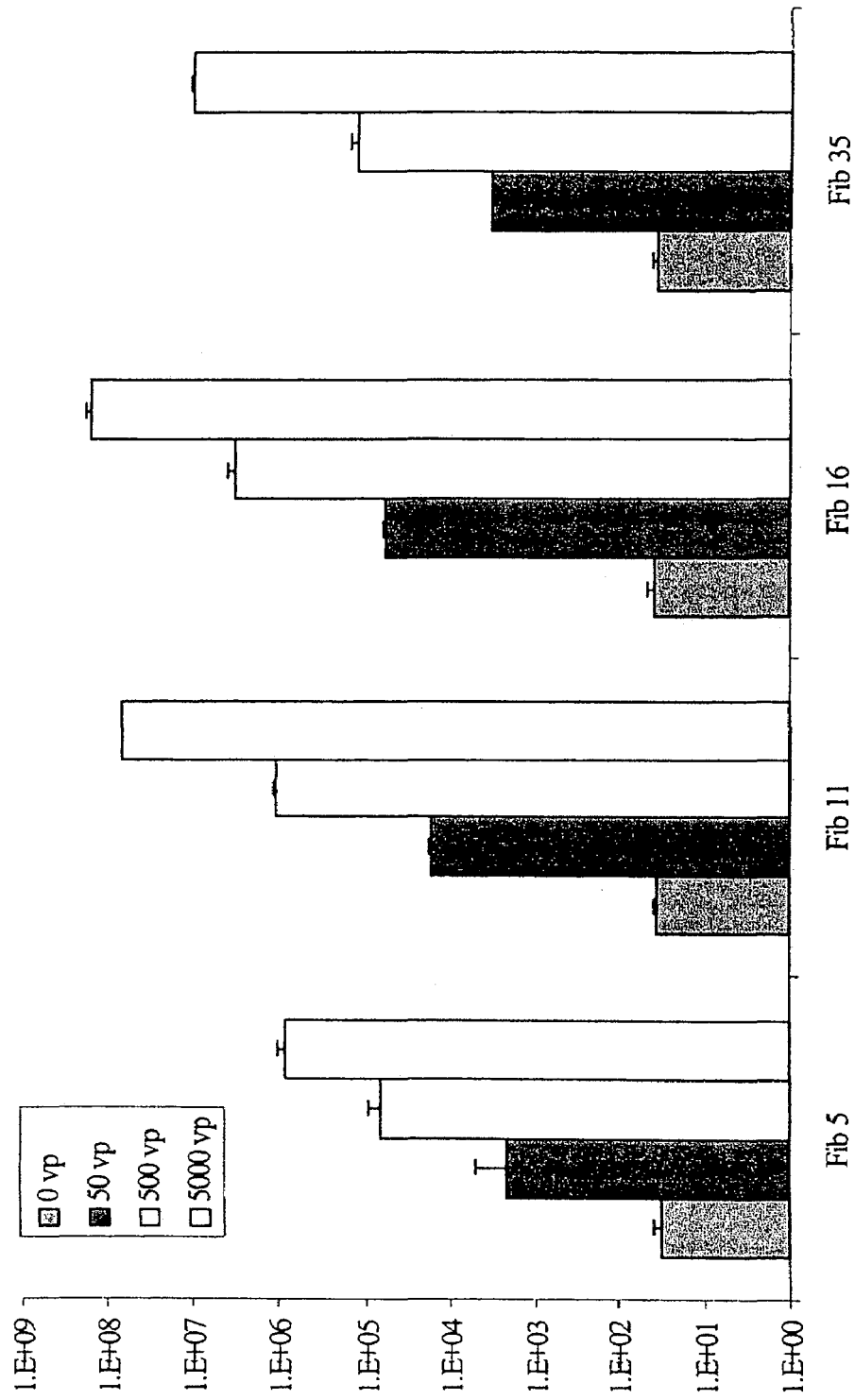
FIG. 19 is a graph depicting the comparison of three B-type fiber-modified adenovirus for infectivity on RA synoviocytes.

Comparison of Infection of Three B-Type Fiber-Modified Viruses on RA Synoviocytes Three chimeric adenoviruses, each carrying a B-type fiber were tested for its infectivity on RA synoviocytes, in comparison to Ad5. The following chimeric adenoviruses were produced: Ad5.fib11, 16 and 35, each carrying a luciferase transgene. In each experiment, a total of 15,000 RA synoviocytes was seeded per well in 12-well microtiter dishes. Cells were infected the chimeric adenoviruses at various m.o.i.'s, and incubated overnight. Luciferase activity was measured after 72 hrs. Data are summarized in Table XVIII and FIG. 19.

Example 17

Figure 20:
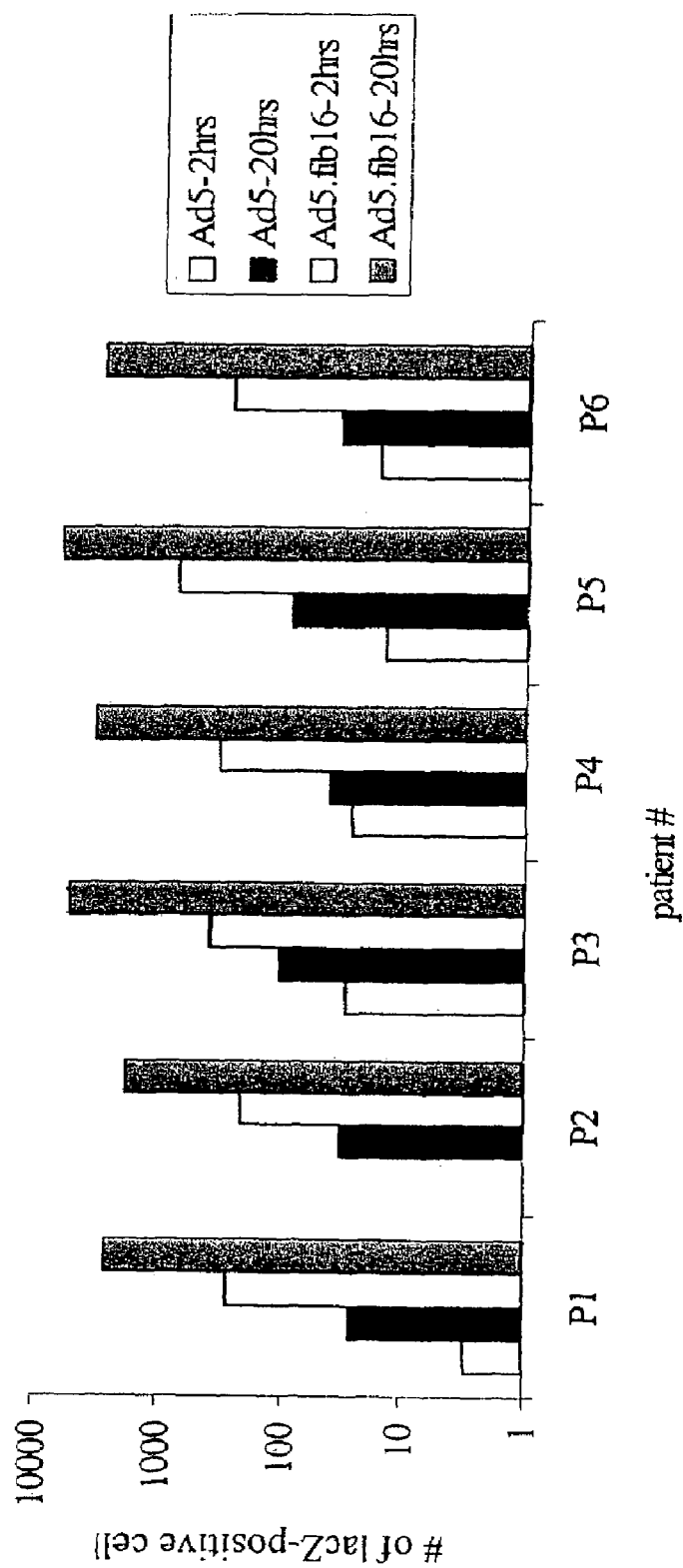
FIG. 20 is a graph depicting the comparison of infectivity Ad5.lacZ vs. Ad5.fib16.lac6 in RA synoviocytes fro six patients.

Comparison of Infection of RA Synoviocytes With Ad5 and Ad5.fib16 in Different Patients Synoviocyte cells were obtained from 6 different patients suffering from rheumatoid arthritis. Synoviocytes were infected with Ad5.lacZ or Ad5.fib16.lacZ during 2 or 20 hours, and stained for lacZ expression after 48 hours. Numbers of blue cells were counted under the microscope. Data are summarized in Table XIX, plotted in FIG. 20.

Tables

TABLE I

Oligonucleotides and degenerate oligonucleotides used for the amplification of DNA encoding fiber protein derived from alternative adenovirus serotypes. (Bold letters represent NdeI restriction site (A–E), NsiI restriction site (1–7, 8), or PacI restriction site (7).

| Serotype | Tail oligonucleotide | Knob oligonucleotide |
|---|---|---|
| 4 | A | 1 |
| 8 | B | 2 |
| 9 | B | 2 |
| 12 | E | 3 |
| 16 | C | 4 |
| 19p | B | 2 |
| 28 | B | 2 |
| 32 | B | 2 |
| 36 | B | 2 |
| 37 | B | 2 |
| 40-1 | D | 5 |
| 40-2 | D | 6 |
| 41-s | D | 5 |
| 41-1 | D | 7 |

TABLE I-continued

| | | |
|---|---|---|
| 49 | B | 2 |
| 50 | B | 2 |
| 51 | C | 8 |

```
A: 5'- CCC GTG TAT CCA TAT GAT GCA GAC AAC GAC CGA CC- 3'        (SEQ ID NO:19)
B: 5'- CCC GTC TAC CCA TAT GGC TAC GCG CGG- 3'                   (SEQ ID NO:20)
C: 5'- CCK GTS TAC CCA TAT GAA GAT GAA AGC- 3'                   (SEQ ID NO:21)
D: 5'- CCC GTC TAC CCA TAT GAC ACC TYC TCA ACT C- 3'             (SEQ ID NO:22)
E: 5'- CCC GTT TAC CCA TAT GAC CCA TTT GAC ACA TCA GAC- 3'       (SEQ ID NO:23)
1: 5"- CCG ATG CAT TTA TTG TTG GGC TAT ATA GGA - 3'              (SEQ ID NO:24)
2: 5'- CCG ATG CAT TYA TTC TTG GGC RAT ATA GGA - 3'              (SEQ ID NO:25)
3: 5'- CCG ATG CAT TTA TTC TTG GGR AAT GTA WGA AAA GGA - 3'      (SEQ ID NO:26)
4: 5'- CCG ATG CAT TCA GTC ATC TTC TCT GAT ATA - 3'              (SEQ ID NO:27)
5: 5'- CCG ATG CAT TTA TTG TTC AGT TAT GTA GCA - 3'              (SEQ ID NO:28)
6: 5'- GCC ATG CAT TTA TTG TTC TGT TAC ATA AGA - 3'              (SEQ ID NO:29)
7: 5' - CCG TTA ATT AAG CCC TTA TTG TTC TGT TAC ATA AGA A - 3'   (SEQ ID NO:30)
8: 5'- CCG ATG CAT TCA GTC ATC YTC TWT AAT ATA - 3'              (SEQ ID NO:31)
```

TABLE II

Biodistribution of chimaeric adenovirus upon intravenous tail vein injection. Values represent luciferase activity expressed as relative light units/μg protein. Values in the brain are considered background.

| Organ | Ad5.Clip.Luc | Ad5.Luc-fib16 |
|---|---|---|
| Liver | 740045 | 8844 |
| Spleen | 105432 | 3442 |
| Lung | 428 | 334 |
| Kidney | 254 | 190 |
| Heart | 474 | 276 |
| Brain | 291 | 294 |

TABLE III

Expression of CAR and integrins on the cell surface of synoviocytes. Values represent percentages of cells that express CAR or either one of the integrins at levels above background. Synoviocytes incubated only with the secondary, rat-anti-mouse IgG1-PE labeled antibody served as a background control.

| Cells | $\alpha_v\beta3$ | $\alpha_v\beta5$ | CAR |
|---|---|---|---|
| Synoviocytes | 27.2% | 35.4% | 0% |
| PER.C6 | 7.8% | 16.8% | 99.6% |

TABLE IV

Determination of transgene expression (luciferase activity) per μg of total cellular protein after infection of A549 cells

| MOI (VP/Cell) | Control Ad5 | Fiber 16 |
|---|---|---|
| 0 | 0 | 0 |
| 5 | 1025 | 661 |
| 10 | 1982 | 1704 |
| 25 | 4840 | 3274 |
| 100 | 21875 | 13432 |
| 500 | 203834 | 93163 |

TABLE V

Determination of transgene expression (luciferase activity) per μg of total cellular protein after infection of PER.C6 cells

| Virus particles/ml | Control Ad5 | Ad5fiber16 |
|---|---|---|
| 10 | 24800 | 9300 |

TABLE VI

Summary of rhesus monkeys experiments

| monkey name | date of birth | sex | weight (kg) | virus | Dose (pfu's) | joint | sacrifice (day) | blood sampling (day) | excreta (day) |
|---|---|---|---|---|---|---|---|---|---|
| 1: BB 112 | 01 Jan. 1993 | M | 3.000 | IG.Ad.CMV.1 acZ | $5 \times 10^9$ | knee L | 2 | 0 | — |
| | | | | IG.Ad.CMV.1 uc | $1 \times 10^9$ | knee L | | | |
| 2: | 25 Sep. | F | 3.900 | IG.Ad.CMV.1 | $5 \times 10^9$ | knee L | 2 | 0 | — |

TABLE VI-continued

Summary of rhesus monkeys experiments

| monkey name | date of birth | sex | weight (kg) | virus | Dose (pfu's) | joint | sacrifice (day) | blood sampling (day) | excreta (day) |
|---|---|---|---|---|---|---|---|---|---|
| 9163 | 1991 | | | acZ IG.Ad.CMV.1 uc | $1 \times 10^9$ | knee L | | | |
| 3: 9179 | 19 Dec. 1991 | F | 3.500 | IG.Ad.CMV.1 acZ IG.Ad.mlp.1 acZ IG.Ad.CMV.1 uc | $5 \times 10^8$ $1.5 \times 10^9$ $1 \times 10^8$ | pip 4 R F pip 2 LH pip 2 LH, 4 RF | 2 | 0 | — |
| 4: Q 079 | 01 Dec. 1993 | F | 2.600 | IG.Ad.CMV.1 acZ IG.Ad.CMV.1 uc | $3.2 \times 10^{5-9}$ $2.2 \times 10^{4-8}$ | pip 2, 3, 4, 5 FF + HH and knee L + R pip 2, 3, 4, 5 FF + HH and knee L + R ** | 3 | −303 | — |
| 5: 94074 | 05 Sep. 1994 | F | 2.900 | IG.Ad.mlp.1 acZ IG.Ad.mlp.1 uc | $1 \times 10^{6-10}$ $1 \times 10^{10}$ | pip 2, 3, 4, 5 LH + RH and knee L knee R | 3 | −7, 0, 1, 2, 3 | −7, 0, 1, 2, 3 |
| 6: Z 02 | 01 Jan. 1992 | F | 4.900 | IG.Ad.CMV.1 uc IG.Ad.mlp-l.TK | $1 \times 10^8$ $1 \times 10^{11}$ | knee L + R knee L + R | 15 | 0, 3, 7, 15 | 0, 15 |
| 7: 94044 | | M | 2.600 | IG.Ad.mlp-l.TK | $5.8 \times 10^{10}$ | knee L | 18 | −7, 0, 2, 7, 10, 14, 18 | −7, 0,1,2, 3,4,5 |
| 8: 94048 | | M | 2.850 | IG.Ad.mlp-l.TK | $5.8 \times 10^{10}$ | knee L | 18 | −7, 0, 2, 7, 10, 14, 18 | −7, 0, 1, 2, 3, 4, 5 |

M = male,
F = female;
LH = left hand,
RF = right foot,
HH = both hands,
FF = both feet;
** = in all joint on left side 10% triamcinolonehexacetonide 20 mg/ml is added.

TABLE VII

Survival of synoviocytes after infection with modified Ad. Negative controls were carried out in duplos in 3 of 5 experiments.

| patient | number of cells t = 0 (×1000) | experiment | cell count on day | neg. control (cells × 1000) | CMV MOI 100 (cells × 1000) | mlp MOI 100 (cells × 1000) |
|---|---|---|---|---|---|---|
| RA-1-a | 200 | IG.Ad.lacZ | 2 | 76 | 187 | 201 |
| RA-1-b | 100 | IG.Ad.lacZ | 2 | 90–160 | 118 | 194 |
| RA-2 | 100 | IG.Ad.lacZ | 2 | 76 | 56 | 56 |
| RA-3-a | 100 | IG.Ad.luc | 3 | 42–38 | 49 | 38 |
| RA-3-b | 100 | IG.Ad.luc | 3 | 35–31 | 31 | 52 |

TABLE VIII

Lac Z data monkey 4.

| joint: | left hand ** | left foot ** | right hand | right foot | concentrations injected Ad.lacZ |
|---|---|---|---|---|---|
| pip 2 | − | − | − | − | $3.2 \times 10^5$ |
| pip 3 | − | + | − | − | $3.2 \times 10^6$ |
| pip 4 | − | + | ++ | − | $3.2 \times 10^7$ |
| pip 5 | ++ | +++ | +++ | ++ | $3.2 \times 10^8$ |
| knee | left: ++++ | | right: ++++ | | $3.2 \times 10^9$ |

Virus concentrations in plague forming units.
** = 10% triamcinolonehexacetonide (20 mg/ml) in injection.

−: no blue cells
+: 1–10 blue cells in synovial lining
++: 1–5% blue cells in synovial lining
+++: 5–50% blue cells in synovial lining
++++: >50% blue cells in synovial lining

TABLE IX

Luciferase counts in organs as a measure of virus spread after intra-articular injection of Ad.CMV.luc.

| monkey: | 1–4 mean (range) | 5 mean (range) | 6 | control |
|---|---|---|---|---|
| conc. injected Ad. | $2,2–10 \cdot 10^8$ IG.Ad.CMV.luc | $10^{10}$ IG.Ad.mlp.luc | $10^8$ IG.Ad.CMV.luc | — |
| termination day: | 2–3 | 3 | | 15 |
| Ad.luc-injected joints | 553,491 (47,773–1,000,460) | 368 | 69 (66–71) | — |
| non Ad-injected joints | 390 (63–2515) | 93 | — | — |
| heart | 86 (82–114) | 147 (105–223) | 60 | 142 |
| liver | 99 (81–128) | 115 | 49 | 126 |
| spleen | 99 (65–165) | 98 | 57 | 101 |
| testis | 82 | female | 55 | female |
| cervix | 227 (90–457) | 101 | male | 115 |
| prostate | 120 | female | — | female |
| ovary | 90 (76–111) | 107 | male | 92 |
| bone marrow | 60 (54–69) | 110 | — | — |
| blood t = 0 | 68 (62–71) | 165 (86–349) | — | — |
| blood section | 56 (50–62) | 91 (86–96) | — | — |
| draining lymph node | | 96 | | |
| non-draining lymph nodes | | 112 (105–118) | | |
| kidney | | 110 | | |
| lung | | 102 | | |
| esophagus | | 78 | | |
| bladder | | 100 | | |

TABLE X

Lactate Dehydrogenate levels in U/l.

| | | t (days) | | | | | | | | |
|---|---|---|---|---|---|---|---|---|---|---|
| first: | | 0 | 2 | 3 | 4 | 5 | 7 | 10 | 14 | 15 | 18 |
| monkey 4 | t-4: 358 | 216 | | 763 | | | | | | | |
| monkey 6 | t-30: 1050 | 6340 | 6835 | | 5939 | | | | | | |
| monkey 5 | | 760 | | 627 | | | 1182 | | | 686 | |
| monkey 7 | t-38: 999 | 5185 | 4387 | 4679 | | 6547 | 4740 | 5586 | 6128 | | 5226 |
| monkey 8 | t-38: 958 | 5994 | 4881 | 10140 | 8000 | 8230 | 2952 | 7259 | 3800 | | 4053 |

LDH levels in monkey 4 (CMV.lacZ/CMV.luc), 5 (mlp.lacZ/mlp.luc), 6 (mlp.TK), 7 and 8 (mlp.TK + GCV). LDH-levels in monkey 6, 7 and 8 are determined with another test than monkey 4 and 5.

TABLE XI

Percentage of lacZ-expressing synoviocytes 2 days after infection with IG.Ad.CMV.lacZ or IG.Ad.mlp.lacZ

| | MOI | | | | |
|---|---|---|---|---|---|
| | 0 | 0.1 | 1 | 10 | 100 |
| IG.Ad.CMV. lacZ (SD) | 0 | <1% (0%) | 2.5% (1.5%) | 12.9% (6.3%) | 53.4% (14.9%) |
| IG.ad.MLP. lacZ (SD) | 0 | 0 | 0 | <1% (0%) | <1% (0%) |

TABLE XII

Light counts as a measure of luciferase-expression in synoviocytes 3 days after infection with IG.Ad.CMV.luc or IG.Ad.mlp.luc

| | MOI | | | | |
|---|---|---|---|---|---|
| | 0 | 0.1 | 1 | 10 | 100 |
| IG.Ad.MLP.1 uc (SD) | 0 | 53 (5) | $9.6 \cdot 10^2$ $(2.0 \cdot 10^2)$ | $7.5 \cdot 10^3$ $(2.6 \cdot 10^3)$ | $1.7 \cdot 10^3$ $(2.3 \cdot 10^4)$ |
| IG.Ad.CMV.1 uc (SD) | 0 | $2.9 \cdot 10^2$ (18) | $2.1 \cdot 10^3$ $(6.0 \cdot 10^2)$ | $7.4 \cdot 10^4$ $(4.4 \cdot 10^4)$ | $1.1 \cdot 10^6$ $(9.5 \cdot 10^4)$ |

TABLE XIII

Comparison of RA synoviocyte infection of Ad5.luc and Ad5.fib16.luc
(average luciferase activity (n = 3))

| Virus | 0 vp/cell | 50 vp/cell | 500 vp/cell | 5000 vp/cell |
|---|---|---|---|---|
| Ad5.luc | 63 | 243 | 559 | 189519 |
| Ad5.fib16.luc | 62 | 715484 | 7.86E+0 | 1.02E+09 |

TABLE XIV

% lacZ positive cells with Ad5.lacZ and Ad5.fib16.lacZ in RA synoviocytes

| | 50 vp/cell | 500 vp/cell | 5000 vp/cell |
|---|---|---|---|
| Ad5.lacZ | 2.17 | 7.33 | 35.50 |
| Ad5.Fib16.lacZ (120 A) | 28.00 | 67.50 | 100.00 |
| Ad5.Fib16.lacZ (130 B) | 33.83 | 74.54 | 100.00 |

TABLE XVa comparison of infection efficiency Ad5.fib5 GFP and Ad5.fib16.GFP in RA Synoviocytes
(% of GFP-positive cells)

| | Fib5 (103) | Fib5 (130D) | Fib16 (103) | Fib16 (IC) |
|---|---|---|---|---|
| 50 vp/cell | 4.81 | 5.66 | 35.05 | 52.07 |
| 500 vp/cell | 26.75 | 24.66 | 85.87 | 90.21 |
| 5000 vp/cell | 75.56 | 72.53 | 100.00 | 100.00 |

TABLE XVb

| | Fib5 (103) | Fib5 (130D) | Fib16 (103) | Fib16 (IC) |
|---|---|---|---|---|
| 50 vp/cell | 1.02 | 1.04 | 1.61 | 11.92 |
| 500 vp/cell | 1.36 | 1.31 | 586.34 | 1540.93 |
| 5000 vp/cell | 217.85 | 184.96 | 8058.42 | 7773.65 |

TABLE XVI infectivity of panel of chimeric adenoviruses on RA synoviocytes (Luciferase activity/well)

| Virus | 0 vp/cell | 50 vp/cell | 500 vp/cell | 5000 vp/cell |
|---|---|---|---|---|
| Ad5.Fib 5 | 31 | 6348 | 32612 | 497488 |
| Ad5.Fib 11 | 26 | 10775 | 524221 | 33831033 |
| Ad5.Fib 16 | 32 | 17937 | 821418 | 38760900 |
| Ad5.Fib 24 | 29 | 220 | 1237 | 52601 |
| Ad5.Fib 28 | 24 | 106 | 1798 | 15199 |
| Ad5.Fib 33 | 31 | 163 | 1865 | 92049 |
| Ad5.Fib 35 | 27 | 2319 | 103286 | 7812200 |
| Ad5.Fib 45 | 29 | 95 | 1304 | 28373 |
| Ad5.Fib 47 | 29 | 145 | 1901 | 54053 |

TABLE XVIIa

% of infected cells with three B-type fiber-modified viruses on RA synoviocytes

| | Ad5 | Ad5.fib16 | Ad5.fib35 | Ad5.fib51 |
|---|---|---|---|---|
| 50 vp/cell | 7.32 | 52.31 | 69.17 | 57.84 |
| 500 vp/cell | 38.83 | 92.60 | 94.49 | 93.28 |
| 5000 vp/cell | 87.91 | 100.00 | 100.00 | 100.00 |

TABLE XVIIb

GFP production with three B-type fiber-modified viruses on RA synoviocytes

| | Ad5 | Ad5.fib16 | Ad5.fib35 | Ad5.fib51 |
|---|---|---|---|---|
| 50 vp/cell | 1.76 | 42.29 | 262.84 | 78.59 |
| 500 vp/cell | 5.77 | 3126.39 | 8012.87 | 3929.21 |
| 5000 vp/cell | 1386.49 | 9646.62 | 9646.62 | 9646.62 |

TABLE XVIII comparison of three B-type fiber modified adenoviruses for infectivity on RA synoviocytes (luc-production)

| virus | 0 vp/cell | 50 vp/cell | 500 vp/cell | 5000 vp/cell |
|---|---|---|---|---|
| Ad5 | 31 | 2073 | 67365 | 848476 |
| Ad5.Fib 11 | 35 | 16926 | 1094044 | 69718467 |
| Ad5.Fib 16 | 38 | 58366 | 3371600 | 164933133 |
| Ad5.Fib 35 | 35 | 3321 | 129236 | 10440833 |

TABLE XIX comparison of Ad5.lacZ vs. Ad5.fib16.lacZ in 6 patients
(# of lacZ-positive cells)

| | P1 | P2 | P3 | P4 | P5 | P6 |
|---|---|---|---|---|---|---|
| Ad5-2 hrs | 3 | 1 | 28 | 26 | 14 | 16 |
| Ad5-20 hrs | 26 | 32 | 101 | 39 | 86 | 34 |
| Ad5.fib16-2 hrs | 267 | 209 | 365 | 325 | 713 | 259 |
| Ad5.fib16-20 hrs | 2565 | 1762 | 5124 | 3258 | 6158 | 2923 |

REFERENCES

Amberg N., Mei Y. and Wadell G., 1997. Fiber genes of adenoviruses with tropism for the eye and the genital tract. Virology 227: 239–244.

Arnett F C, Edworthy S M, Bloch D A, et al. (1988). The American Rheumatism Association 1987. Revised criteria for the classification of rheumatoid arthritis. Arthritis and rheumatism; 31:315–323.

Bakker N. P. M., (1992). Collagen-induced arthritis in the Rhesus monkey. Relations between aspects of autoimmunity and disease development. Thesis, 27-10-92 Catholic University Nijmegen.

Bergelson, J. M., Cunningham, J. A., Droguett, G., Kurt-Jones, E. A., Krithivas, A., Hong, J. S., Horwitz, M. S., Crowell, R. L. and Finberg, R. W. (1997) Isolation of a common receptor for coxsackie B virus and adenoviruses 2 and 5. Science 275: 1320–1323.

A. Bout, J-L. Imler, H. Schultz, M Perricaudet, C. Zurcher, P. Herbrink, D. Valerio and A. Pavirani (1994). in vivo adenovirus-mediated transfer of human CFTR-cDNA to rhesus monkey airway epithelium: efficacy, toxicity and safety. Gene therapy 1,1–10.

A. Bout, D. Valerio, B. J. Scholte. (1993) in vivo transfer and expression of the lacZ gene in the mouse lung. Exp. Lung Res. 19, 193–202.

Bout A. (1997) Gene therapy, p. 167–182. In: D. J. A. Crommelin and R. D. Sindelar (ed.), Pharmaceutical Biotechnology, Harwood Academic Publishers.

Bout, A. (1996) Prospects for human gene therapy. Eur. J. Drug Met. and Pharma. 2, 175–179.

Blaese, M., Blankenstein, T., Brenner, M., Cohen-Hagenauer, O., Gansbacher, B., Russel, S., Sorrentino, B. and Velu, T. (1995) Cancer Gene Ther. 2: 291–297.

Brody, S. L. and Crystal, R. G. (1994) Adenovirus mediated in vivo gene transfer. Ann. N.Y. Acad. Sci. 716:90–101.

Carter, A. J., Laird, J. R., Farb, A., Kufs, W., Wortham, D. C. and Virmani, R. (1994) Morphologic characteristics of lesion formation and time course of smooth muscle cell proliferation in a porcine proliferative restenosis model. J. Am. Coll. Cardiol. 24: 1398–1405.

Chroboczek J., Ruigrok R. W. H., and Cusack S., 1995. Adenovirus fiber, p. 163–200. In: W. Doerfler and P. Bohm (ed.), The molecular repertoire of adenoviruses, I. Springer-Verlag, Berlin.

Cruz-Esteban C., W. S. Wilke (1995). Non-surgical synovectomy
BailliPre's Clinical Rheumatology vol9, 787–800

Defer C., Belin M., Caillet-Boudin M. and Boulanger P., 1990. Human adenovirus-host cell interactions; comparative study with members of subgroup B and C. Journal of Virology 64 (8): 3661–3673.

Edwards J. C. W., 1995. Synovial intimal fibroblasts. Ann. Rheum. Dis. 54, 395–397

Evans, C. H. et al. (1996) Clinical protocol to assess the safety, feasibility and efficacy of transferring a potentially anti-arthritic cytokine gene to human joints with rheumatoid arthritis. Hum. Gen. Ther. 7:1261–1280.

Fallaux, F. J, Bout, A, van der Velde, I et al. New helper cells and matched E1-deleted adenovirus vectors prevent generation of replication competent adenoviruses. Human Gene Therapy, 9(1998), p1909–1917.

Firestein, G. S. (1996) Invasive fibroblast-like synoviocytes in rheumatoid arthritis. Passive responders or transformed aggressors? Arthritis Rheum. 39: 1781–1790.

Francki, R. I. B., Fauquet, C. M., Knudson, D. L. and Brown, F. (1991) Classification and nomenclature of viruses. Fifth report of the international Committee on taxonomy of viruses. Arch. Virol. Suppl. 2: 140–144.

Gall J., Kass-Eisler A., Leinwand L. and Falck-Pedersen E. (1996) Adenovirus type 5 and 7 capsid chimera: fiber replacement alters receptor tropism without affecting primary immune neutralization epitopes. Journal of Virology 70 (4): 2116–2123.

Greber, U. F., Willets, M., Webster, P., and Helenius, A. (1993). Stepwise dismantling of adenovirus 2 during entry into cells. Cell 75: 477–486.

Hynes, R. O. (1992) Integrins: versatility, modulation and signaling in cell adhesion. Cell 69: 11–25.

Herz, J. and Gerard, R. D. (1993) Adenovirus-mediated transfer of low density lipoprotein receptor gene acutely accelerates cholesterol clearance in normal mice. Proc. Natl. Acad. Sci. U.S.A. 96: 2812–2816.

Hierholzer, J. C. (1992) Adenovirus in the immunocompromised host. Clin. Microbiol Rev. 5, 262–274.

Hierholzer, J. C., Wigand, R., Anderson, L. J., Adrian, T., and Gold, J. W. M. (1988) Adenoviruses from patients with AIDS: a plethora of serotypes and a description of five new serotypes of subgenus D (types 43–47). J. Infect. Dis. 158, 804–813.

Hong, S. S., Karayan, L., Toumier, J., Curiel, D. T. and Boulanger, P. A. (1997) Adenovirus type 5 fiber knob binds to MHC class I a2 domain at the surface of human epithelial and B lymphoblastoid cells. EMBO J. 16: 2294–2306.

Hsu, K. H., Lonberg-Holm, K., Alstein, B. and Crowell, R. L. (1988) A monoclonal antibody specific for the cellular receptor for the subgroup B coxsackie viruses. J. Virol 62(5): 1647–1652.

Huard, J., Lochmuller, H., Acsadi, G., Jani, A., Massie, B. and Karpati, G. (1995) The route of administration is a major determinant of the transduction efficiency of rat tissues by adenoviral recombinants. Gene Ther. 2: 107–115.

Imler J.-L., Bout A., Dreyer D. Trans-complementation of E1-deleted adenovirus: a new vector to reduce the possibility of co-dissemination of wild-type and recombinant adenoviruses. Human Gene Therapy 6, 711–721

Ishibashi, M. and Yasue, H. (1984) The adenoviruses, H. S. Ginsberg, ed., Plenum Press, London, New York. Chapter 12, 497–561.

Kass-Eisler, A., Falck-Pederson, E., Elfenbein, D. H., Alvira, M., Buttrick, P. M. and Leinwand, L. A. (1994) The impact of developmental stage, route of administration and the immune system on adenovirus-mediated gene transfer. Gene Ther. 1: 395–402.

Khoo, S. H., Bailey, A. S., De Jong, J. C., and Mandal, B. K. (1995). Adenovirus infections in human immunodeficiency virus-positive patients: Clinical features and molecular epidemiology. J. Infect. Dis 172, 629–637

Kidd, A. H., Chroboczek, J., Cusack, S., and Ruigrok, R. W. (1993) Adenovirus type 40 virions contain two distinct fibers. Virology 192, 73–84.

Krasnykh V. N., Mikheeva G. V., Douglas J. T. and Curiel D. T. (1996) Generation of recombinant adenovirus vectors with modified fibers for altering viral tropism. J. Virol. 70(10): 6839–6846.

Krasnykh V. N., Dmitriev I., Mikheeva G., Miller C. R., Belousova N. and Curiel D. T. (1998) Characterization of an adenovirus vector containing a heterologous peptide epitope in the HI loop of the fiber knob. J. Virol. 72(3): 1844–1852.

Law, L., Chillon, M., Bosch, A., Armentano, D., Welsh, M. J. and Davidson, B. L. (1998) Infection of primary CNS cells by different adenoviral serotypes: Searching for a more efficient vector. Abstract 1$^{st}$ Annual Meeting American Society of Gene Therapy, Seattle, Wash.

Leppard, K. N. (1997) E4 gene function in adenovirus, adenovirus vector and adeno-associated virus infections. J. Gen. Virol. 78: 2131–2138.

Lloyd Jones, D. M. and Bloch, K. D. (1996) The vascular biology of nitric oxide and its role in atherogenesis. Annu. Rev. Med. 47: 365–375.

Morgan, C., Rozenkrantz, H. S., and Mednis, B. (1969) Structure and development of viruses as observed in the electron microscope. X. Entry and uncoating of adenovirus. J. Virol 4, 777–796.

H. Nakamura, S. Yoshino, N. Ishiuchi, J. Fujimori, T. Kanai, Y. Nishimura. (1997). Outcome of radical synovectomy as a novel surgical treatment for refractory RA: implication of HLA-DRB1*0405 in post-operative results. Clinical and experimental rheumatology; 15; 53–57.

Nita, I. and S. C. GHIVIZZANI. (1996) Direct gene delivery to synovium. An evaluation of potential vectors in vivo and in vitro. Arthritis Rheum. 39:820–828.

Qu, Z., C. H. Garcia, L. M. O'Rourke, S. R. Planck, M. Kohli and J. T. ROSENBAUM. (1994) Local proliferation of fibroblast-like synoviocytes contributes to synovial hyperplasia. Arthr. Rheum. 37:212–220.

Roelvink, P. W., Kovesdi, I. and Wickham, T. J. (1996) Comparative analysis of adenovirus fiber-cell interaction: Adenovirus type 2 (Ad2) and Ad9 utilize the same cellular fiber receptor but use different binding strategies for attachment. J. Virol. 70: 7614–7621.

Roelvink, P. W., Lizonova, A., Lee, J. G. M., Li, Y., Bergelson, J. M., Finberg, R. W., Brough, D. E., Kovesdi, I. and Wickham, T. J. (1998) The coxsackie-adenovirus receptor protein can function as a cellular attachment protein for adenovirus serotypes from subgroups A, C, D, E, and F. J. Virol. 72: 7909–7915.

B. J. Roessler, E. D. Allen, J. M. Wilson, J. W. Hartman, B. L. Davidson (1993). Adenoviral mediated gene transfer to rabbit synovium in vivo. J. Clin. Invest 92;1085–1092.

Rogers, B. E., Douglas J. T., Ahlem, C., Buchsbaum, D. J., Frincke, J. and Curiel, D. T. (1997) Use of a novel cross-linking method to modify adenovirus tropism. Gene Ther. 4: 1387–1392.

Schulick, A. H., Vassalli, G., Dunn, P. F., Dong, G., Rade, J. J., Zamarron, C. and Dichek, D. A. (1997). Established immunity precludes adenovirus-mediated gene transfer in rat carotid arteries.

Schnurr, D and Dondero, M. E. (1993) Two new candidate adenovirus serotypes. Intervirol. 36, 79–83.

Schwartz, R. S., Edwards, W. D., Huber, K. C., Antoniudes, L. C. Bailey, K. R., Camrud, A. R., Jorgenson, M. A. and Holmes, D. R. Jr. (1993) Coronary restenosis: Prospects for solution and new perspectives from a porcine model. Mayo Clin. Proc. 68: 54–62.

Shi, Y., Pieniek, M., Fard, A., O'Brien, J., Mannion, J. D. and Zalewski, A. (1996) Adventitial remodeling after coronary arterial injury. Circulation 93: 340–348.

Shabram, P. W., Giroux, D. D., Goudreau, A. M., Gregory, R. J., Horn, M. T., Huyghe, B. G., Liu, X., Nunnally, M. H., Sugarman, B. J. and Sutjipto, S. (1997) Analytical anion-exchange HPLC of recombinant type-5 adenoviral particles. Hum. Gene Ther. 8(4): 453–465.

Signas, G., Akusjarvi, G., and Petterson, U. (1985). Adenovirus 3 fiber polypeptide gene: Complications for the structure of the fiber protein. J. Virol. 53, 672–678.

Stevenson S. C., Rollence M., White B., Weaver L. and McClelland A., (1995) Human adenovirus serotypes 3 and 5 bind to two different cellular receptors via the fiber head domain. J. Virol 69(5): 2850–2857.

Stevenson S. C., Rollence M., Marshall-Neff J. and McClelland A. (1997) Selective targeting of human cells by a chimaeric adenovirus vector containing a modified fiber protein. J. Virology 71(6): 4782–4790.

Stouten, P. W. F., Sander, C., Ruigrok, R. W. H., and Cusack, S. (1992) New triple helical model for the shaft of the adenovirus fiber. J. Mol. Biol. 226, 1073–1084.

Svensson, V. and Persson, R. (1984). Entry of adenovirus 2 into Hela cells. J. Virol. 51, 687–694.

S. J. Sawchuk (1996). Anti-T cell receptor monoclonal antibody prolongs transgene expression following adenovirus-mediated in vivo gene transfer to mouse synovium. Human gene therapy 7; 499–506.

Thompson, M., G. Douglas and E. P. DAVISON. (1973) Evaluation of synovectomy in rheumatoid arthritis. Proc. Roy. Soc. Med. 66:197–199.

van der Vliet, P. C. (1995) Adenovirus DNA replication In: W. Doerfler and P. Böhm (eds.), The molecular repertoire of adenoviruses II. Springer-Verlag, Berlin.

Varga, M. J., Weibull, C., and Everitt, E. (1991). Infectious entry pathway of adenovirus type 2. J. Virol 65, 6061–6070.

Varenne, O., Pislaru, S., Gillijns, H., Van Pelt, N., Gerard, R. D., Zoldhelyi, P., Van de Werf, F., Collen, D. and Janssens, S. P. (1998) Local adenovirus-mediated transfer of human endothelial nitric oxide synthetase reduces luminal narrowing after coronary angioplasty in pigs. Circulation 98: 919–926.

Vincent, A. J. P. E., R. Vogels and G. van Someren. (1996) Herpes simplex virus thymidine kinase gene therapy for malignant brain tumors. Hum. Gen. Ther. 7:197–205.

Wickham T. J., Carrion M. E. and Kovesdi I., 1995. Targeting of adenovirus penton base to new receptors through replacement of its RGD motif with other receptor-specific peptide motifs. Gene Therapy 2: 750–756.

Wickham et al., Targeted adenovirus gene transfer to endothelial and smooth muscle cells by using bispecific antibodies. J. Virol. 70 (10), 6831–6838 (1966).

Wickham, T. J., Mathias, P., Cherish, D. A., and Nemerow, G. R. (1993) Integrins $a_vb_3$ and $a_vb_5$ promote adenovirus internalization but not virus attachment. Cell 73, 309–319.

Wold et al., E3 transcription unit of adenovirus. In: W. Doerfler and P. Böhm (eds.), The molecular repertoire of adenoviruses I. Springer-Verlag, Berlin, DE (1995).

Zabner et al., Type 17 fiber enhances gene transfer Abstract $1^{st}$ Annual Meeting American Society of Gene Therapy, Seattle, Wash. (1998).

Zvaifler, N. J. and G. S. FIRESTEIN. (1994) Pannus and pannocytes, alternative models of joint destruction in RA. Arthritis Rheum. 37:783–789.

What is claimed is:

1. A method of delivering a nucleic acid of interest to a fibroblast-like or a macrophage-like cell in vitro, said fibroblast-like or a macrophage-like cell being isolated from a synovial cavity, the method comprising:

providing a recombinant adenovirus of subgroup C comprising the nucleic acid of interest and having a tissue tropism for fibroblast-like or macrophage-like cells, wherein the capsid of said recombinant adenovirus comprises at least one protein of an adenovirus serotype of subgroup C and at least the tissue tropism determining domain of a fiber protein of a second adenovirus serotype, said second adenovirus serotype being selected from the group consisting of adenovirus serotype 11, 16, 35, and 51; and infecting a fibroblast-like or a macrophage-like cell, said fibroblast-like or a macrophage-like cell being isolated from a synovial cavity, with said recombinant adenovirus.

2. The method according to claim 1, wherein said adenovirus of subgroup C is of adenovirus serotype 5.

3. The method according to claim 2, wherein said recombinant adenovirus comprises an adenovirus serotype 5 genome, wherein the sequence encoding the tissue tropism determining domain of the fiber protein of serotype 5 is replaced by a sequence encoding the tissue tropism determining domain of the fiber protein of said second adenovirus serotype.

4. The method according to claim 3, wherein said recombinant adenovirus comprises at least one deletion in the E1 or the E3 region, where the nucleic acid of interest is inserted or can be inserted.

5. The method according to claim 1, wherein said nucleic acid of interest encodes a gene product selected from the group consisting of: the Herpes Simplex Virus thymidine kinase, an apolipoprotein, a nitric oxide synthase, interleukin-3, interleukin-1RA, interleukin-1alpha, an (anti)angiogenesis protein, an anti-proliferation protein, a Vascular Endothelial Growth Factor (VEGF), a basic Fibroblast Growth Factor (bFGF), a hypoxia inducible factor 1alpha (HIF-1alpha), PAI-1, a smooth muscle cell anti-migration protein, erythropoietin (EPO), CD40, FasL, interleukin-12, interleukin-10, interleukin-4, interleukin-1 13, an excreted single chain antibody to CD4, CD5, CD7, CD52, interleukin-2, interleukin-1, interleukin-6, tumour necrosis factor (TNF), an excreted single chain antibody to a T-cell receptor on auto-reactive T-cells, a dominant negative mutant of promyelocytic leukemia (PML), an antagonist of inflammation promoting cytokines, Bcl3, VP3 of chicken anemia virus, cytosine deaminase, nitroreductase, and linamerase.

6. An isolated fibroblast-like or a macrophage-like cell having been produced by the method of claim 1.

7. A method of delivering a nucleic acid of interest to a cell in vitro, the method comprising:

isolating a synovial cell from a subject; and infecting said isolated synovial cell with a recombinant adenovirus of subgroup C comprising a nucleic acid of interest, wherein said recombinant adenovinis' capsid comprises at least one protein of an adenovirus serotype of subgroup C and at least the tissue tropism determining domain of a fiber protein of a second adenovirus serotype, said second adenovirus serotype selected from the group consisting of adenovirus serotype 11, 16, 35, and 51.

* * * * *

UNITED STATES PATENT AND TRADEMARK OFFICE
CERTIFICATE OF CORRECTION

PATENT NO. : 7,238,528 B2  Page 1 of 1
APPLICATION NO. : 10/783510
DATED : July 3, 2007
INVENTOR(S) : Ronald Vogels et al.

It is certified that error appears in the above-identified patent and that said Letters Patent is hereby corrected as shown below:

In the specification:

| | | |
|---|---|---|
| COLUMN 12, | LINE 16, | change the semicolon after "synoviocytes" to a period |
| COLUMN 25, | LINE 39, | change "E1 a" to --E1a-- |
| COLUMN 26, | LINE 14, | change "110" to --10-- |
| COLUMN 26, | LINE 60, | insert a period after "VI" |
| COLUMN 26, | LINE 62, | insert a colon after "Parameters" |
| COLUMN 48, | LINE 38, | change "Amberg" to --Arnberg-- |
| COLUMN 49, | LINE 60, | change "Toumier" to --Tournier-- |

In the claims:
CLAIM 7, COLUMN 72, LINE 20, change "adenovinis'" to --adenovirus'--

Signed and Sealed this

Twenty-third Day of December, 2008

JON W. DUDAS
*Director of the United States Patent and Trademark Office*